United States Patent

Satow et al.

[11] Patent Number: 6,165,942
[45] Date of Patent: Dec. 26, 2000

[54] HETEROCYCLE-FUSED PYRIMIDINONE DERIVATIVE AND HERBICIDAL COMPOSITION

[75] Inventors: Jun Satow; Yoshihiro Kudo; Eitatsu Ikeda, all of Chiba; Tsutomu Nawamaki; Chiaki Kawaguchi, both of Saitama, all of Japan

[73] Assignee: Nissan Chemical Industries, Ltd., Tokyo, Japan

[21] Appl. No.: 09/283,302

[22] Filed: Apr. 1, 1999

Related U.S. Application Data

[63] Continuation of application No. PCT/JP97/03524, Oct. 2, 1997.

[30] Foreign Application Priority Data

| Oct. 3, 1996 | [JP] | Japan | 8-263319 |
| Apr. 3, 1997 | [JP] | Japan | 9-84806 |
| Aug. 27, 1997 | [JP] | Japan | 9-231299 |

[51] Int. Cl.⁷ .......................... C07D 487/04; A01N 43/54
[52] U.S. Cl. ........................ 504/225; 544/105; 544/123; 544/254; 544/255; 544/256; 544/262; 544/263; 544/278; 544/279; 544/281; 544/282; 504/240; 504/241
[58] Field of Search ................... 544/105, 254, 544/263, 278, 279, 281, 282, 255, 256, 262, 123; 504/225, 240, 241

[56] References Cited

U.S. PATENT DOCUMENTS

| 4,214,891 | 7/1980 | Wolf | 71/92 |
| 5,084,084 | 1/1992 | Satow et al. | 71/92 |
| 5,116,404 | 5/1992 | Ishii et al. | 71/92 |
| 5,127,935 | 7/1992 | Satow et al. | 71/92 |
| 5,154,755 | 10/1992 | Satow et al. | 71/92 |
| 5,356,863 | 10/1994 | Satow et al. | 504/243 |

FOREIGN PATENT DOCUMENTS 0 338 686   10/1989   European Pat. Off.

| 48-15897 | 2/1973 | Japan |
| 56-71010 | 6/1981 | Japan |
| 61-76487 | 4/1986 | Japan |
| 7-48359 | 2/1995 | Japan |

OTHER PUBLICATIONS

Komori et al. Chem. abstract 130:237582, Mar. 1999.
Hans Peter Härter, et al., Helvetica Chimica Acta, vol. 59, No. 122, pp. 1203–1212, "Vergleich Der Produkte Aus Der Reaktion Von Phenylguanidin–Derivaten Mit β–Ketoestern BZW. Propiolsäureestern (Synthese Von Pyrimidonen)", 1976.

*Primary Examiner*—Mukund J. Shah
*Assistant Examiner*—Hong Liu
*Attorney, Agent, or Firm*—Oblon, Spivak, McClelland, Maier & Neustadt, P.C.

[57] ABSTRACT

A compound represented by the general formula (I) and a salt thereof:

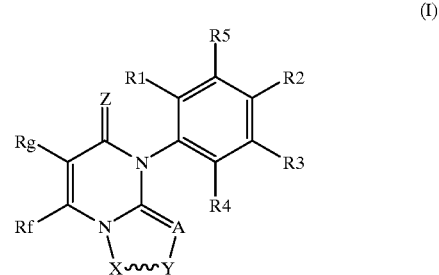

(I)

wherein:

Rf represents a $(C_1-C_4)$haloalkyl group; X~Y represents N=N or CH=N or the like; A represents a nitrogen atom or CH; Z represents an oxygen or sulfur atom; Rg represents a hydrogen or halogen atom and the like; R1, R2, R3, R4 and R5 are each independently represent a hydrogen or halogen atom or a nitro or cyano group or the like.

9 Claims, No Drawings

HETEROCYCLE-FUSED PYRIMIDINONE DERIVATIVE AND HERBICIDAL COMPOSITION

This is a continuation of PCT/JP97/03524, filed on Oct. 2, 1997.

FIELD OF THE INVENTION

The present invention relates to a herbicide comprising a novel heterocycle-fused pyrimidinone derivative as an active ingredient.

BACKGROUND OF INVENTION

So far, many kinds of herbicides have been put to practical use in order to protect important crops, such as rice, soybean, wheat, corn, cotton and sugar beet from weed damage and to increase the productivity of said crops. Existing herbicides, however, do not necessarily meet the all performance to be needed.

No herbicidal effect of the compounds according to the present invention has been known at all so far, each of which compounds has a pyrimidinone ring carrying a haloalkyl group at 6-position and a substituted phenyl group at 3-position and fused with a heterocyclic ring at 1,2-positions.

SUMMARY OF THE INVENTION

Earnestly studying for herbicidal effect of novel heterocycle-fused pyrimidinone derivatives, the present inventors have found that the compounds of the present invention represented by the following general formula provide a good herbicidal effect and have achieved the present invention.

That is, the present invention is a novel heterocycle-fused pyrimidinone derivative (hereinafter, referred to as "the compound of the present invention") represented by the general formula (I) and a herbicide comprising the same as an active ingredient:

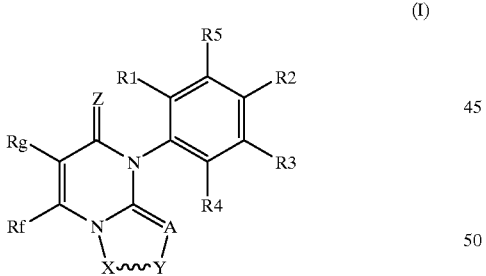

(I)

wherein:
Rf represents a $(C_1–C_4)$haloalkyl group;
X and Y each independently represent a carbon, nitrogen, oxygen or sulfur atom;
X~Y represents:
N=N,
C(Ra)=C(Rb) (wherein Ra and Rb each independently represent a hydrogen or halogen atom, or a $(C_1–C_4)$alkyl, $(C_1–C_4)$alkoxy, $(C_1–C_4)$haloalkyl, hydroxy, amino, mercapto, carboxyl, hydroxymethyl, carbamoyl, formyl, $(C_1–C_4)$alkylcarbonyl, $(C_1–C_4)$alkoxycarbonyl, $(C_1–C_4)$alkylamino, $(C_2–C_6)$alkenyl, $(C_2–C_6)$alkynyl, $(C_1–C_4)$alkylmercapto, $(C_3–C_6)$alkenylamino, $(C_3–C_6)$alkynylamino, benzyloxy, benzylamino, $(C_1–C_4)$alkylsulfinyl, $(C_1–C_4)$alkylsulfonyl or pyridyl group, or an optionally substituted phenyl group (SP1) (wherein the optionally substituted phenyl group (SP1) is a phenyl group which may be substituted with a halogen atom or a $(C_1–C_4)$alkyl, $(C_1–C_4)$alkoxy, $(C_1–C_4)$haloalkyl, $(C_1–C_4)$haloalkoxy or phenyl group),
C(Ra)=N (wherein Ra represents the same meaning as defined above),
N=C(Ra) (wherein Ra represents the same meaning as defined above),
CH(Ra)CH(Rb) (wherein Ra and Rb represent the same meanings as defined above), or
$CH_2CH_2CH_2$, CH=$CHCH_2$ or $CH_2$CH=CH, or
NHC(Ra)Rb (wherein Ra and Rb represent the same meanings as defined above),
C(Ra)(Rb)NH (wherein Ra and Rb represent the same meanings as defined above), or
C(=O)C(=O), $CH_2$C(=O)NH or $CH_2CH_2SO_2$, or
C(=O)CH(Ra) (wherein Ra represents the same meaning as defined above),
CH(Ra)C(=O) (wherein Ra represents the same meaning as defined above), or
C(=O)NH, C(=S)NH, NHC(=O) or NHC(=S), or
C(=O)C(Ra)=N (wherein Ra represents the same meaning as defined above),
C(=O)C(Ra)=C(Rb) (wherein Ra and Rb represent the same meanings as defined above),
C(Ra)=C(Rb)C(=O) (wherein Ra and Rb represent the same meanings as defined above),
N=C(Ra)C(=O) (wherein Ra represents the same meaning as defined above),
CH(Ra)C(=O)NH (wherein Ra represents the same meaning as defined above),
C(=O)N(Ra)C(=O) (wherein Ra represents the same meaning as defined above),
C(Ra)=NC(=O) (wherein Ra represents the same meaning as defined above),
C(Ra)O (wherein Ra represents the same meaning as defined above), or
C(=O)O, OC(=O) or SC(=O);
A represents a nitrogen atom or CH;
Z represents:
an oxygen or sulfur atom,
NRc (wherein Rc is a hydrogen atom, or a $(C_1–C_4)$alkyl, $(C_1–C_4)$alkoxycarbonyl or $(C_1–C_4)$alkoxycarbonylmethyl group, or an optionally substituted phenyl group (SP2) (wherein the optionally substituted phenyl group (SP2) is a phenyl group which may be substituted with a halogen atom or a $(C_1–C_4)$alkyl, $(C_1–C_4)$alkoxy or $(C_1–C_4)$haloalkyl group), or
NNHRc (wherein Rc represents the same meaning as defined above);
Rg represents a hydrogen or halogen atom, or a cyano, $(C_1–C_4)$alkoxycarbonyl, $(C_3–C_6)$alkenyl, $(C_3–C_6)$alkynyl or $(C_1–C_4)$alkyl group;
R1, R2, R3, R4 and R5 each independently represent:
a hydrogen or halogen atom,
a nitro, cyano, thiocarbamoyl, carbamoyl, mercapto, hydroxyl, amino, formyl, carboxyl, vinyl, ethynyl, trimethylsilylethynyl, cyanomethyl, sulfamoyl, $(C_1–C_8)$alkyl, $(C_3–C_8)$alkenyl, $(C_1–C_4)$alkylsulfonyl, $(C_3–C_8)$alkynyl, $(C_3–C_8)$cycloalkyl, $(C_1–C_4)$haloalkyl, $(C_3–C_8)$haloalkenyl, $(C_3–C_8)$haloalkynyl, $(C_1–C_4)$acyl, $(C_1–C_4)$alkoxy$(C_1–C_2)$alkyl or $(C_1–C_4)$alkylsulfinyl group, or an optionally substituted phenyl group (SP3) (wherein the optionally substituted phenyl group (SP3) is a phenyl group which may be substituted with a halogen atom, or a ($C_1$–$C_4$)haloalkyl, ($C_1$–$C_4$)alkyl, ($C_1$–$C_4$)alkoxy, ($C_1$–$C_4$)haloalkoxy, methanesulfonyl, ($C_1$–$C_4$)alkoxycarbonyl, nitro, hydroxyl, amino or cyano group, or a group —O—CH($CH_3$)$CO_2$($C_1$–$C_4$)alkyl or —O—$CH_2CO_2$($C_1$–$C_4$)alkyl), a group —Q-(optionally substituted phenyl group (SP3)) (wherein Q is a saturated or unsaturated ($C_1$–$C_6$)alkylene chain which may be branched and substituted with a halogen atom, and the optionally substituted phenyl group (SP3) represents the same meaning as defined above), a group —O—Q-(optionally substituted phenyl group (SP3)) (wherein Q and the optionally substituted phenyl group (SP3) represent the same meanings as defined above), a group —S—Q-(optionally substituted phenyl group (SP3)) (wherein Q and the optionally substituted phenyl group (SP3) represent the same meanings as defined above), a group —NH—Q-(optionally substituted phenyl group (SP3)) (wherein Q and the optionally substituted phenyl group (SP3) represent the same meanings as defined above), a group —O-(optionally substituted phenyl group (SP3)) (wherein the optionally substituted phenyl group (SP3) represents the same meaning as defined above), a group —S-(optionally substituted phenyl group (SP3)) (wherein the optionally substituted phenyl group (SP3) represents the same meaning as defined above), a group —NH-(optionally substituted phenyl group (SP3)) (wherein the optionally substituted phenyl group (SP3) represents the same meaning as defined above), —O—R11 (wherein R11 represents a ($C_1$–$C_8$)alkyl, ($C_3$–$C_8$)cycloalkyl, ($C_3$–$C_8$)cycloalkyl($C_1$–$C_4$)alkyl, ($C_3$–$C_8$)alkenyl, ($C_3$–$C_8$)alkynyl, $C_3$–$C_8$) haloalkenyl, ($C_1$–$C_4$)haloalkylcarbonyl, $C_3$–$C_8$) haloalkynyl, ($C_1$–$C_4$)haloalkyl, ($C_1$–$C_4$)alkoxy ($C_1$–$C_4$)alkyl, cyanomethyl or ($C_1$–$C_4$)acyl group), —NH—R11 (wherein R11 represents the same meaning as defined above), —S—R11 (wherein R11 represents the same meaning as defined above), or a group —CON[($C_1$–$C_4$)alkyl]$_2$ or —CONH[($C_1$–$C_4$)alkyl], or —$CO_2$R12 (wherein R12 represents a ($C_1$–$C_8$)alkyl, ($C_3$–$C_8$)cycloalkyl, ($C_3$–$C_8$)alkenyl or ($C_3$–$C_8$) alkynyl group, or an optionally substituted phenyl group (SP3) (wherein the optionally substituted phenyl (SP3) represents the same meaning as defined above) or a group —Q-(optionally substituted phenyl group (SP3)) (wherein Q and the optionally substituted phenyl group represent the same meanings as defined above), or an oxetan-3-yl, ($C_1$–$C_4$) alkoxycarbonylmethyl or [($C_1$–$C_4$)alkyl]$_2$amino group), —CONHR12 (wherein R12 represents the same meaning as defined above), —Q—$CO_2$R12 (wherein Q and R12 represent the same meanings as defined above), —O—Q—$CO_2$R12 (wherein Q and R12 represent the same meanings as defined above), —NH—Q—$CO_2$R12 (wherein Q and R12 represent the same meanings as defined above), —S—Q—$CO_2$R12 (wherein Q and R12 represent the same meanings as defined above), —$NHSO_2$R13 (wherein R13 represents a ($C_1$–$C_8$) alkyl, ($C_1$–$C_4$)haloalkyl, ($C_3$–$C_6$)cycloalkyl, ($C_3$–$C_8$)alkenyl, ($C_3$–$C_8$)alkynyl, benzyl or phenyl group), —N($SO_2$R13)$_2$ (wherein R13 represents the same meaning as defined above), —$CONHSO_2$R14 (wherein R14 represents a ($C_1$–$C_4$) alkyl or ($C_1$–$C_4$)haloalkyl group), —N(R15)$SO_2$R13 (wherein R13 represents the same meaning as defined above and R15 represents a ($C_1$–$C_6$)alkyl, ($C_3$–$C_8$)alkenyl, ($C_3$–$C_8$)alkynyl, ($C_1$–$C_4$)haloalkyl, ($C_3$–$C_8$)haloalkenyl, ($C_3$–$C_8$) haloalkynyl, ($C_1$–$C_6$)acyl, formyl, cyano($C_1$–$C_4$) alkyl, ($C_1$–$C_4$)alkoxy($C_1$–$C_4$)alkyl or ($C_1$–$C_4$) alkoxycarbonyl group, or a group —C(=O) (optionally substituted phenyl group (SP3)) (wherein the optionally substituted phenyl group (SP3) represents the same meaning as defined above)), —$NHCO_2$R16 (wherein R16 represents a ($C_1$–$C_6$) alkyl, ($C_3$–$C_8$)alkenyl, ($C_3$–$C_8$)alkynyl, ($C_1$–$C_4$) haloalkyl or phenyl group, or a group —Q-(optionally substituted phenyl group (SP3)) (wherein Q and the optionally substituted phenyl group (SP3) represent the same meanings as defined above)), —O—$CO_2$R16 (wherein R16 represents the same meaning as defined above), —N(R15)$CO_2$R16 (wherein R15 and R16 represent the same meanings as defined above), —N(R15)R11 (wherein R11 and R15 represent the same meanings as defined above), or a 2,3-epoxy-2-methylpropyl, 2-methyl-2-propenyl, 1,3-dioxolan-2-yl or 1,3-dioxan-2-yl group; or alternatively, R2 and R3 may form together a heterocyclic ring represented by the following formulae (a), (b) or (c):

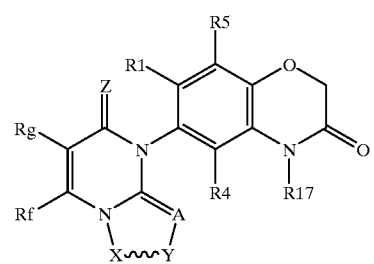

(a)

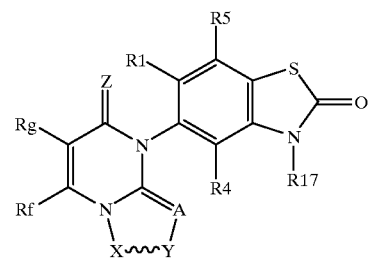

(b)

-continued (c)

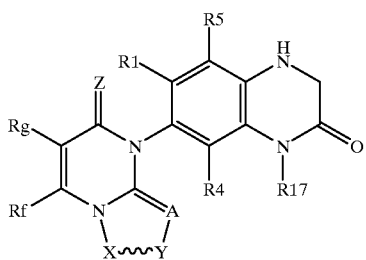

wherein Rf, Rg, A, X, Y, Z, R1, R4 and R5 of (a), (b) and (c) represent the same meanings as defined above, and R17 represents a ($C_1$–$C_6$)alkyl, ($C_3$–$C_8$)alkenyl, ($C_3$–$C_8$)alkynyl, ($C_1$–$C_4$)haloalkyl, ($C_3$–$C_8$)haloalkenyl, ($C_3$–$C_8$)haloalkynyl, ($C_1$–$C_6$)acyl, formyl, benzoyl, ($C_1$–$C_6$)haloalkylcarbonyl, phenacyl, ($C_3$–$C_8$)cycloalkyl($C_1$–$C_4$)alkyl or ($C_1$–$C_4$)alkoxy($C_1$–$C_4$)alkyl group, or a group —Q—$CO_2$—($C_1$–$C_4$)alkyl (wherein Q represents the same meaning as defined above), —Q—CN (wherein Q represents the same meaning as defined above) or —Q-(optionally substituted phenyl group (SP3)) (wherein Q and the optionally substituted phenyl group (SP3) represent the same meanings as defined above);

provided that when optical isomers, diastereomers and/or geometrical isomers of the compounds defined above can exist, both the mixture of the said isomers and the isolated isomers are included in the scope of the present invention.

DETAILED DESCRIPTION OF THE INVENTION

In the formula (I), Rf may be $CF_3$, $CF_2Cl$, $CF_2H$, CFClH, $CF_3CF_2$ or $CF_2ClCF_2$, and is preferably $CF_3$.

Rg may be H, F, Cl, Br, C≡N, $CO_2Me$, $CH_2CH$=$CH_2$, $CH_2$≡CH, Me, Et, Pr, iso-Pr or Bu, and is preferably H or F.

Z may be an oxygen or sulfur atom, or NH, NMe, NEt, NPr, NBu, N-tert-Bu, $NCO_2Me$, $NCO_2Et$, $NCH_2CO_2Me$, $NCH_2CO_2Et$, NPh, N-(4-Cl-Phenyl), N-(3-Cl-phenyl), N-(2-Cl-phenyl), NNHMe, NNHEt, NNHPr, NNHBU, NNH-tert-Bu, NNH-(4-Cl-phenyl), $NNH_2$, NNH-(3-Cl-phenyl), NNH-(2-Cl-phenyl), $NNHCH_2CO_2Me$, $NNHCH_2CO_2Et$, NNHPh, $NNHCO_2Me$ or $NNHCO_2Et$, and is preferably an oxygen atom.

A may be CH or N, and is preferably N.

X~Y may be N=N, CH=N, N=CH, C(Cl)=N, N=C(Cl), C(Br)=N, N=C(Br), CH=CH, C(Cl)=CH, CH=C(Cl), C(Br)=CH, CH=C(Br), C(Me)=CH, CH=C(Me), N=C(Me), N=C(Ph), C(Me)=N, C(Ph)=N, C(Et)=CH, CH=C(Et), C(Pr)=CH, CH=C(Pr), $CH_2CH_2$, $CH_2CH$(Me), CH(Me)$CH_2$, $CH_2CH$(Et), CH(Et)$CH_2$, $CH_2CH$(Pr), CH(Pr)$CH_2$, $CH_2CH_2CH_2$, CH=$CHCH_2$, $CH_2CH$=CH, $CH_2C$(=O)NH, $CH_2CH_2SO_2$, C(=O)C(=O), $CH_2C$(=O), C(=O)NH, C(=S)NH, NHC(=O), NHC(=S), C(=O)CH=N, C(=O)CH=CH, CH=CHC(=O), N=CHC(=O), $CH_2C$(=O)NH, C(=O)NHC(=O), C(=O)N(Me)C(=O), CH=NC(=O), $CH_2O$, C(=O)O, OC(=O), SC(=O) or C(=O)S, and is preferably CH=N, N=CH, CH=CH, $CH_2CH_2$, C($CH_3$)=CH, C($C_2H_5$)=CH, CH=C($CH_3$), CH=C($C_2H_5$), CH($CH_3$)$CH_2$, CH($C_2H_5$)$CH_2$, $CH_2CH$($CH_3$), $CH_2CH$($C_2H_5$), C($CH_2CH_2CH_3$)=CH or CH=C($CH_2CH_2CH_3$), and is more preferably CH=CH.

R1 may be H, Cl, F, Br or I, and is preferably H, Cl or F.

R5 may be H, Cl, F or Br, and is preferably H.

R2 may be H, Cl, F, Br, I, CN, $CSNH_2$, $CONH_2$, C≡CH, C≡$CSiMe_3$, CH=$CH_2$, Me, Et, Pr, iso-Pr, O-Me, O-Et, $SO_2NH_2$, $OCH_2CO_2Me$, $OCH_2CO_2Et$, $OCH_2CH_2CO_2Et$, $CF_3$, $CF_2CF_3$, $CF_2Cl$, $CF_2H$, $CF_3O$, $NO_2$, $HCF_2O$, $ClCH_2$, $BrCH_2$, SMe, $SO_2Me$, OH, SH, $NH_2$, CHO, $CO_2H$, $CO_2Me$, $CO_2Et$, $CH_2CN$, NHMe, $NMe_2$, $OCH_2OMe$, $OCH_2Ph$, $OCH_2$(4-Cl-phenyl), $OCH_2$(4-Br-phenyl), $OCH_2$(4-Me-phenyl), $OCH_2$(4-Cl-2-(OCH(Me)$CO_2Me$)-phenyl), $OCH_2$(4-Me-2-(OCH(Me)$CO_2Me$)-phenyl), $OCH_2$(4-Cl-2-(OCH(Me)$CO_2Et$)-phenyl), $OCH_2$(4-Me-2-(OCH(Me)$CO_2Et$)-phenyl), $NHCH_2Ph$, $NHCH_2$(4-Cl-phenyl), $NHCH_2$(4-Br-phenyl), $NHCH_2$(4-Me-phenyl), $NHCH_2$(4-Cl-2-(OCH(Me)$CO_2Me$)-phenyl), $NHCH_2$(4-Me-2-(OCH(Me)$CO_2Me$)-phenyl), $SCH_2Ph$, $SCH_2$(4-Cl-phenyl), $SCH_2$(4-Br-phenyl), $SCH_2$(4-Me-phenyl), $SCH_2$(4-Cl-2-(OCH(Me)$CO_2Me$)-phenyl), $SCH_2$(4-Me-2-(OCH(Me)$CO_2Me$)-phenyl), OCH(Me)$CO_2Me$, OCH(Me)$CO_2Et$, $NHCH_2CO_2Me$, $NHCH_2CO_2Et$, $SCH_2CO_2Me$ or $SCH_2CO_2Et$, and is preferably F, Cl, Br, I, CN, $NO_2$ or $CSNH_2$.

R3 may be H, Cl, F, Br, I, CHO, $CO_2H$, $CONH_2$, $SO_2Cl$, COMe, SH, OH, $NH_2$, $NO_2$, CN, Phenyl, Me, Et, Pr, iso-Pr, Bu, sec-Bu, iso-Bu, tert-Bu, Pn, neo-Pn, tert-Pn, cyclo-Pr, cyclo-Bu, cyclo-Pn, cyclo-Hex, $CH_2CH$=$CH_2$, CH(Me)CH=$CH_2$, $CH_2C$≡CH, CH(Me)C≡CH, O-Me, O-Et, O-iso-Pr, O—Pr, O-Bu, O-sec-Bu, O-iso-Bu, O-cyclo-Pn, O-cyclo-Pr, O-cyclo-Hex, O-neo-Pn, O-tert-Pn, O-Pn, O-Hex, O-Hep, O-Oct, $OCH_2CH$=$CH_2$, OCH(Me)CH=$CH_2$, OC(Me)$_2CH$=$CH_2$, $OCH_2C$≡CH, OCH(Me)C≡CH, OC(Me)$_2C$≡CH, $OCH_2CH$=C(Cl)H, $OCH_2C$(Cl)=$CH_2$, $OCH_2CF_3$, $OCH_2CH_2OMe$, $OCH_2CH_2OEt$, $OCH_2OMe$, $OCH_2OEt$, $OCH_2$-cyclo-Pr, $OCH_2CN$, OCOMe, OCOEt, OCOPr, OCO-iso-Pr, $OCH_2C$(Me)=$CH_2$, O-iso-Pn, S-Me, S-Et, S-iso-Pr, S—Pr, S-Bu, S-sec-Bu, S-iso-Bu, S-cyclo-Pn, S-cyclo-Pr, S-cyclo-Hex, S-neo-Pn, S-tert-Pn, S-Pn, S-Hex, S-Hep, S-Oct, $SCH_2CH$=$CH_2$, SCH(Me)CH=$CH_2$, SC(Me)$_2CH$=$CH_2$, $SCH_2C$≡CH, SCH(Me)C≡CH, SC(Me)$_2C$≡CH, $SCH_2CH$=C(Cl)H, $SCH_2C$(Cl)=$CH_2$, $SCH_2CF_3$, $SCH_2CH_2OMe$, $SCH_2CH_2OEt$, $SCH_2OMe$, $SCH_2OEt$, $SCH_2$-cyclo-Pr, $SCH_2CN$, NH-Me, NH-Et, NH-iso-Pr, NH—Pr, NH-Bu, NH-sec-Bu, NH-iso-Bu, NH-cyclo-Pn, NH-cyclo-Pr, NH-cyclo-Hex, NH-neo-Pn, NH-tert-Pn, NH-Pn, NH-Hex, NH-Hep, NH-Oct, $NHCH_2CH$=$CH_2$, NHCH(Me)CH=$CH_2$, NHC(Me)$_2CH$=$CH_2$, $NHCH_2C$≡CH, NHCH(Me)C≡CH, NHC(Me)$_2C$≡CH, $NHCH_2CH$=C(Cl)H, $NHCH_2C$(Cl)=$CH_2$, $NHCH_2CF_3$, $NHCH_2CH_2OMe$, $NHCH_2CH_2OEt$, $NHCH_2OMe$, $NHCH_2OEt$, $NHCH_2$-cyclo-Pr, $NHCH_2CN$, $CO_2Me$, $CO_2Et$, $CO_2$-iso-Pr, $CO_2Pr$, $CO_2$-cyclo-Pr, $CO_2Bu$, $CO_2$-sec-Bu, $CO_2$-iso-Bu, $CO_2$-tert-Bu, $CO_2$-cyclo-Bu, $CO_2$-Pn, $CO_2$-cyclo-Pn, $CO_2Pn$, $CO_2$-neo-Pn, $CO_2$-tert-Pn, $CO_2$-Hex, $CO_2$-cyclo-Hex, $CO_2$-Hep, $CO_2$-Oct, $CO_2N$(Me)$_2$, $CO_2N$(Et)$_2$, $CO_2CH_2CO_2Me$, $CO_2CH_2CO_2Et$, $CO_2CH_2CO_2Pr$, $CO_2Ph$, $CO_2CH_2Ph$, CONHEt, CONHPr, CONHBu, CONH-tert-Bu, CONHPh, $CONHCH_2Ph$, $CH_2CH$(Cl)$CO_2Me$, $CH_2CH$(Cl)$CO_2Et$, $CH_2CH_2CO_2Me$, $CH_2CH_2CH_2CO_2Me$, $CH_2CO_2Me$, CH=$CHCO_2Me$, CH=$CHCO_2Et$, $OCH_2CO_2Me$, $OCH_2CO_2Et$, $OCH_2CO_2Pr$, $OCH_2CO_2Bu$, $OCH_2CO_2Pn$, $OCH_2CO_2Hex$, $OCH_2CO_2$-cyclo-Pn, $OCH_2CO_2$-iso-Pr, $OCH_2CO_2CH_2Ph$, OCH(Me)$CO_2Me$, OCH(Me)$CO_2Et$, OCH(Me)$CO_2Pr$, OCH(Me)$CO_2$-iso-Pr, OCH(Me)$CO_2Pn$, OCH(Me)$CO_2$-cyclo-Pn, $SCH_2CO_2Me$, $SCH_2CO_2Et$, $SCH_2CO_2Pr$, $SCH_2CO_2Bu$, $SCH_2CO_2Pn$, $SCH_2CO_2Hex$, $SCH_2CO_2$-cyclo-Pn, $SCH_2CO_2$-iso-Pr, $SCH_2CO_2CH_2Ph$, SCH(Me)$CO_2Me$, SCH(Me)$Co_2Et$, SCH(Me)$CO_2Pr$, SCH (Me)CO$_2$-iso-Pr, SCH(Me)CO$_2$Pn, SCH(Me)CO$_2$-cyclo-Pn, NHCH$_2$CO$_2$Me, NHCH$_2$CO$_2$Et, NHCH$_2$CO$_2$Pr, NHCH$_2$CO$_2$Bu, NHCH$_2$CO$_2$Pn, NHCH$_2$CO$_2$Hex, NHCH$_2$CO$_2$-cyclo-Pn, NHCH$_2$CO$_2$-iso-Pr, NHCH$_2$CO$_2$CH$_2$Ph, NHCH(Me)CO$_2$Me, NHCH(Me)CO$_2$Et, NHCH(Me)CO$_2$Pr, NHCH(Me)CO$_2$-iso-Pr, NHCH(Me)CO$_2$Pn, NHCH(Me)CO$_2$-cyclo-Pn, NHCO$_2$Me, NHCO$_2$Et, NHCO$_2$Pr, NHCO$_2$-iso-Pr, NHCO$_2$Bu, NHCO$_2$-cyclo-Pr, NHCO$_2$-cyclo-Pn, NHCO$_2$-iso-Bu, NHCO$_2$-sec-Bu, NHCO$_2$-tert-Bu, NHCO$_2$CH$_2$CH=CHCH$_3$, NHCO$_2$CH$_2$CH=CH$_2$, NHCO$_2$CH$_2$C≡CH, NHCO$_2$Ph, NHCO$_2$CH$_2$Ph, NHCO$_2$CH$_2$-(2-Me-Ph), NHCO$_2$CH$_2$-(3-Me-Ph), NHCO$_2$CH$_2$-(4-Me-Ph NHCO$_2$CH$_2$-(4-Et-Ph), NHCO$_2$CH$_2$-(2-MeO-Ph), NHCO$_2$CH$_2$-(3-MeO-Ph), NHCO$_2$CH$_2$-(4-MeO-Ph), NHCO$_2$CH$_2$-(4-Cl-Ph), NHCO$_2$CH$_2$-(4-F-Ph), NHCO$_2$CH$_2$-(4-CF$_3$-Ph), NHCO$_2$CH$_2$-(2-F-Ph), NHCO$_2$CH$_2$-(3-F-Ph), NHCO$_2$CH$_2$-(3-Cl-Ph), NHCO$_2$CH$_2$-(2-Cl-Ph), NHCO$_2$CH$_2$-(4CF$_3$O-Ph), NHSO$_2$Me, NHSO$_2$Et, NHSO$_2$Pr, NHSO$_2$-iso-Pr, NHSO$_2$Bu, NHSO$_2$CH$_2$Ph, NHSO$_2$CHCl$_2$, NHSO$_2$CH$_2$Cl, NHSO$_2$CH$_2$CH$_2$Cl, NHSO$_2$CH$_2$CH$_2$CH$_2$Cl, NHSO$_2$CH$_2$CF$_3$, NHSO$_2$Ph, N(SO$_2$Et)CO$_2$Et, N(CH$_2$OMe)SO$_2$Et, N(CH$_2$CH=CH$_2$)SO$_2$Et, N(CH$_2$C≡CH)SO$_2$Et, N(Me)SO$_2$Me, N(SO$_2$Me)$_2$, N(SO$_2$Et)$_2$, N(SO$_2$Pr)$_2$, N(Et)SO$_2$Et, N(Me)SO$_2$Et, N(Et)SO$_2$Et, N(Pr)SO$_2$Et, N(COMe)SO$_2$Et, N(CH$_2$OMe)SO$_2$Me, N(CH$_2$OEt)SO$_2$Me, N(CH$_2$CH=CH$_2$)SO$_2$Me, N(CH$_2$C≡CH)SO$_2$Me, CONHSO$_2$Me, CONHSO$_2$Et, CONHSO$_2$CF$_3$, 1,3-dioxolan-2-yl, 1,3-dioxan-2-yl, 4-[1-(ethoxycarbonyl)ethyloxy]phenyloxy, 4-[1-(methoxycarbonyl)ethyloxy]phenyloxy, N(Me)CO$_2$Me, N(CH$_2$C≡CH)CO$_2$Me, N(Me)COMe, NHCOMe, NHCOPr, N(CH$_2$C≡CH)COMe, N(CH$_2$CH=CH$_2$)CO$_2$Me, N(Me)CO$_2$CH$_2$-(4-Me-Ph), N(CH$_2$C≡CH)CO$_2$Et, N(CH$_2$C≡N)CO$_2$Me, N(CO-tert-Bu)SO$_2$Me, N(CO-tert-Bu)SO$_2$Et, N(2-MeO-benzoyl)SO$_2$Me, N(3-MeO-benzoyl)SO$_2$Me, N(4-MeO-benzoyl)So$_2$Me, N(2-MeO-benzoyl)SO$_2$Et, N(3-MeO-benzoyl)SO$_2$Et, N(4-MeO-benzoyl)SO$_2$Et, N(4-Me-benzoyl)SO$_2$Me, N(4-Me-benzoyl)SO$_2$Et, N(4-Cl-benzoyl)SO$_2$Me, N(4-Cl-benzoyl)SO$_2$Et, CO$_2$-(oxetan-3-yl), N(CHO)CH$_2$CO$_2$Me, N(CHO)CH$_2$CO$_2$Et, N(CHO)CH$_2$CO$_2$Pn, N(CHO)CH(Me)CO$_2$Me, N(CHO)CH(Me)CO$_2$Et, N(COMe)CH$_2$CO$_2$Me, NHCOCF$_2$Cl, NHCOCF$_3$, CONHMe, CONMe$_2$CONEt$_2$, N(COMe)CH$_2$CO$_2$Et, N(COMe)CH$_2$CO$_2$Pn, N(COMe)CH(Me)CO$_2$Me, N(COMe)CH(Me)CO$_2$Et, N(CH$_2$C≡N)SO$_2$Me, CH=C(Cl)CO$_2$Me, CH=C(Cl)CO$_2$Et, OCH$_2$(4-Cl-2-(OCH(Me)Co$_2$Me)-phenyl) or OCH$_2$(4-Me-2-(OCH(Me)CO$_2$Me)-phenyl).

R4 may be H, F, Cl, Me, Et, Pr, iso-Pr, MeO, EtO, PrO, CH$_2$C(Me)=CH$_2$, CH$_2$CH=CH$_2$, CH$_2$C≡CH, 2,3-epoxy-2-methylpropyl or 2,3-epoxypropyl, and is preferably H or F.

In this connection, when R4 is 2,3-epoxy-2-methylpropyl or CH$_2$C(Me)=CH$_2$, R3 may be then a substituent bound to the phenyl group via an oxygen atom.

R2 and R3 may also form together a ring, in which —R2~R3— may be —OCH$_2$C(=O)N(R17)—, —SC(=O)N(R17)— or —NHCH$_2$C(=O)N(R17)—, and is preferably —OCH$_2$C(=O)N(R17)—.

R17 is a substituent which may be Me, Et, Pr, iso-Pr, Bu, sec-Bu, iso-Bu, CH$_2$CH=CH$_2$, CH$_2$C≡CH, CH$_2$C=N, CH$_2$CH$_2$F, CH$_2$CH$_2$Cl, CH$_2$CH$_2$CH$_2$F, CH$_2$OMe, OMe, OEt, CH$_2$OEt, CH$_2$CH$_2$CH$_2$Cl, CH$_2$CH$_2$CH$_2$CH$_2$F, CH$_2$CCl=CH$_2$, CH$_2$CBr=CH$_2$, CH(Me)C≡CH, CH(Me)CH=CH$_2$ or CH(Me)C≡N.

The abbreviations used in the specification have the following meanings:

Me: CH$_3$,
Et: CH$_2$CH$_3$,
Pr: CH$_2$CH$_2$CH$_3$,
iso-Pr: CH(CH$_3$)$_2$,
cyclo-Pr: CH(CH$_2$)$_2$,
Bu: CH$_2$CH$_2$CH$_2$CH$_3$,
sec-Bu: CH(CH$_3$)C$_2$H$_5$,
iso-Bu: CH$_2$CH(CH$_3$)$_2$,
tert-Bu: C(CH$_3$)$_3$,
cyclo-Bu: CH(CH$_2$)$_3$,
Pn: CH$_2$CH$_2$CH$_2$CH$_2$CH$_3$,
cyclo-Pn: CH(CH$_2$)$_4$,
iso-Pn: CH$_2$CH$_2$CH(CH$_3$)$_2$,
neo-Pn: CH$_2$C(CH$_3$)$_3$ ,
cyclo-Hex: CH(CH$_2$)$_5$,
tert-Pn: C(CH$_3$)$_2$C$_2$H$_5$,
Hex: (CH$_2$)$_5$CH$_3$,
Hep: (CH$_2$)$_6$CH$_3$,
Oct: (CH$_2$)$_7$CH$_3$,
Ph, phenyl: C$_6$H$_5$,
4-Cl-Ph: 4-Cl-phenyl.

The compounds of the present invention include compounds which can be applied as a herbicide for upland field and non-arable land through soil treatment as well as foliage treatment to show high herbicidal activities at a low dosage against various cropland weeds including broad-leaved weeds such as Solanaceae weeds represented by *Solanum nigrum* and *Datura stramonium* and the like, Malvaceae weeds represented by *Abutilon theophrasti* and *Sida spinosa* and the like, Convolvulaceae weeds represented by Ipomoea spps. such as *Ipomoea purpurea,* and Calystegia spps. and the like, Amaranthaceae weeds represented by *Amaranthus lividus* and *Amaranthus viridis* and the like, Compositae weeds represented by *Xanthium pensylvanicum, Ambrosia artemisiaefolia, Helianthus annuus, Galinsoga ciliata, Cirsium arvense, Senecio vulgaris* and *Erigeron annuus* and the like, Cruciferae weeds represented by *Rorippa indica, Sinapis arvensis* and *Capsella bursapastoris* and the like, Polygonaceae weeds represented by *Polygonum blumei* and *Polygonum convolvulus* and the like, Portulacaceae weeds represented by *Portulaca oleracea* and the like, Chenopodiaceae weeds represented by *Chenopodiuum album, Chenopodiuum ficifolium* and *Kochias coparia* and the like, Caryophyllaceae weeds represented by *Stellaria media* and the like, Scrophulariaceae weeds represented by *Veronica persica* and the like, Commelinaceae weeds represented by *Commelina communis* and the like, Labiatae weeds represented by *Lamium amplexicaule* and *Lamium purpureum* and the like, Euphorbiaceae weeds represented by *Euphorbia supina* and *Euphorbia maculata* and the like, Rubiaceae weeds represented by *Galium aparine* and Rubia akane and the like, Violaceae weeds represented by *Viola mandshurica* and the like, and Leguminosae weeds represented by *Sesbania exaltata* and *Cassia obtusifolia* and the like; Graminaceous weeds represented by *Sorghum bicolor, Panicum dichotomiflorum, Sorghum halepense, Echinochloa crus-galli* var. *crus-galli, Echinochloa crus-galli* var. *praticola, Echinochloa utilis, Digitaria adscendens, Avena fatua, Eleusine indica, Setaria viridis* and *Alopecurus aegualis* and the like; and Cyperaceous weeds represented by *Cyperus rotundus* (*Cyperus esculentus*) and the like.

In addition, the compounds of the present invention include compounds which can be applied as a herbicide for paddy field through soil treatment as well as foliage treatment under flooded condition to show high herbicidal activities at a low dosage against various paddy weeds such as Alismataceae weeds represented by *Alisma canaliculatum, Sagittaria trifolia* and *Sagittaria pygmaea* and the like, Cyperaceae weeds represented by *Cyperus difformis, Cyperus serotinus, Scirpus juncoides* and *Eleocharis kuroguwai* and the like, Scrothulariaceae weeds represented by *Lindernia pyxidaria* and the like, Potenderiaceae weeds represented by *Monochoria vaginalis* and the like, Potamogetonaceae weeds represented by *Potamogeton distinctus* and the like, Lythraceae weeds represented by *Rotala indica* and the like, and Graminaceous weeds represented by *Echinochloa oryzicola, Echinochloa crus-galli* var. *formosensis* and *Echinochloa crus-galli* var. *crus-galli*.

Further, the compounds of the present invention include compounds which have a high safety against the important crops such as rice, wheat, barley, sorghum, groundnut, corn, soybean, cotton and sugar beet.

The compounds of the present invention can be synthesized according to the process described in, for example, Schemes 1 to 15 (wherein Z, A, Ra, Rc, Rf, Rg and R1 to R5 in Schemes 1 to 15 have the same meanings as defined above, R' and R" each independently represent $(C_1-C_4)$ alkyl, Hal represents a halogen atom, and n represents an integer of 2 or 3).

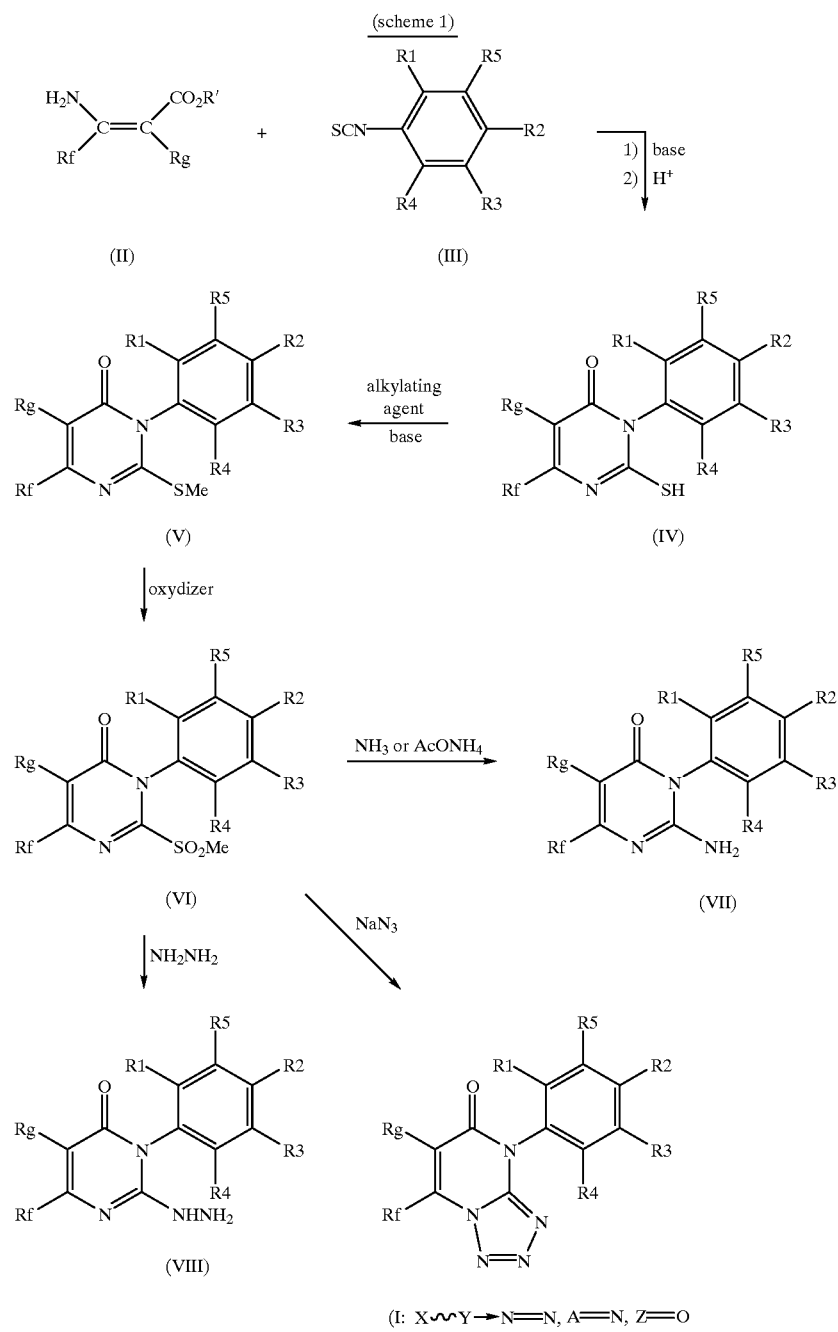

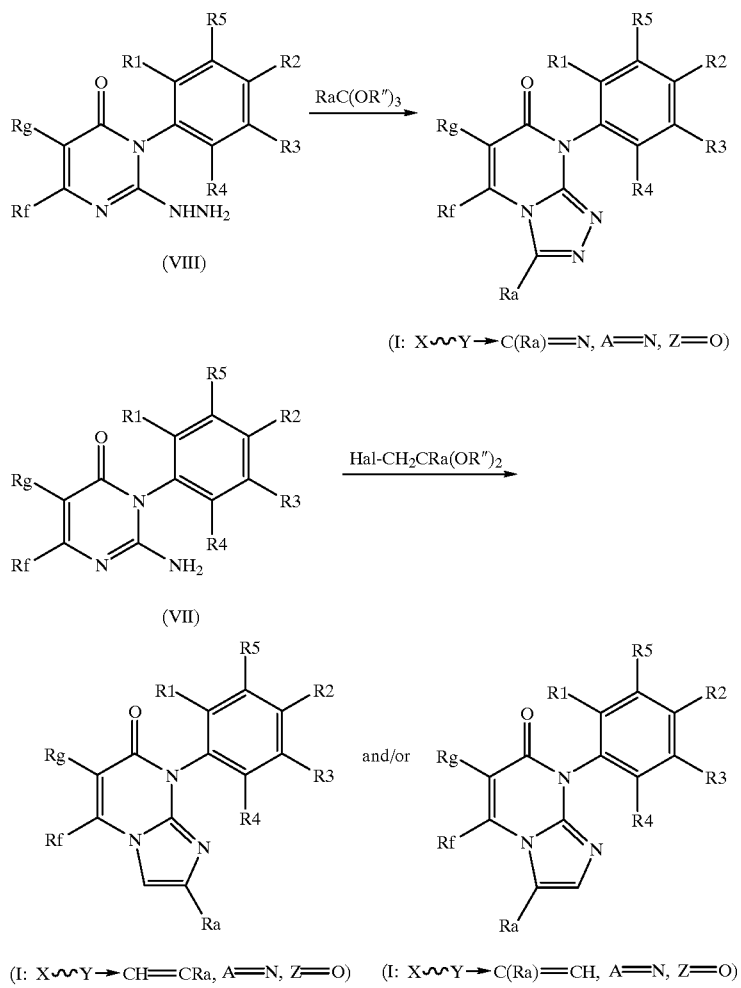
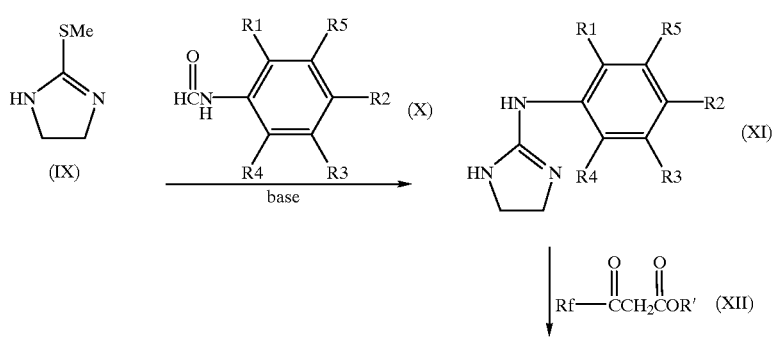

-continued
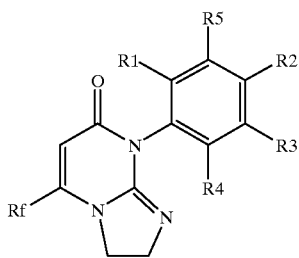
(I: X⁓Y→CH₂CH₂, A═N, Rg═H, Z═O)
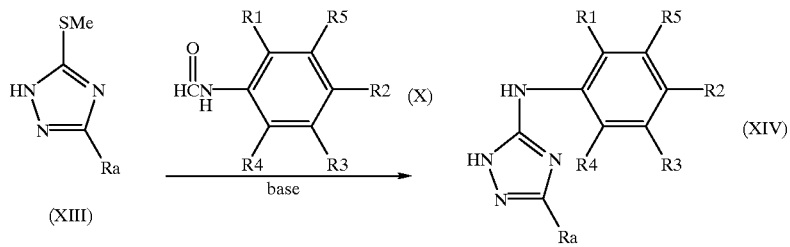
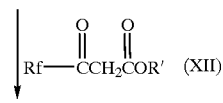
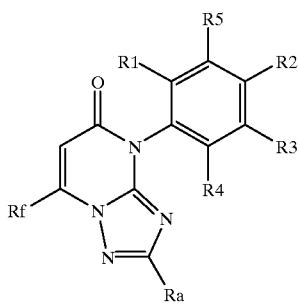
(I: X⁓Y→N═CRa, A═N, Rg═H, Z═O)
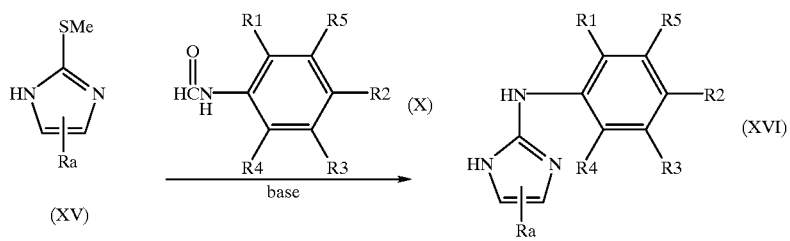

-continued
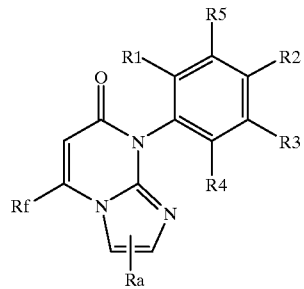
(I: X⌇Y→C(Ra)=CH and/or CH=CRa, A=N, Rg=H, Z=O)
(scheme 4)
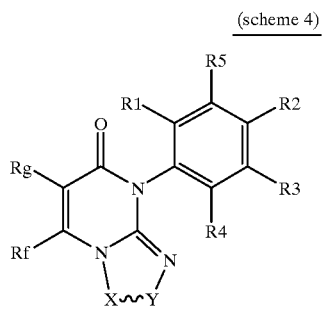
(I: Z=O, A=N, Rg≠CN)
thiocarbonylation
-continued
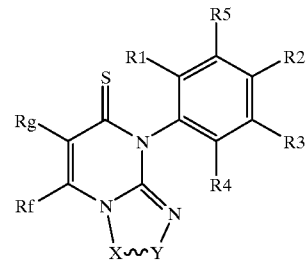
(I: Z=S, A=N, Rg≠CN)
(scheme 5)
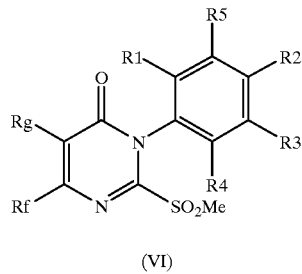  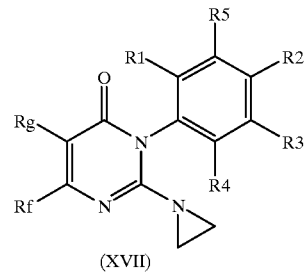
(VI)    (XVII)
↓ KI or NaI
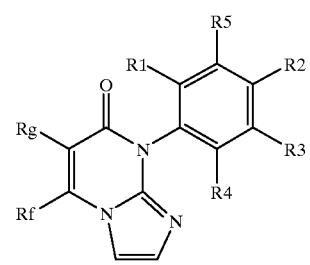 ←oxydizer— 
(I: X⌇Y→CH=CH, A=N, Z=O)   (I: X⌇Y→CH2CH2, A=N, Z=O)

(scheme 6)
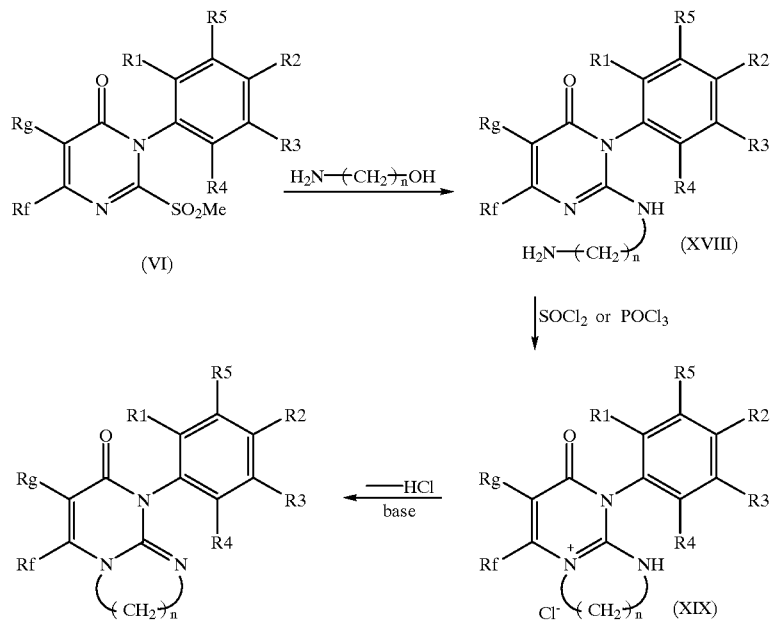
(I: X⌇Y → CH$_2$CH$_2$ or CH$_2$CH$_2$CH$_2$,
A═N, Z═O, n = 2 or 3)
(scheme 7)
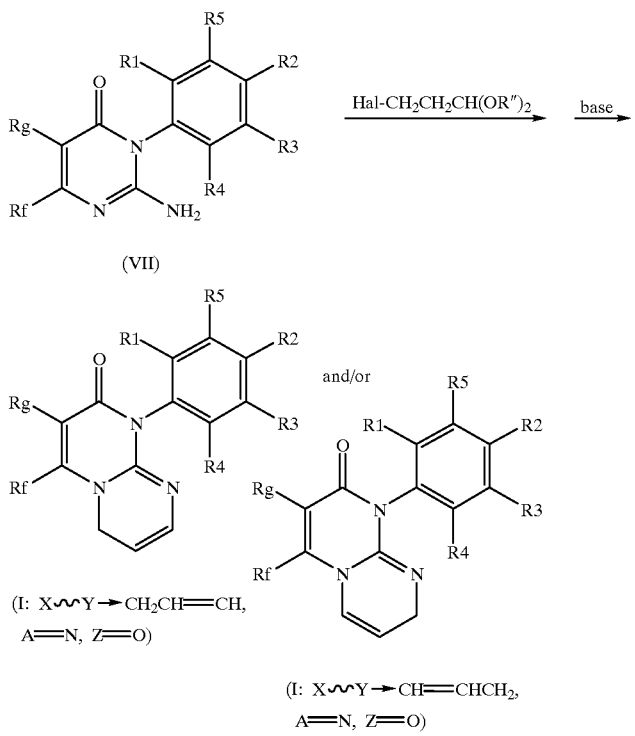
(I: X⌇Y → CH$_2$CH═CH,
A═N, Z═O)
(I: X⌇Y → CH═CHCH$_2$,
A═N, Z═O)

(scheme 8)
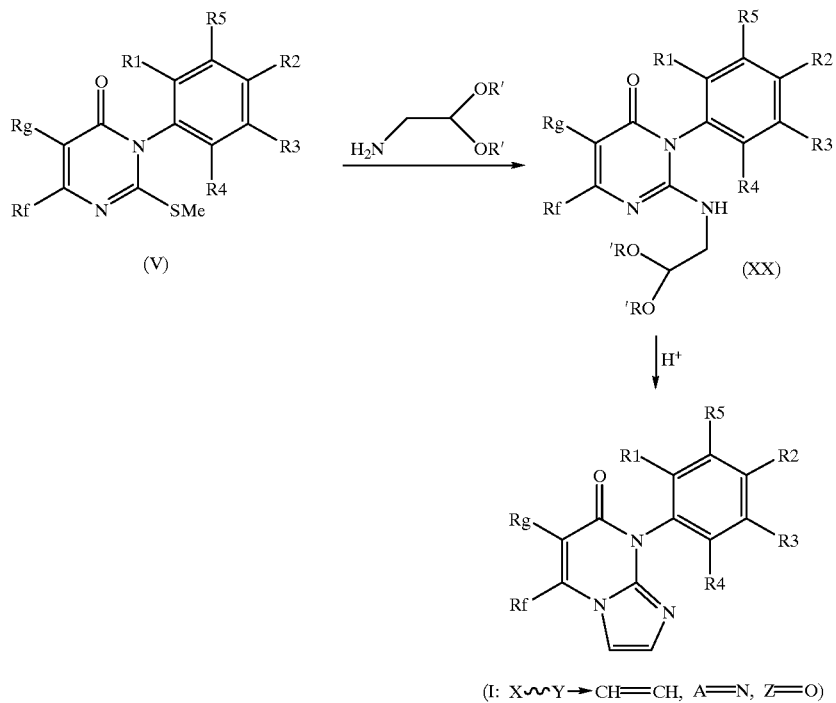
(scheme 9)
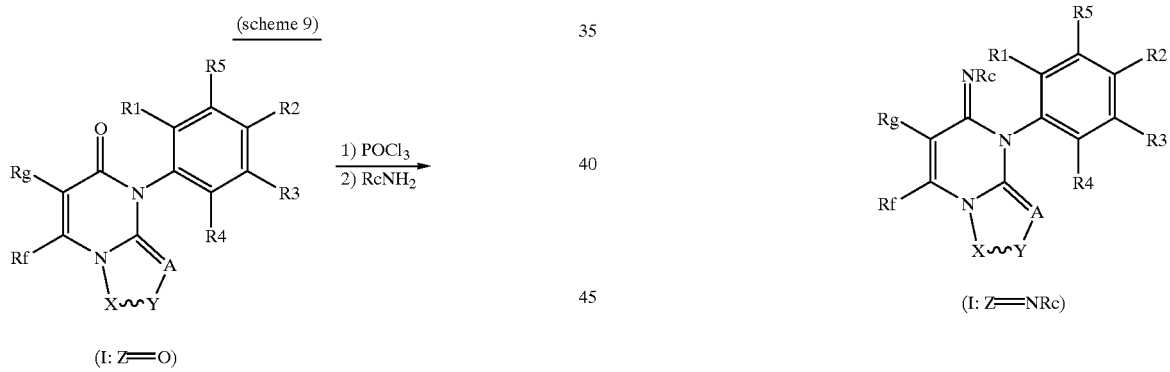

(scheme 10)
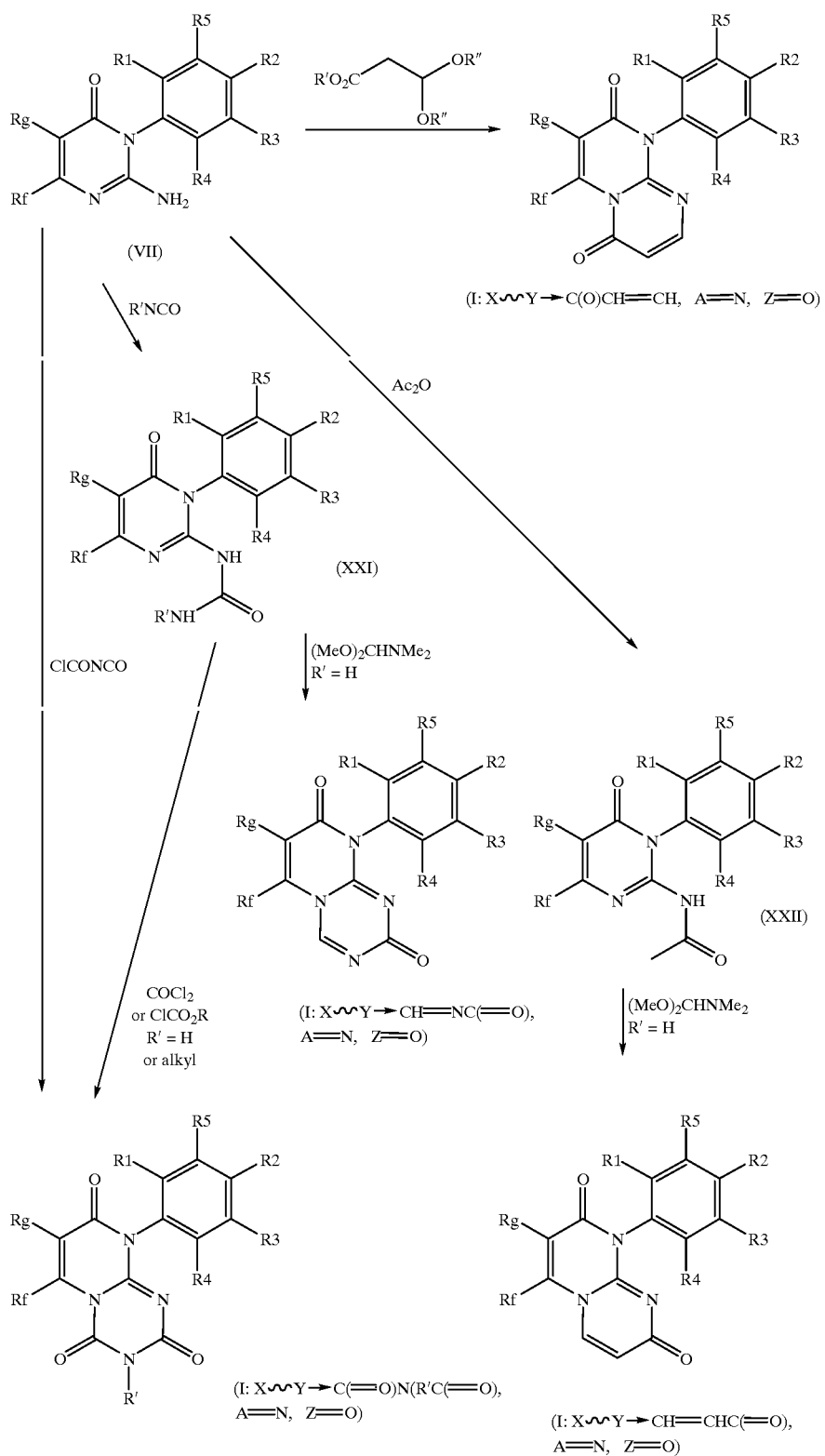

(scheme 11)
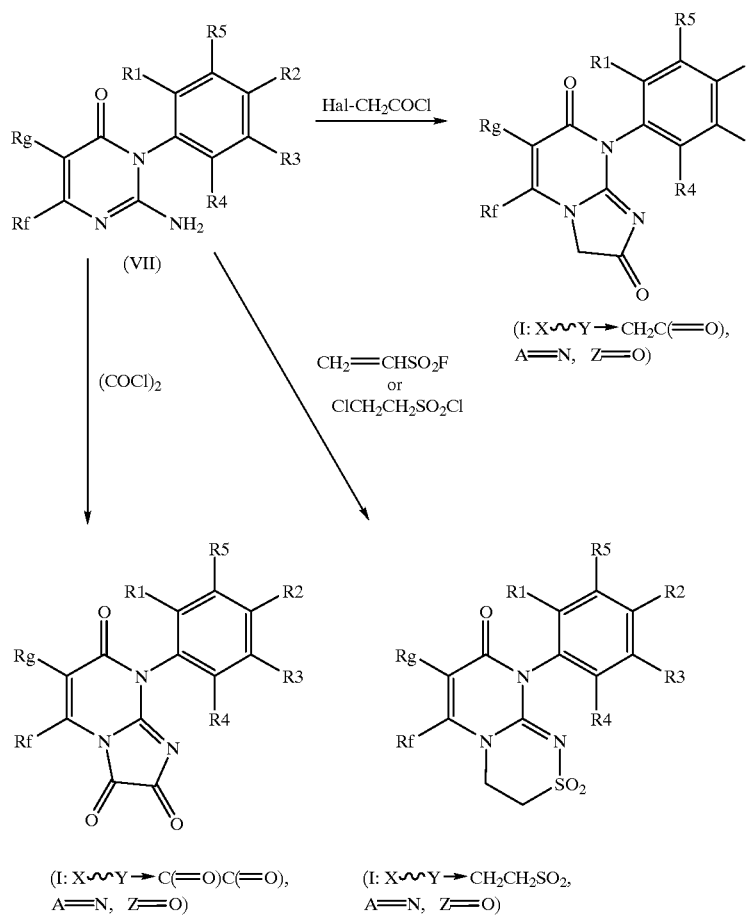
(scheme 12)
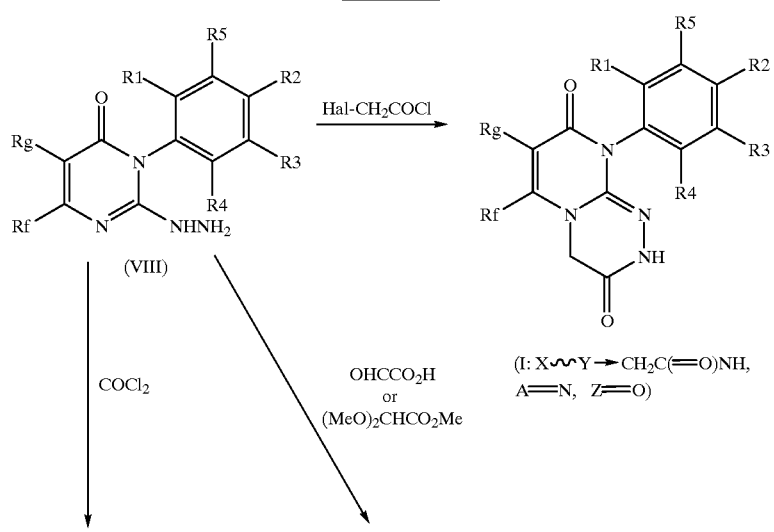

-continued
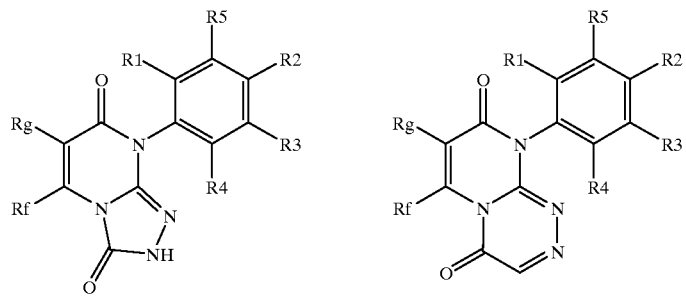
(I: X∼Y→C(=O)NH, A=N, Z=O)
(I: X∼Y→C(=O)CH=N, A=N, Z=O)
(scheme 13)
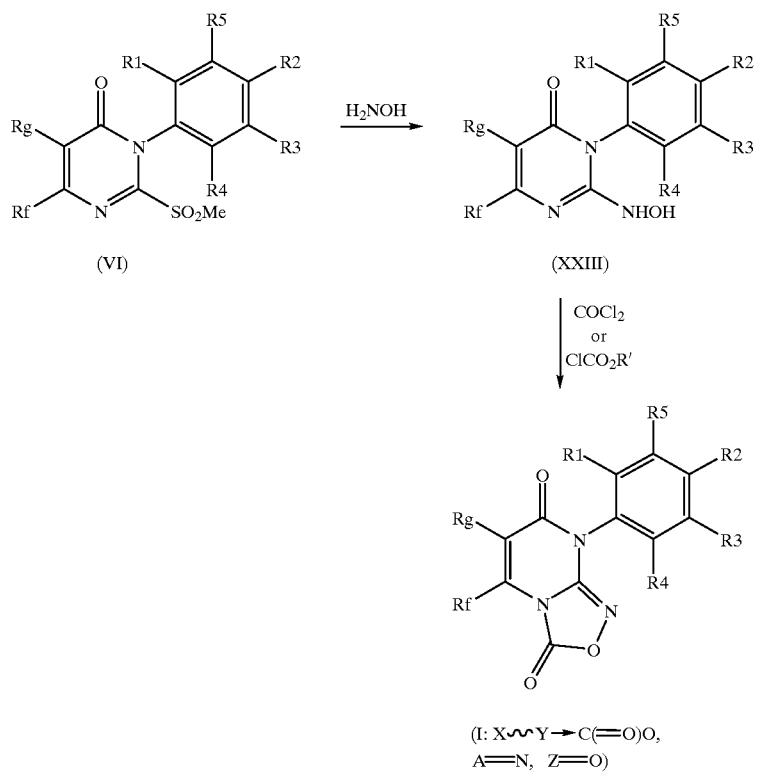
(I: X∼Y→C(=O)O, A=N, Z=O)

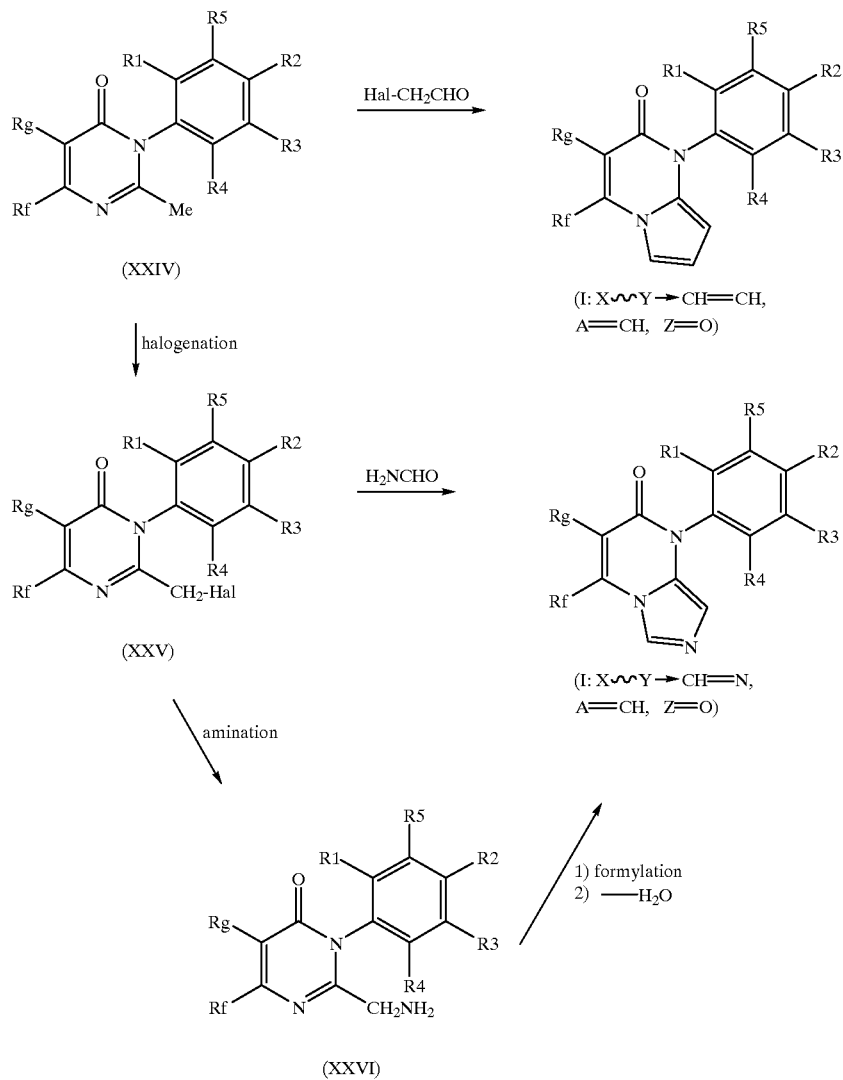
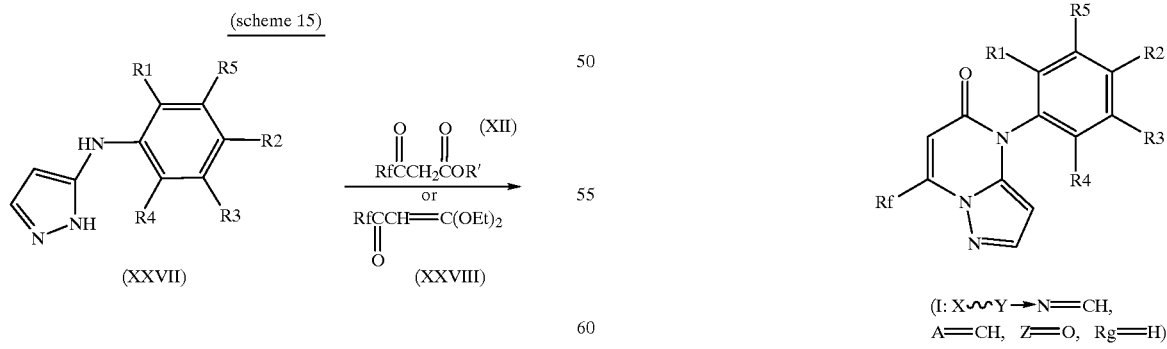

Scheme 1

A 2-mercaptopyrimidine derivative (IV) can be obtained by reacting an aminocrotonic ester derivative (II) with a phenylisothiocyanate derivative (III) in the presence of a base in an inert solvent.

The compound (II) can be synthesized by referring to J. Org. Chem., 21, 1358–61 (1956); J. Heterocycl. Chem., 513 (1972); Zhur. Org. Kim., 22(8), 1603–9 (1986); JP-A-5-140060 and the like. The compound (III) can be prepared from a corresponding aniline derivative according to the process described in Sandler, S. R., Karo, W. "Organic Functional Group Preparations" Academic, New York, 1968, Vol. 1, pp 312–315.

For example, a 2-methylmercaptopyrimidine derivative (V) can be synthesized by reacting the compound (IV) with an alkylating agent (in which Me and Et and the like are preferable as the alkyl) such as, for example dimethylsulfuric acid and methyl iodide, in the presence of a base. The compound (V) can be led to a 2-methanesulfonylpyrimidine derivative (VI) by using an oxidizing agent such as, for example hydrogen peroxide, air and metachloro-perbenzoic acid. The compound of the present invention (I: wherein X~Y is N=N, A is N, and Z is O) can be synthesized by reacting the compound (VI) with sodium azide (potassium azide and trimethylsilyl azide can also be used).

The compound (VI) can be led to a 2-aminopyrimidine derivative (VII) by the reaction with ammonia or ammonium acetate, or to a 2-hydrazinopyrimidine derivative (VIII) by the reaction with hydrazine.

In this connection, when a strong reaction condition is used, the compound (VII), (VIII) or (I: wherein X~Y is N=N, A is N, and Z is O) can be synthesized by using the compound (V) substituted for the compound (VI).

Scheme 2

The compound of the present invention (I: wherein X~Y is C(Ra)=N, A is N, and Z is O) can be synthesized by reacting the compound (VIII) with an orthoester derivative referring to the process described in "Comprehensive Heterocyclic Chemistry" Vol. 5, Part 4A, 890.

The compound of the present invention (I: wherein X~Y is CH=CRa, A is N, and Z is O) or other compound of the present invention (I: wherein X~Y is CRa=CH, A is N, and Z is O) can be synthesized by reacting the compound (VII) with a halogenoacetaldehyde dialkyl acetal derivative (in which a chlorine or bromine atom is preferable as a halogen atom) referring to Chem. Pham. Bull. 40(1) 235–237 (1992).

Scheme 3

Pseudothiourea (IX) and formylaniline (X) are led to a guanidine derivative (XI). Subsequently, the compound of the present invention (I: wherein X~Y is CH$_2$CH$_2$, A is N, Rg is H and Z is O) can be obtained from the compound (XI) together with a β-keto ester derivative (XII) referring to the process described Helvetica Chimica Acta, Vol. 59, Fasc. 4 (1976) pp 1203–1212 and the like.

The compounds (XIV) or (XVI) can be synthesized by reacting 1,2,4-triazole carrying a methylmercapto group (XIII) or imidazole carrying a methylmercapto group (XV) respectively with a formylaniline derivative (X). Subsequently, the compound of the present invention (I: wherein X~Y is N=CRa, A is N, Rg is H, and Z is O) or (I: wherein X~Y is C(Ra)=CH and/or CH=CRa, A is N, Rg is H, and Z is O) can be synthesized by reacting the thus obtained compound (XIV) or (XVI) respectively with a β-keto ester derivative (XII). Optionally, a MeS group of (XIII) and (XV) can be oxidized to a MeSO$_2$ group prior to the reaction.

Scheme 4

The compound of the present invention (I: wherein Z is S, A is N, and Rg is other than CN) can be synthesized by reacting the compound (I: wherein Z is O, A is N, and Rg is other than CN) with a thiocarbonylating agent such as diphosphorus pentasulfide (P$_2$S$_5$) or Lawesson's Reagent (2,4-bis(4-methoxyphenyl)-1,3-dithia-2,4-diphosphetane-2,4-disulfide).

Scheme 5

The compound of the present invention (I: wherein X~Y is CH$_2$CH$_2$, A is N, and Z is O) can be synthesized by reacting the compound (XVII) prepared from the compound (VI) and aziridine, in the presence of sodium iodide or potassium iodide referring to the process of, for example, Org. Chem., Vol. 39, No. 24, 3508 (1974). Subsequently, the compound can be led to the compound of the present invention (I: wherein X~Y is CH=CH, A is N, and Z is O) by using a suitable oxidizing agent such as, for example air, NaOCl, DDQ, potassium permanganate or chloranil.

Scheme 6

Referring to the process described in YAKUGAKU ZASSHI, 94(12) pp 1503–1514 (1974) and the like, the compound (XVIII) prepared from the compound (VI) and aminoalcohol is reacted with thionyl chloride or phosphorus oxychloride to obtain the compound (XIX). This compound can be then react with a base such as DBU, pyridine, KOH or sodium methoxide to obtain the compound of the present invention (I: wherein X~Y is CH$_2$CH$_2$ or CH$_2$CH$_2$CH$_2$, A is N, Z is O, and n is 2 or 3).

In the above reaction, an aminoalcohol carrying on a carbon atom a substituent such as a methyl or phenyl group can be used to introduce the corresponding substituent into a methylene moiety of X~Y of the compound of the present invention.

Scheme 7

The compound of the present invention (I: wherein X~Y is CH$_2$CH=CH, A is N, and Z is O) or (I: wherein X~Y is CH=CHCH$_2$, A is N, and Z is O) can be synthesized by reacting the compound (VII) with halogenopropylaldehyde dialkyl acetal (in which chlorine or bromine is preferable as halogen) followed by the treatment with a base.

Scheme 8

The compound (XX) can be synthesized by reacting the compound (V) with an aminoacetaldehyde dialkyl acetal derivative referring to, for example J. Heterocyclic Chem., 26, 205–207 (1989) to introduce a 2,2-dialkoxyethylamino group into 2-position. Subsequently, the compound (XX) can be subjected to the ring-closing reaction under the acidic condition, for example in the presence of concentrated sulfuric acid, methanesulfonic acid, polyphosphoric acid, concentrated hydrochloric acid or paratoluenesulfonic acid to synthesize the compound of the present invention (I: wherein X~Y is CH=CH, A is N, Z is O).

Scheme 9

The compound (I: wherein Z is O) can be reacted with phosphorus oxychloride followed by the reaction with NH$_2$—Rc referring to, for example EP-168262 to synthesize the compound of the present invention (I: wherein Z is NRc).

Scheme 10

The compound (VII) can be reacted with isocyanic acid salt R'NCO (in which potassium, sodium or ammonium is preferable as R') or alkyl isocyanate R'NCO (R' includes methyl, ethyl and propyl and the like) to synthesize an urea derivative (XXI). The compound (XXI) can be then reacted with dimethylformamide dimethyl acetal to synthesize the compound of the present invention (I: wherein X~Y is CH=NC(=O), A is N, and Z is O).

The compound (XXI) can be reacted with a phosgene derivative such as phosgene, phosgene-dimer or triphosgene, or chloroformate to synthesize the compound of the present invention (I: wherein X~Y is C(=O)N(R')C(=O), A is N, and Z is O).

The compound (VII) can be reacted with a 3,3-dialkoxypropyonic acid derivative to synthesize the compound of the present invention (I: wherein X~Y is C(=O)CH=CH, A is N, and Z is O).

In this connection, the compound (VII) can be reacted with chlorocarbonyl isocyanate referring to, for example Bull. Chem. Soc. Jpn., 61, 2217–2219 (1988) to directly synthesize the compound of the present invention (I: wherein X~Y is C(=O)NHC(=O), A is N, and Z is O).

The compound (VII) can be led to an acetamide derivative (XXII) by the reaction with acetic anhydride or acetyl chloride. The compound (XXII) can be reacted with DMF dimethyl acetal to synthesize the compound of the present invention (I: wherein X~Y is CH=CHC(=O), A is N, and Z is O).

Scheme 11

The compound (VII) can be reacted with chloroacetic acid chloride or bromoacetic acid chloride to synthesize the compound of the present invention (I: wherein X~Y is CH$_2$C(=O), A is N, and Z is O).

The compound (VII) can be reacted with oxalyl chloride to synthesize the compound of the present invention (I: wherein X~Y is C(=O)C(=O), A is N, and Z is O).

The compound (VII) can be reacted with ethenesulfonyl fluoride or chloroethylsulfonyl chloride referring to, for example J. Org. Chem., Vol. 44, No. 22, 3847–3858 (1979) to synthesize the compound of the present invention (I: wherein X~Y is CH$_2$CH$_2$SO$_2$, A is N, and Z is O).

Scheme 12

The compound (VIII) can be reacted with chloroacetic acid chloride or bromoacetic acid chloride to synthesize the compound of the present invention (I: wherein X~Y is CH$_2$C(=O)NH, A is N, and Z is O).

The compound (VIII) can be reacted with glyoxylic acid (which may be also in the form of ester) or glyoxylic acid dimethyl acetal to synthesize the compound of the present invention (I: X~Y is C(=O)CH=N, A is N, and Z is O).

The compound (VIII) can be reacted with a phosgene derivative such as phosgene, phosgene-dimer or triphosgene to synthesize the compound of the present invention (I: wherein X~Y is C(=O)NH, A is N, and Z is O).

Scheme 13

The compound of the present invention (I: wherein X~Y is C(=O)O, A is N, and Z is O) can be synthesized by reacting the compound (VI) with hydroxylamine to obtain the compound (XXIII) which is subsequently reacted with a phosgene derivative such as phosgene, phosgene-dimer or triphosgene, or chloroformate.

Scheme 14

The compound (XXIV) can be reacted with bromoacetaldehyde or chloroacetaldehyde referring to, for example J. Org. Chem., Vol. 42, No. 14, 2448–2454 (1977) to synthesize the compound of the present invention (I: wherein X~Y is CH=CH, A is CH, and Z is O).

The compound of the present invention (I: wherein X~Y is CH=N, A is CH, and Z is O) can be synthesized by reacting the compound (XXIV) with a halogenating agent such as, for example NBS, NCS, chlorine or bromine in the presence of BPO or AIBN to synthesize a halogenomethyl compound (XXV) which is subsequently subjected to cyclodehydration by the reaction with formamide.

Alternatively, the compound of the present invention (I: wherein X~Y is CH=N, A is CH, and Z is O) can be synthesized by introducing an amino group into the compound (XXV) to obtain the compound (XXVI) which is subsequently formylated with formic acid referring to, for example U.S. Pat. No. 4,044,015 followed by drying treatment with phosphorus oxychloride.

Scheme 15

The compound (XXVII) can be reacted with a β-keto ester derivative (XII) or 2,2-ethoxyvinyl haloalkylketone (XXVIII) to synthesize the compound of the present invention (I: wherein X~Y is N=CH, A is CH, Z is O, and Rg is H).

Although the compound (V) or (VI) carrying a methylmercapto or methanesulfonyl group as a leaving group respectively is used in the next reaction in the above Schemes, compounds carrying a chlorine atom as a leaving group can also be used for the reaction.

The following Examples specifically illustrate the process for preparing the compound of the present invention and the intermediate compound. However, it should be recognized that the scope of the present invention is not limited to these Examples.

EXAMPLE 1

Synthesis of 3-(4-chlorophenyl)-3,4-dihydro-2-methanesulfonyl-6-trifluoromethylpyrimidin-4-one

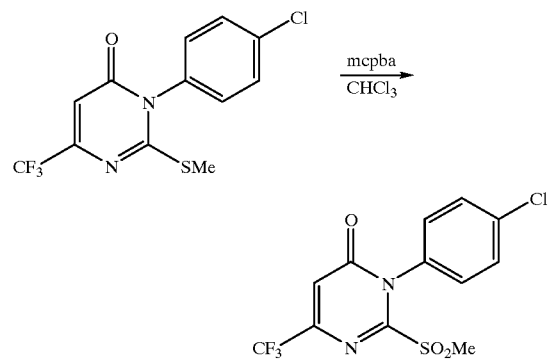

A mixture of 3-(4-chlorophenyl)-3,4-dihydro-2-methylthio-6-trifluoromethylpyrimidin-4-one (1.0 g), 3-chloroperbenzoic acid (1.61 g) and chloroform (20 ml) was stirred for 12 hours at room temperature. The mixture was washed twice with an aqueous saturated sodium hydrogencarbonate solution and once with water and then dried on anhydrous magnesium sulfate. The solvent was distilled off under reduced pressure to give the compound of interest (1.1 g) as a white solid.

EXAMPLE 2

Synthesis of 4-(4-chlorophenyl)-4,5-dihydro-7-trifluoromethyl -tetrazolo[1,5-a]pyrimidin-5-one
(The compound No.1)

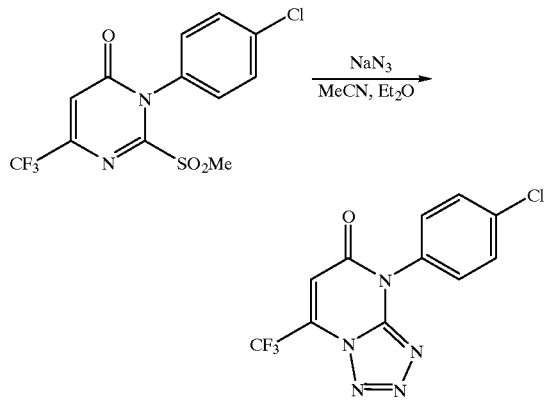

3-(4-Chlorophenyl)-3,4-dihydro-2-methanesulfonyl-6-trifluoromethylpyrimidin-4-one (1.1 g) was dissolved in a mixture of acetonitrile (20 ml) with ether (20 ml) and was added with sodium azide (0.24 g) under ice-cooled condition. The thus obtained mixture was stirred for 30 minutes at room temperature and was added with saturated brine (50 ml). The mixture was extracted with ether and then dried on anhydrous magnesium sulfate followed by distilling off the solvent under reduced pressure. The residue was purified by a preparative thin-layer plate of silica gel (developing solvent: ethyl acetate/hexane=1.5/8.5) to give the compound of interest (0.7 g) as a white solid.

$^1$H-NMR (ppm) 6.67(s, 1H), 7.14(d, J=8.5 Hz, 2H), 7.53(d, J=8.5 Hz, 2H) [CDCl$_3$].

m.p. 81–83° C.

EXAMPLE 3

Synthesis of 3-(4-chlorophenyl)-3,4-dihydro-2-hydrazino-6-trifluoromethylpyrimidin-4-one

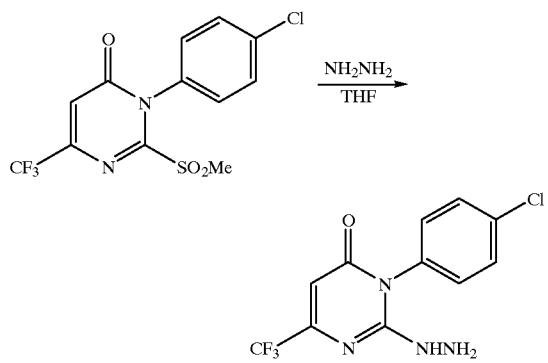

A mixture of 3-(4-chlorophenyl)-3,4-dihydro-2-methanesulfonyl-6-trifluoromethylpyrimidin-4-one (2.0 g) and tetrahydrofuran (20 ml) was added with hydrazine monohydrate (NH$_2$NH$_2$. H$_2$O) (0.5 g). After stirring for 30 minuets at room temperature, the mixture was added with saturated brine (30 ml) and then extracted with ethyl acetate. The extract layer was washed with water and then dried on anhydrous magnesium sulfate. The solvent was distilled off under reduced pressure to give the compound of interest (1.5 g) as a milk white solid.

EXAMPLE 4

Synthesis of 8-(4-chlorophenyl)-7,8-dihydro-5-trifluoromethyl-1,2,4-triazolo[4,3-a]pyrimidin-7-one
(The compound No.2)

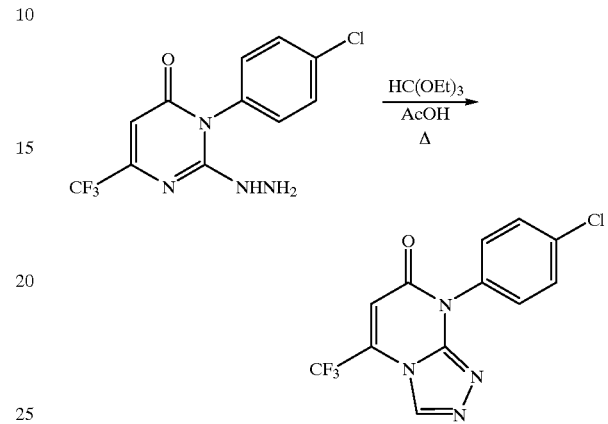

A mixture of 3-(4-chlorophenyl)-3,4-dihydro-2-hydrazino-6 -trifluoromethylpyrimidin-4-one (0.7 g), triethyl orthoformate (1.0 g) and acetic acid (10 ml) was heated for one hour at 120° C. The solvent was distilled off under reduced pressure and the residue was purified by a preparative thin-layer plate of silica gel (developing solvent: ethyl acetate/hexane=4/6) to give the compound of interest (0.45 g).

$^1$H-NMR (ppm) 6.75(s, 1H), 7.37(d, J=9 Hz, 2H), 7.59(d, J=9 Hz, 2H), 8.37–8.48(m, 1H) [CDCl$_3$].

m.p. 220–223° C.

EXAMPLE 5

Synthesis of 2-amino-3-(4-chloro-3-ethoxycarbonylphenyl)-3,4-dihydro-6-trifluoromethylpyrimidin-4-one

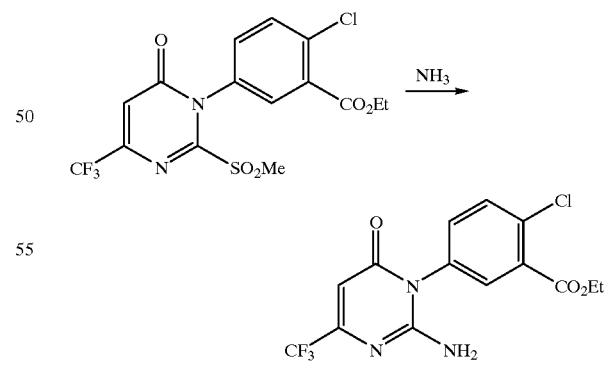

To a mixture of 3-(4-chloro-3-ethoxycarbonylphenyl)-3,4-dihydro-2-methanesulfonyl-6-trifluoromethylpyrimidin-4-one (1.0 g) and dry THF (50 ml) was blown an ammonia gas until the starting material was not found when detected with TLC. The mixture was dried on anhydrous magnesium sulfate and then the solvent was distilled off under reduced pressure. The thus obtained white solid (0.7 g) was used in the next reaction without purifying it.

EXAMPLE 6

Synthesis of 8-(4-chloro-3-methoxycarbonylphenyl)-7,8-dihydro-5-trifluoromethylimidazo[1,2-a]pyrlmidin-7-one (The compound No.4)

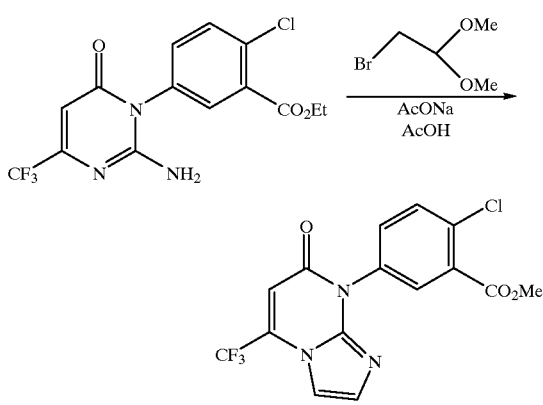

A mixture of 2-amino-3-(4-chloro-3-ethoxycarbonylphenyl)-3,4-dihydro-6-trifluoromethylpyrimidin-4-one (0.7 g), bromoacetaldehyde dimethyl acetal (0.65 g), sodium acetate (0.24 g) and acetic acid (10 ml) was heated to reflux for 4 hours. The solvent was distilled off under reduced pressure, and then the mixture was added with water and extracted with ethyl acetate. The extract layer was washed with water and then dried on anhydrous magnesium sulfate followed by distilling off the solvent under reduced pressure. The residue was purified by a preparative thin-layer plate of alumina (developing solvent: ethyl acetate/hexane=25/75) to give the compound of interest (0.15 g) as a solid.

$^1$H-NMR (ppm) 3.92(s, 3H), 6.72(s, 1H), 7.15(d, J=1.8 Hz, 1H), 7.31(d, J=1.8 Hz, 1H), 7.54–7.68(m, 2H), 7.97–8.04(m, 1H) [CDCl$_3$].

m.p. 180–183° C.

EXAMPLE 7

Synthesis of 8-(4-chloro-2-fluoro-5-nitrophenyl)-7,8-dihydro-5-trifluoromethylimidazo[1,2-a]pyrimidin-7-one (The compound No.7)

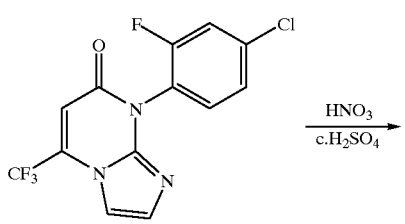

-continued

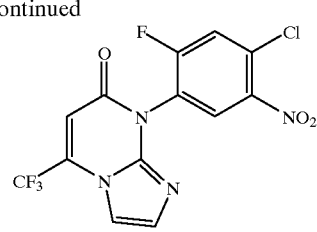

8-(4-Chloro-2-fluorophenyl)-7,8-dihydro-5-trifluoromethylimidazo[1,2-a]pyrimidin-7-one (0.8 g) was added to a mixture of concentrated nitric acid (60%, d=1.38; 1 ml) and concentrated sulfuric acid (10 ml) under ice-cooled condition. The mixture was reacted for 30 minuets at 0° C., poured into ice water (150 ml) and then extracted with ether. The extract layer was washed with water, an aqueous saturated sodium hydrogencarbonate solution and water in this order, and dried on anhydrous magnesium sulfate. The solvent was distilled off under reduced pressure to give the compound of interest (0.65 g) as a solid.

$^1$H-NMR (ppm) 6.64(s, 1H), 7.08(d, J=1.2 Hz, 1H), 7.24(d, J=1.2 Hz, 1H), 7.49(d, J=9 Hz, 1H), 9.16(d, J=6 Hz, 1H) [CDCl$_3$].

m.p. 171–173° C.

EXAMPLE 8

Synthesis of 8-(5-amino-4-chloro-2-fluorophenyl)-7,8-dihydro-5-trifluoromethylimidazo[1,2-a]pyrimidin-7-one (The compound No.8)

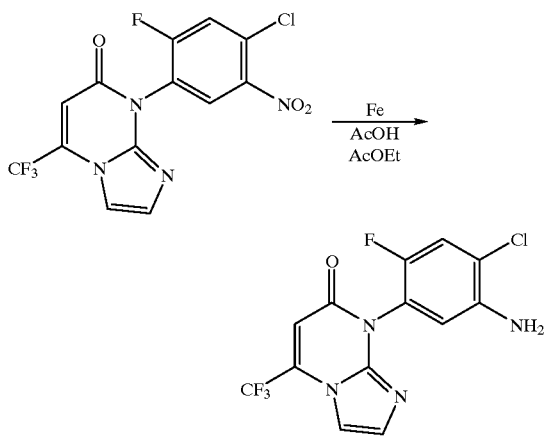

A mixture of 8-(4-chloro-2-fluoro-5-nitrophenyl)-7,8-dihydro-5-trifluoromethylimidazo[1,2-a]pyrimidin-7-one (0.6 g), ethyl acetate (5 ml), acetic acid (2 ml) and water (10 ml) was added with iron powder (0.5 g) and heated to reflux for 3 hours. The mixture was filtered through Celite and the thus obtained solid was washed with hot ethyl acetate. The organic layer was separated from the filtrate and the washing, and dried on anhydrous magnesium sulfate after washing with water. The solvent was distilled off under reduced pressure to give the compound of interest (0.52 g) as a solid.

$^1$H-NMR (ppm) 3.98–4.23(br s, 2H), 6.60(s, 1H), 6.68(d, J=6 Hz, 1H), 7.04–7.28(m, 3H) [CDCl$_3$].

m.p. 184–186° C.

EXAMPLE 9

Synthesis of 8-(4-chloro-5-ethylsulfonylamino-2-fluorophenyl)-7,8-dihydro-5-trifluoromethylimidazo[1,2-a]pyrimidin-7-one (The compound No.6)

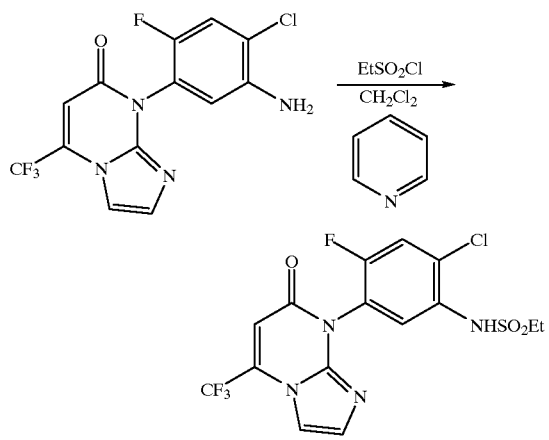

To a mixture of 3-(5-amino-4-chloro-2-fluorophenyl)-7,8-dihydro-5-trifluoromethylimidazo[1,2-a]pyrimidin-7-one (0.49 g) and methylene chloride (15 ml) was added dropwise ethanesulfonyl chloride (0.2 g) and subsequently pyridine (0.17 g). The mixture was stirred for 3 days at room temperature, added with chloroform (50 ml), washed with water, diluted hydrochloric acid and water in this order, and dried on anhydrous sodium sulfate. The solvent was distilled off under reduced pressure and the residue was purified by a preparative thin-layer plate of alumina (developing solvent: ethyl acetate/hexane=1/1) to give the compound of interest (0.08 g) as a solid.

$^1$H-NMR (ppm) 1.35(t, J=7 Hz, 3H), 3.10(q, J=7 Hz, 2H), 6.58(s, 1H), 7.03–7.42(m, 4H), 7.71(d, J=6 Hz, 1H) [CDCl$_3$].

m.p. 226–229° C.

EXAMPLE 10

Synthesis of 8-(4-chloro-3-ethoxycarbonylphenyl)-7,8-dihydro-2-methyl-5-trifluoromethylimidazo[1,2-a]pyrimidin-7-one (The compound No.13)

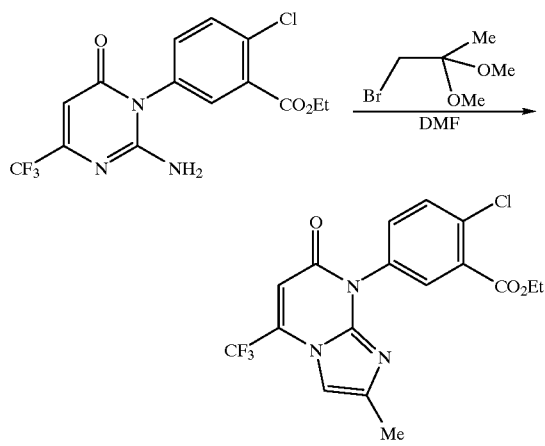

A mixture of 2-amino-3-(4-chloro-3-ethoxycarbonylphenyl)-3,4-dihydro-6-trifluoromethylpyrimidin-4-one (0.5 g), bromoacetone dimethyl acetal (0.6 g) and DMF (10 ml) was heated for 5 hours at 130° C. with stirring. The solvent was distilled off under reduced pressure. The residue was added with water and extracted with ethyl acetate. The extract layer was washed with water and dried on anhydrous magnesium sulfate. The solvent was distilled off under reduced pressure and the residue was purified by a preparative thin-layer plate of alumina (developing solvent: ethyl acetate/hexane=3/7) to give the compound of interest (0.11 g).

$^1$H-NMR (ppm) 1.38(t, J=7 Hz, 3H), 2.22(s, 3H), 4.39(q, J=7 Hz, 2H), 6.62(s, 1H), 7.00(s, 1H), 7.48(dd, J=8, 3 Hz, 1H), 7.64(dd, J=8, 0.5 Hz, 1H), 7.95–7.96(m, 1H) [CDCl$_3$].

m.p. 173–175 C.

EXAMPLE 11

Synthesis of 8-(4-chloro-5-ethylsulfonylamino-2-fluorophenyl)-7,8-dihydro-5-trifluoromethylimidazo[1,2-a]pyrimidine-7-thione (The compound No.20)

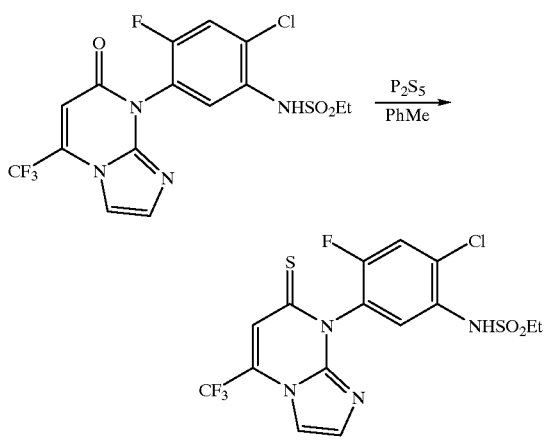

A mixture of 8-(4-chloro-5-ethylsulfonylamino-2-fluorophenyl)-7,8-dihydro-5-trifluoromethylimidazo[1,2-a]pyrimidin-7-one (0.6 g), diphosphorus pentasulfide (0.5 g) and toluene (30 ml) was heated to reflux for 3 hours. The solid matter was filtered off and the filtrate was concentrated under reduced pressure. The residue was purified by column chromatography of silica gel (developing solvent: ethyl acetate) to give the compound of interest (0.5 g) as a yellow crystal.

$^1$H-NMR (ppm) 1.31(t, J=8 Hz, 3H), 3.08(q, J=8 Hz, 2H), 7.14(s, 1H), 7.25–7.70(m, 4H), 9.33–9.42(br s, 1H) [CDCl$_3$+DMSO-d$_6$].

m.p.>220° C. (decomposed).

EXAMPLE 12

Synthesis of 8-(4-chloro-2-fluoro-5-propargyloxyphenyl)-7,8-dihydro-5-trifluoromethylimidazo[1,2-a]pyrimidin-7-one (The compound No.25)

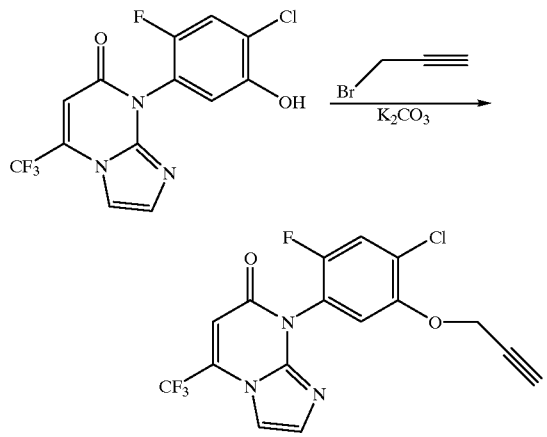

A mixture of 8-(4-chloro-2-fluoro-5-hydroxyphenyl)-7,8-dihydro-5-trifluoromethylimidazo[1,2-a]pyrimidin-7-one (4.3 g), propargyl bromide (2.3 g), potassium carbonate (2.1 g) and acetonitrile (100 ml) was heated to reflux for 2 hours. The solvent was distilled off under reduced pressure. The residue was added with water and extracted with ethyl acetate. The extract layer was washed with water and dried on anhydrous magnesium sulfate. The solvent was distilled off under reduced pressure and the residue was recrystallized from diisopropyl ether to give the compound of interest (4.2 g) as a milk white crystal.

$^1$H-NMR (ppm) 2.46–2.55(m, 1H), 4.67–4.74(m, 2H), 6.71(s, 1H), 7.00–7.22(m, 3H), 7.30(d, J=9 Hz, 1H) [CDCl$_3$].

m.p. 154–156° C.

EXAMPLE 13

Synthesis of 8-(4-cyano-2-fluoro-5-propargyloxyphenyl)-7,8-dihydro-5-trifluoromethylimidazo[1,2-a]pyrimidin-7-one (The compound No.34)

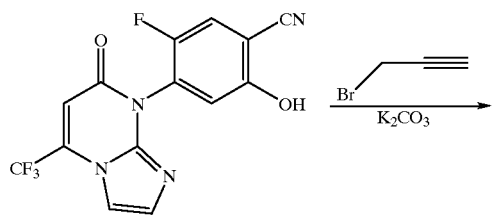

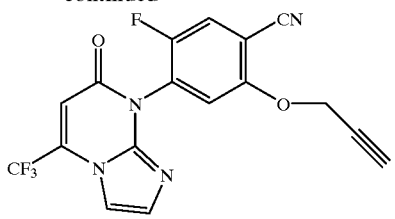

A mixture of 8-(4-cyano-2-fluoro-5-hydroxyphenyl)-7,8-dihydro-5-trifluoromethylimidazo[1,2-a]pyrimidin-7-one (0.23 g), propargyl bromide (0.16 g), potassium carbonate (0.14 g) and acetonitrile (15 ml) was heated to reflux for 2 hours. The solvent was distilled off under reduced pressure. The residue was added with water and extracted with ethyl acetate. The extract layer was washed with water and dried on anhydrous magnesium sulfate. The solvent was distilled off under reduced pressure and the residue was recrystallized from diisopropyl ether to give the compound of interest (0.17 g) as a milk white crystal.

$^1$H-NMR (ppm) 2.52–2.60(m, 1H), 4.75–4.83(m, 2H), 6.65(s, 1H), 7.05–7.27(m, 3H), 7.50(d, J=9 Hz, 1H) [CDCl$_3$].

m.p. 130–132° C.

EXAMPLE 14

Synthesis of 3-(4-bromo-2-fluorophenyl)-3,4-dihydro-2-((2,2-dimethoxyethyl)amino)-6-trifluoromethylpyrimidin-4-one

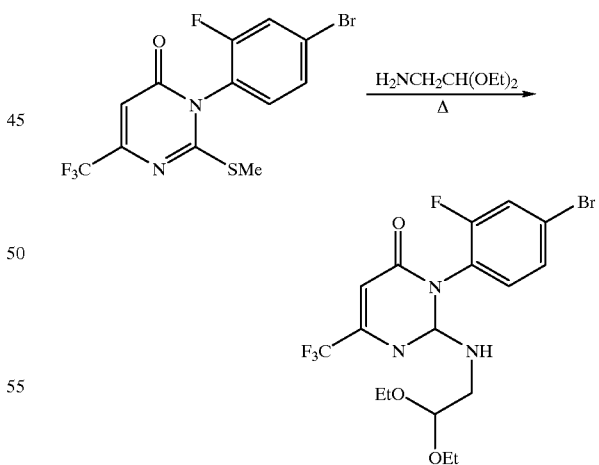

3-(4-Bromo-2-fluorophenyl)-3,4-dihydro-2-methylthio-6-trifluoromethylpyrimidin-4-one (21.5 g) and aminoacetaldehyde diethyl acetal (15 g) were stirred for 3 hours at 130° C. The excess aminoacetaldehyde diethyl acetal was distilled off under reduced pressure and the residue was used in the next reaction as it was.

EXAMPLE 15

Synthesis of 8-(4-bromo-2-fluorophenyl)-7,8-dihydro-5-trifluoromethylimidazo[1,2-a]pyrimidin-7-one (The compound No.69)

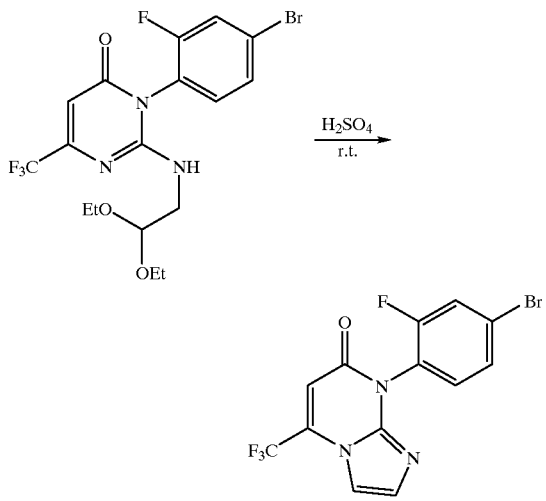

3-(4-Bromo-2-fluorophenyl)-3,4-dihydro-2-((2,2-dimethoxyethyl)amino)-6-trifluoromethylpyrimidin-4-one synthesized in Example 14 was dissolved into concentrated sulfuric acid (100 ml) under ice-cooled condition and stirred for 4 hours at room temperature. The reaction solution was poured into ice water (500 ml), neutralized with an aqueous sodium hydroxide solution under ice-cooled condition, extracted with ethyl acetate and dried on anhydrous magnesium sulfate after washing with water. The solvent was distilled off under reduced pressure and then the thus obtained solid was washed with isopropyl ether to give the compound of interest (17.5 g) as a pale yellow solid.

$^1$H-NMR (ppm) 6.83(s, 1H), 7.24–7.75(m, 5H) [CDCl$_3$].
m.p. 169–171° C.

EXAMPLE 16

Synthesis of 8-(4-bromo-2-fluoro-5-nitrophenyl)-7,8-dihydro-5-trifluoromethylimidazo[1,2-a]pyrimidin-7-one

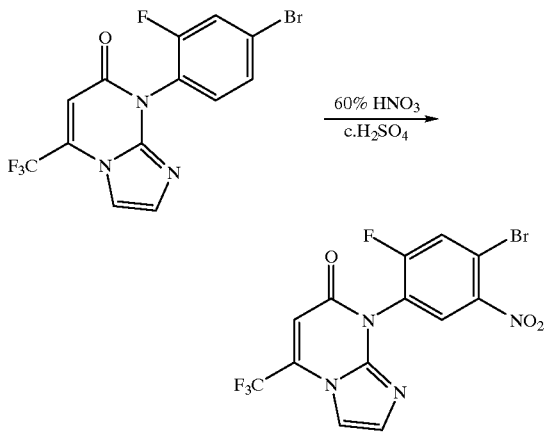

8-(4-Bromo-2-fluorophenyl)-7,8-dihydro-5-trifluoromethylimidazo[1,2-a]pyrimidin-7-one (12 g) was dissolved into concentrated sulfuric acid (50 ml) to which then nitric acid (60%, d=1.38; 5.0 g) was added under ice-cooled condition, and stirred for 2 hours at room temperature. The reaction solution was poured into ice water and the thus obtained solid was filtered off. The solid was washed with water and dried to give the compound of interest (12.5 g).

EXAMPLE 17

Synthesis of 8-(5-amino-4-bromo-2-fluorophenyl)-7,8-dihydro-5-trifluoromethylimidazo[1,2-a]pyrimidin-7-one (The compound No.70)

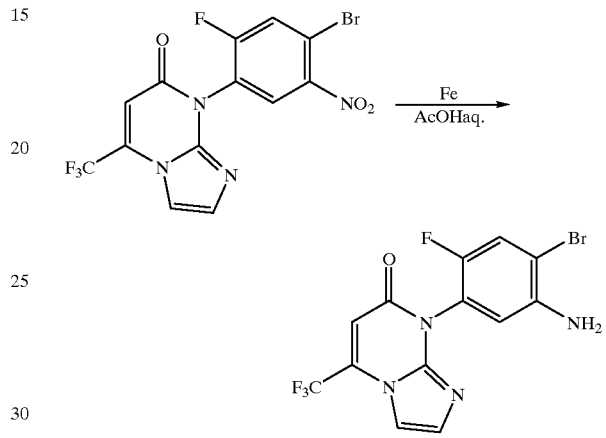

To a mixed solution of water (100 ml), ethyl acetate (50 ml) and acetic acid (50 ml) was added 8-(4-bromo-2-fluoro-5-nitrophenyl)-7,8-dihydro-5-trifluoromethylimidazo[1,2-a]pyrimidin-7-one (12.5 g) synthesized in Example 16 and iron powder (8.0 g) and heated to reflux for 3 hours. The reaction solution was filtered through Celite and then the Celite was washed with heated ethyl acetate. The combined filtrate and washing was washed with water, saturated sodium hydrogencarbonate and water in this order, and dried on anhydrous magnesium sulfate. The solvent was distilled off under reduced pressure after removing a portion adjacent to the original point of the short column of alumina. The thus obtained solid was recrystallized from isopropyl alcohol/isopropyl ether=1/9 to give the compound of interest (9.3 g).

$^1$H-NMR (ppm) 4.07–4.35(br s, 2H), 6.80(s, 1H), 6.82–6.96(m, 1H), 7.23–7.61(m, 3H) [CDCl$_3$].
m.p. 209–210° C.

EXAMPLE 18

Synthesis of 8-(5-amino-4-cysno-2-fluorophenyl)-7,8-dihydro-5-trifluoromethylimidazo[1,2-a]pyrimidin-7-one (The compound No.71)

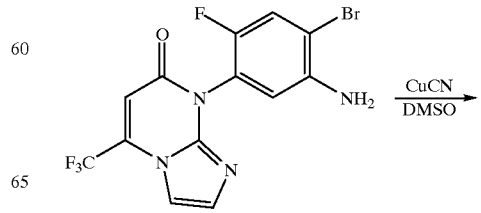

-continued

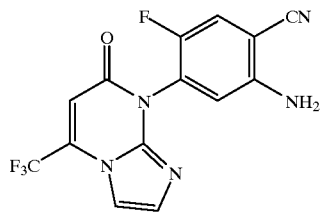

A mixture of 8-(5-amino-4-bromo-2-fluorophenyl)-7,8-dihydro-5-trifluoromethylimidazo[1,2-a]pyrimidin-7-one (3.7 g), copper(I) cyanide (1.1 g) and dimethyl sulfoxide (30 ml) was heated for 5 hours at 170° C. under nitrogen atmosphere with stirring. After cooled to room temperature, the mixture was added with iron chloride (1.0 g) and 6N hydrochloric acid (2 ml), and then stirred for 15 minuets at room temperature. The reaction solution was poured into water (200 ml), extracted with ethyl acetate, washed with water and then dried on anhydrous magnesium sulfate. The solvent was distilled off under reduced pressure and the thus obtained solid was washed with ether to give the compound of interest (2.2 g).

$^1$H-NMR (ppm) 5.30–5.43(br s, 2H), 6.65(s, 1H), 6.73–7.47(m, 4H) [CDCl$_3$].

m.p. 201–203° C.

EXAMPLE 19

Synthesis of 8-(4-bromo-2-fluoro-5-methylsulfonylaminophenyl)-7,8-dihydro-5-trifluoromethylimidazo[1,2-a]pyrimidin-7-one (The compound No.49)

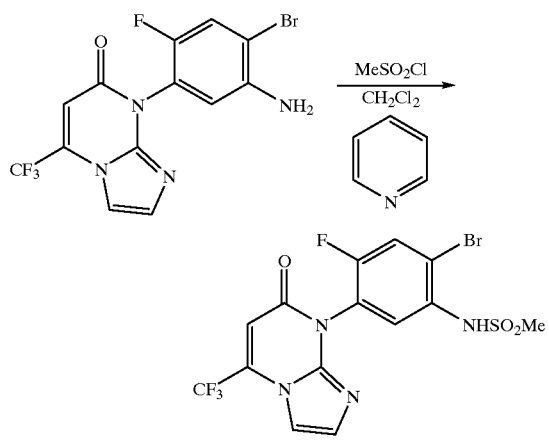

A mixture of 8-(5-amino-4-bromo-2-fluorophenyl)-7,8-dihydro-5-trifluoromethylimidazo[1,2-a]pyrimidin-7-one (5.0 g), methanesulfonyl chloride (1.21 g), pyridine (2.02 g) and methylene chloride (30 ml) was stirred for 5 days at room temperature. The reaction solution was poured into water and extracted with ethyl acetate. The extract layer was washed with water and dried on anhydrous magnesium sulfate followed by distilling off the solvent under reduced pressure. The residual solid was washed with ether to give the compound of interest (4.8 g) as a white solid.

$^1$H-NMR (ppm) 3.04(s, 3H), 6.71(s, 1H), 7.10(s, 1H), 7.26–7.38(m, 1H), 7.56(d, J=6 Hz, 1H), 7.68(d, J=4 Hz, 1H), 9.04–9.13(br s, 1H) [CDCl$_3$+DMSO-d$_6$].

m.p. 238–240° C.

EXAMPLE 20

Synthesis of 8-(4-cyano-2-fluoro-5-methylsulfonylaminophenyl)-7,8-dihydro-5-trifluoromethylimidazo[1,2-a]pyrimidin-7-one (The compound No.51)

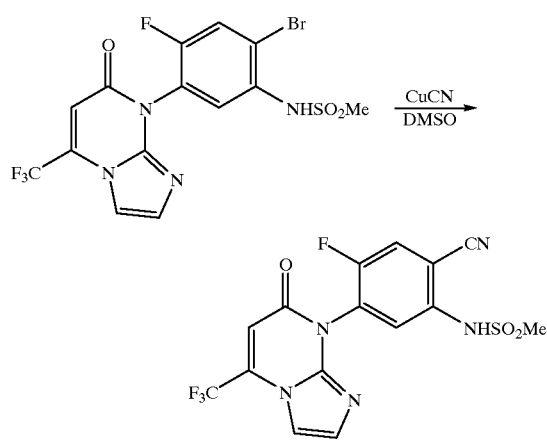

A mixture of 8-(4-bromo-2-fluoro-5-methylsulfonylaminophenyl)-7,8-dihydro-5-trifluoromethylimidazo[1,2-a]pyrimidin-7-one (3.0 g), copper(I) cyanide (0.86 g) and dimethyl sulfoxide (30 ml) was heated for 7 hours at 160° C. under nitrogen atmosphere. After cooled to room temperature, the mixture was added with iron(II) chloride (0.8 g) and 6N hydrochloric acid (1.5 ml), and then stirred for 30 minuets at room temperature. The reaction solution was poured into ice water, and the thus obtained solid was filtered off and washed with ethyl acetate. The solid was dissolved into acetonitrile and then a portion adjacent to the original point of the short column of silica gel was removed. The eluate was concentrated to such an extent that any crystal did not precipitate, added with alumina (5.0 g) for column chromatography and stirred for 15 minuets. The alumina was filtered off, washed with a small amount of acetonitrile and then eluted with an acetonitrile solution (30 ml) containing triethylamine (5%) and water (5%). The eluate was distilled off under reduced pressure and the residue was added with ethyl acetate (10 ml), water (20 ml) and 6N hydrochloric acid (10 drops), followed by stirring vigorously to obtain a solid, which was then filtered off. The thus obtained solid was washed with water and ethyl acetate, and dried to give the compound of interest (0.6 g) as a white solid.

$^1$H-NMR (ppm) 3.06(s, 3H), 6.67(s, 1H), 7.01–7.08(m, 1H), 7.18–7.34(m, 1H), 7.60(d, J=6 Hz, 1H), 7.73(d, J=4 Hz, 1H), 10.08–10.20(br s, 1H) [CDCl$_3$].

m.p.>300° C. (decomposed).

EXAMPLE 21

Synthesis of 8-(4-chloro-5-(2-chloro-2-ethoxycarbonyl)ethyl-2-fluorophenyl)-7,8-dihydro-5-trifluoromethylimidazo[1,2-a]pyrimidin-7-one (The compound No.54)

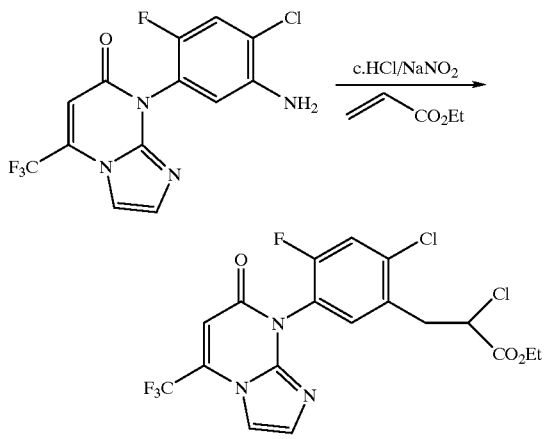

To a mixture of 8-(5-amino-4-chloro-2-fluorophenyl)-7,8-dihydro-5-trifluoromethylimidazo[1,2-a]pyrimidin-7-one (1.5 g), copper(I) chloride (0.06 g) and acetone (30 ml) was added concentrated hydrochloric acid (1.13 g) and ethyl acrylate (5.0 g) under ice-cooled condition. Sodium nitrite (0.38 g) dissolved in water was added slowly under ice-cooled condition to the mixture, which was then stirred for 3 hours at room temperature. The reaction solution was poured into water and extracted with ethyl acetate. The extract layer was washed with diluted hydrochloric acid and water in this order, and dried on anhydrous magnesium sulfate. The solvent was distilled off under reduced pressure and the residue was purified by a preparative thin-layer plate of silica gel (developing solvent: ethyl acetate/hexane=3/7) to give the compound of interest (0.5 g) as a pale yellow oil.

$^1$H-NMR (ppm) 1.24(t, J=6 Hz, 3H), 3.22–3.48(m, 2H), 4.18(q, J=6 Hz, 2H), 4.51(t, J=7 Hz, 1H), 6.60(s, 1H), 6.98–7.39(m, 4H) [CDCl$_3$ ].

$n_D^{20.5}$ 1.5337.

EXAMPLE 22

Synthesis of 2-chloro-8-(4-chloro-2-fluorophenyl)-7,8-dihydro-5-trifluoromethylimidazo[1,2-a] pyrimidin-7-one (The compound No.55)

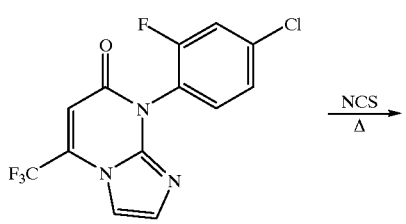

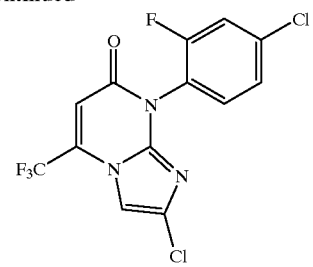

A mixture of 8-(4-chloro-2-fluorophenyl)-7,8-dihydro-5-trifluoromethylimidazo[1,2-a]pyrimidin-7-one (1.0 g), N-chlorosuccinimide (0.4 g) and acetonitrile (30 ml) was heated to reflux for 3 hours. The solvent was distilled off under reduced pressure and the residue was purified by a preparative thin-layer plate of silica gel (developing solvent: ethyl acetate/hexane=2/8) to give the compound of interest (0.3 g).

$^1$H-NMR (ppm) 6.77(s, 1H), 6.97(s, 1H), 7.18–7.42(m, 3H) [CDCl$_3$].

m.p. 157–159° C.

EXAMPLE 23

Synthesis of 8-(2-fluoro-4-((4-methyl-2-(methoxycarbonyl-1-ethyloxy)phenyl)methoxy) phenyl)-7,8-dihydro-5-trifluoromethylimidazo[1,2-a] pyrimidin-7-one (The compound No.62)

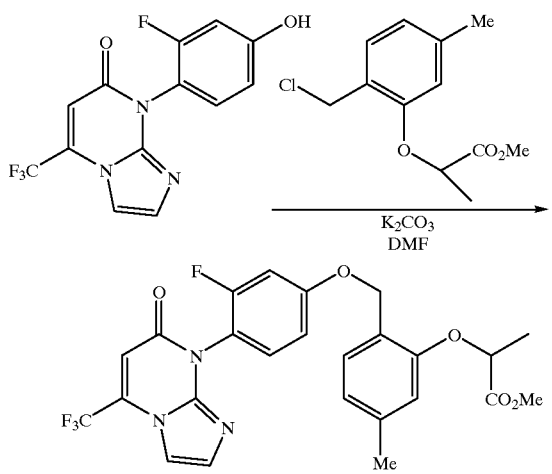

8-(2-Fluoro-4-hydroxyphenyl)-7,8-dihydro-5-trifluoromethylimidazo[1,2-a]pyrimidin-7-one (200 mg) was dissolved into DMF (6 ml), which was then added with potassium carbonate (106 mg) and methyl 2-(2-(chloromethyl)-5-methylphenoxy)propanoate (155 mg), and stirred for 2 hours at 75° C. Subsequently, the mixture was added with water and extracted with diethyl ether. The organic layer was dried on magnesium sulfate followed by distilling off the solvent under reduced pressure. The thus obtained residue was purified by a preparative thin-layer plate of silica gel (developing solvent: ethyl acetate/hexane= 2/3) to give the compound of interest (170 mg).

$^1$H-NMR (ppm) 1.63(d, J=7 Hz, 3H), 2.32(s, 3H), 3.74(s, 3H), 4.85(q, J=7 Hz, 1H), 5.20(s, 2H), 6.51–7.50(m, 9H) [CDCl$_3$].

$n_D^{21.1}$ 1.3912.

The structural formulae and physical properties of the compounds of the present invention synthesized in accordance with the aforementioned Examples including those obtained in the said Examples are listed in Table 1 and Table 2.

[TABLE 1]

| Compound No. | Rf | X~Y | Z | R1 | R2 | R3 | R4 |
|---|---|---|---|---|---|---|---|
| 1 | $CF_3$ | N=N | O | H | Cl | H | H |
| 2 | $CF_3$ | CH=N | O | H | Cl | H | H |
| 3 | $CF_3$ | CH=CH | O | H | Cl | H | H |
| 4 | $CF_3$ | CH=CH | O | H | Cl | $CO_2Me$ | H |
| 5 | $CF_3$ | CH=CH | O | F | Cl | H | H |
| 6 | $CF_3$ | CH=CH | O | F | Cl | $NHSO_2Et$ | H |
| 7 | $CF_3$ | CH=CH | O | F | Cl | $NO_2$ | H |
| 8 | $CF_3$ | CH=CH | O | F | Cl | $NH_2$ | H |
| 9 | $CF_3$ | CH=CH | O | F | Cl | $NHSO_2Me$ | H |
| 10 | $CF_3$ | CH=CH | O | F | Cl | $NHCO_2Me$ | H |
| 11 | $CF_3$ | CH=CH | O | H | Cl | $CO_2Et$ | H |
| 12 | $CF_3$ | CH=CH | O | F | —$OCH_2CON(CH_2C\equiv CH)$— | | H |
| 13 | $CF_3$ | CH=CMe | O | H | Cl | $CO_2Et$ | H |
| 14 | $CF_3$ | CH=CH | O | F | Cl | $N(CHO)CH_2CO_2Me$ | H |
| 15 | $CF_3$ | CH=CH | O | F | Cl | $N(CHO)CH(Me)CO_2Et$ | H |
| 16 | $CF_3$ | CH=CH | O | F | Cl | $NHSO_2Pr$ | H |
| 17 | $CF_3$ | CH=CH | O | F | Cl | $NHSO_2Bu$ | H |
| 18 | $CF_3$ | CH=CH | O | F | Cl | O-cyclo-Pn | H |
| 19 | $CF_3$ | CH=CH | O | H | Cl | $CO_2$-iso-Pr | H |
| 20 | $CF_3$ | CH=CH | S | F | Cl | $NHSO_2Et$ | H |
| 21 | $CF_3$ | CH=CH | O | F | Cl | OMe | H |
| 22 | $CF_3$ | CH=CH | O | F | Cl | OH | H |
| 23 | $CF_3$ | CH=CH | O | F | Cl | $OCH_2CO_2Et$ | H |
| 24 | $CF_3$ | CH=CH | O | F | Cl | $N(pyvaloyl)SO_2Et$ | H |
| 25 | $CF_3$ | CH=CH | O | F | Cl | $OCH_2C\equiv CH$ | H |
| 26 | $CF_3$ | CH=CH | O | F | Cl | O-iso-Pr | H |
| 27 | $CF_3$ | CH=CH | O | F | Cl | $OCH(Me)CO_2Et$ | H |
| 28 | $CF_3$ | CH=CH | O | F | Cl | $N(4-methoxybenzoyl)SO_2Et$ | H |
| 29 | $CF_3$ | CH=CH | O | F | Cl | $N(4-methoxybenzoyl)SO_2Me$ | H |
| 30 | $CF_3$ | CH=CH | O | F | Cl | $N(pyvaloyl)SO_2Me$ | H |
| 31 | $CF_3$ | CH=CH | O | F | Cl | $OCH(Me)C\equiv CH$ | H |
| 32 | $CF_3$ | CH=CH | O | F | Cl | Me | H |
| 33 | $CF_3$ | CH=CH | O | F | Cl | $OCH_2CO_2Me$ | H |
| 34 | $CF_3$ | CH=CH | O | F | $C\equiv N$ | $OCH_2C\equiv CH$ | H |
| 35 | $CF_3$ | CH=CH | O | F | $C\equiv N$ | OMe | H |
| 36 | $CF_3$ | CH=CH | O | F | $C\equiv N$ | $OCH_2Ph$ | H |
| 37 | $CF_3$ | CH=CH | O | F | Cl | $OCH_2C\equiv CH$ | Q 1 |
| 38 | $CF_3$ | CH=CH | O | F | $C\equiv N$ | $OCH_2CO_2C_2H_5$ | H |
| 39 | $CF_3$ | CH=CH | O | F | $C\equiv N$ | O-cyclo-Pn | H |
| 40 | $CF_3$ | CH=CH | O | F | $C\equiv N$ | O-iso-Pr | H |
| 41 | $CF_3$ | CH=CH | O | F | $C\equiv N$ | $OCO_2CH_3$ | H |
| 42 | $CF_3$ | CH=CH | O | F | Br | $OCH_2C\equiv CH$ | H |
| 43 | $CF_3$ | CH=CH | O | F | Br | OMe | H |
| 44 | $CF_3$ | CH=CH | O | F | $C\equiv N$ | $OCH_2CO_2Pn$ | H |
| 45 | $CF_3$ | CH=CH | O | F | $C\equiv N$ | $OCH_2C\equiv N$ | H |
| 46 | $CF_3$ | CH=CH | O | F | Br | $NHSO_2C_2H_5$ | H |
| 47 | $CF_3$ | CH=CH | O | F | Br | O-iso-Pr | H |
| 48 | $CF_3$ | CH=CH | O | F | Br | O-cyclo-Pn | H |
| 49 | $CF_3$ | CH=CH | O | F | Br | $NHSO_2Me$ | H |
| 50 | $CF_3$ | CH=CH | O | F | $C\equiv N$ | $NHSO_2Et$ | H |
| 51 | $CF_3$ | CH=CH | O | F | $C\equiv N$ | $NHSO_2Me$ | H |
| 52 | $CF_3$ | CH=CH | O | Cl | Cl | OMe | H |
| 53 | $CF_3$ | CH=N | O | F | Br | OMe | H |
| 54 | $CF_3$ | CH=CH | O | F | Cl | $CH_2CH(Cl)CO_2C_2H_5$ | H |
| 55 | $CF_3$ | CH=CCl | O | F | Cl | H | H |
| 56 | $CF_3$ | CH=CBr | O | F | Cl | Me | H |
| 57 | $CF_3$ | CH=CH | O | Cl | Cl | $OCH_2C\equiv CH$ | H |
| 58 | $CF_3$ | CH=CH | O | Cl | Cl | O-iso-Pr | H |
| 59 | $CF_3$ | CH=CH | O | Cl | Cl | Ocyclo-Pn | H |
| 60 | $CF_3$ | CH=CH | O | F | $C\equiv N$ | $NHCOCF_3$ | H |

[TABLE 1]-continued

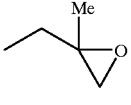

| Compound No. | Rf | X~Y | Z | R1 | R2 | R3 | R4 |
|---|---|---|---|---|---|---|---|
| 61 | CF₃ | CH=CH | O | F | OMe | H | H |
| 62 | CF₃ | CH=CH | O | F | Q 2 | H | H |
| 63 | CF₃ | CH=CH | O | F | Q 3 | H | H |
| 64 | CF₃ | CH=CH | O | F | Cl | NHCH₂C≡CH | H |
| 65 | CF₃ | CH=CH | O | F | Cl | N(SO₂Me)CH₂C≡CH | H |
| 66 | CF₃ | CH=CH | O | F | Q 4 | H | H |
| 67 | CF₃ | CH=CH | O | F | Br | Q 2 | H |
| 68 | CF₃ | CH=CH | O | F | Br | OCH₂CH=CH₂ | H |
| 69 | CF₃ | CH=CH | O | F | Br | H | H |
| 70 | CF₃ | CH=CH | O | F | Br | NH₂ | H |
| 71 | CF₃ | CH=CH | O | F | C≡N | NH₂ | H |
| 72 | CF₃ | CH=CH | O | F | OCF₂H | H | H |
| 73 | CF₃ | CH=CH | O | F | C≡CSiMe₃ | H | H |

Provided that in the above table Q1~Q4 represent the following substituents.

Q1

Q2

Q3

Q4

TABLE 2

| Compound No. | Physical property |
|---|---|
| 1 | mp 81–83° C. |
| 2 | mp 220–223° C. |
| 3 | mp 213–216° C. |
| 4 | mp 180–183° C. |
| 5 | mp 165–168° C. |
| 6 | mp 226–229° C. |
| 7 | mp 171–173° C. |

TABLE 2-continued

| Compound No. | Physical property |
|---|---|
| 8 | mp 184–186° C. |
| 9 | mp 240–243° C. |
| 10 | mp 181–183° C. |
| 11 | mp 126–128° C. |
| 12 | mp 239–241° C. |
| 13 | mp 173–175° C. |
| 14 | mp 72–74° C. |
| 15 | mp 53–55° C. |
| 16 | mp 205–208° C. |
| 17 | mp 180–183° C. |
| 18 | mp 157–159° C. |
| 19 | mp 133–135° C. |
| 20 | mp >220° C. (decomposed) |
| 21 | mp 145–147° C. |
| 22 | mp 255–257° C. |
| 23 | mp 110–112° C. |
| 24 | mp 175–178° C. |
| 25 | mp 154–156° C. |
| 26 | mp 144–146° C. |
| 27 | $n_D^{20.5}$ 1.5248 |
| 28 | mp 72–75° C. |
| 29 | mp 90–93° C. |
| 30 | mp 209–212° C. |
| 31 | mp 121–123° C. |
| 32 | mp 120–122° C. |
| 33 | mp 127–129° C. |
| 34 | mp 130–132° C. |
| 35 | mp 200–202° C. |
| 36 | mp 163–165° C. |
| 37 | $n_D^{21.7}$ 1.5280 |
| 38 | mp 143–145° C. |
| 39 | mp 144–146° C. |
| 40 | mp 79–81° C. |
| 41 | mp 170–172° C. |
| 42 | mp 127–129° C. |
| 43 | mp 142–143° C. |
| 44 | mp 132–134° C. |
| 45 | mp 218–220° C. |
| 46 | mp 210–212° C. |
| 47 | mp 101–103° C. |
| 48 | mp 172–174° C. |
| 49 | mp 238–240° C. |
| 50 | mp 235–238° C. |

TABLE 2-continued

| Compound No. | Physical property |
|---|---|
| 51 | mp >300° C. (decomposed) |
| 52 | mp 72–75° C. |
| 53 | mp 250–252° C. |
| 54 | $n_D^{20.5}$ 1.5337 |
| 55 | mp 157–159° C. |
| 56 | mp 135–137° C. |
| 57 | $n_D^{20.6}$ 1.5624 |
| 58 | mp 139–141° C. |
| 59 | mp 133–135° C. |
| 60 | mp 208–210° C. |
| 61 | $n_D^{21.1}$ 1.5074 |
| 62 | $n_D^{21.1}$ 1.3912 |
| 63 | mp 110–113° C. |
| 64 | mp 202–205° C. |
| 65 | mp 89–91° C. |
| 66 | mp 142–144° C. |
| 67 | mp 57–60° C. |

TABLE 2-continued

| Compound No. | Physical property |
|---|---|
| 68 | mp 60–63° C. |
| 69 | mp 169–171° C. |
| 70 | mp 209–210° C. |
| 71 | mp 201–203° C. |
| 72 | mp 118–120° C. |
| 73 | mp 170–172° C. |

The compounds of the present invention synthesized in accordance with the aforementioned Schemes or Examples including those obtained in the said Examples are listed in Table 3 and Table 4. Those compounds, however, should not limit the present invention.

TABLE 3

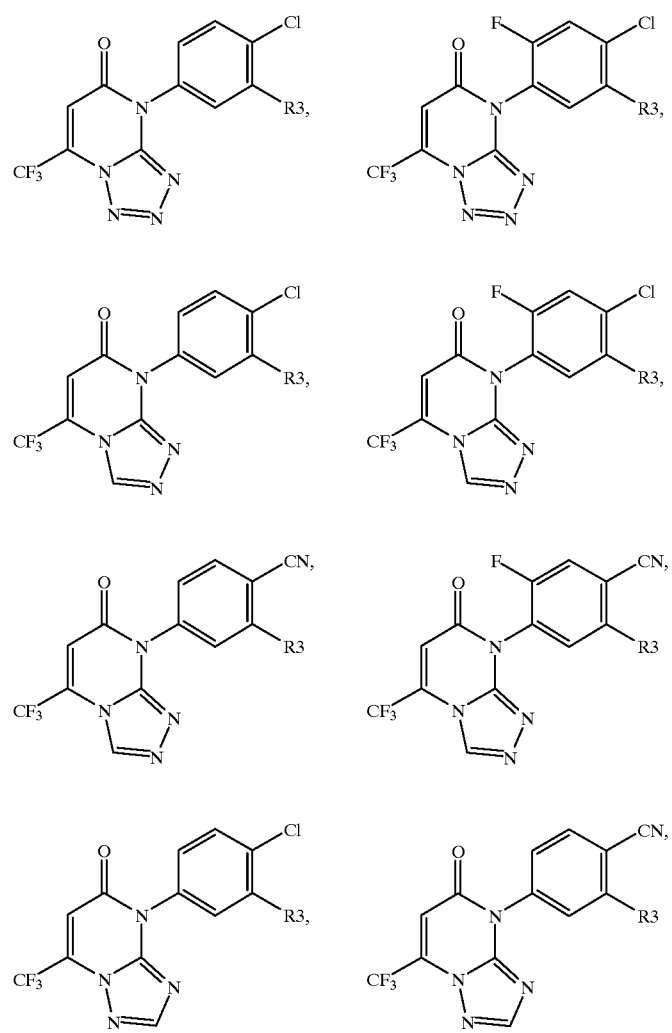

TABLE 3-continued
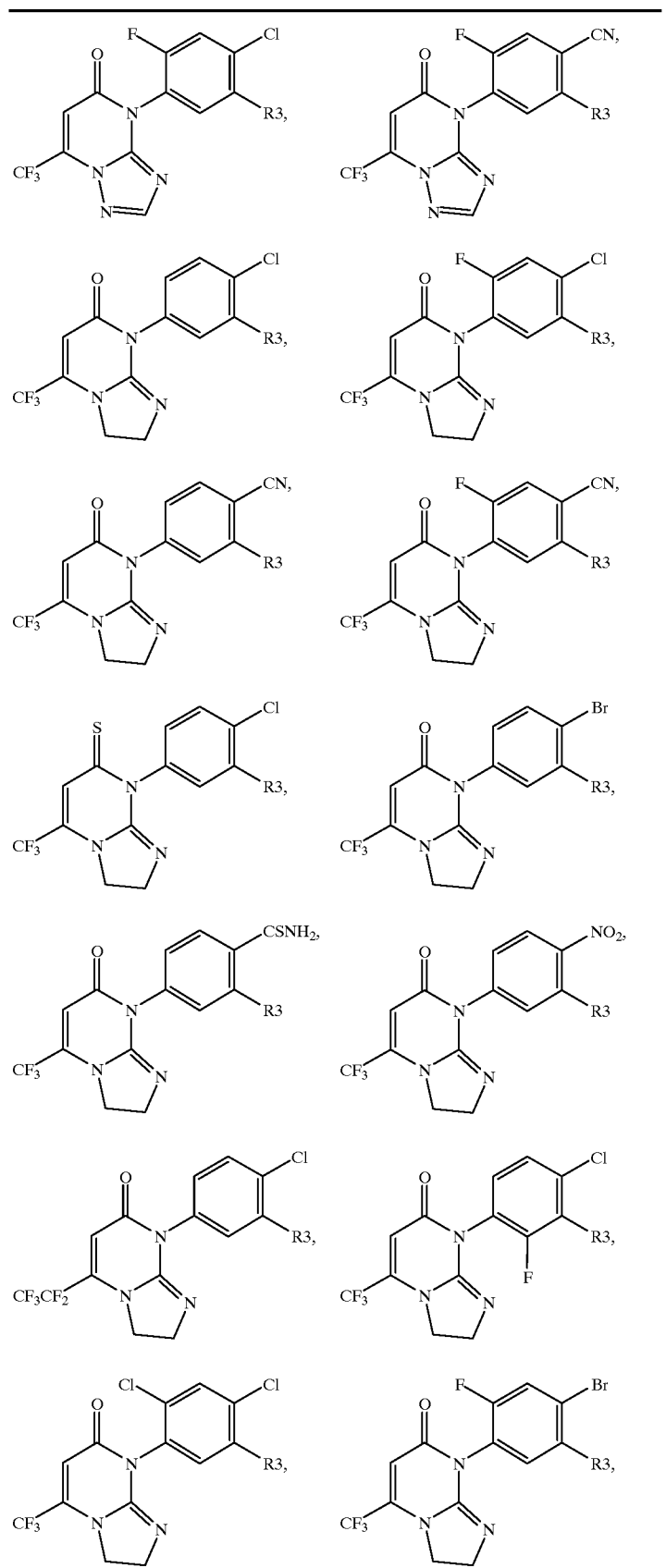

TABLE 3-continued
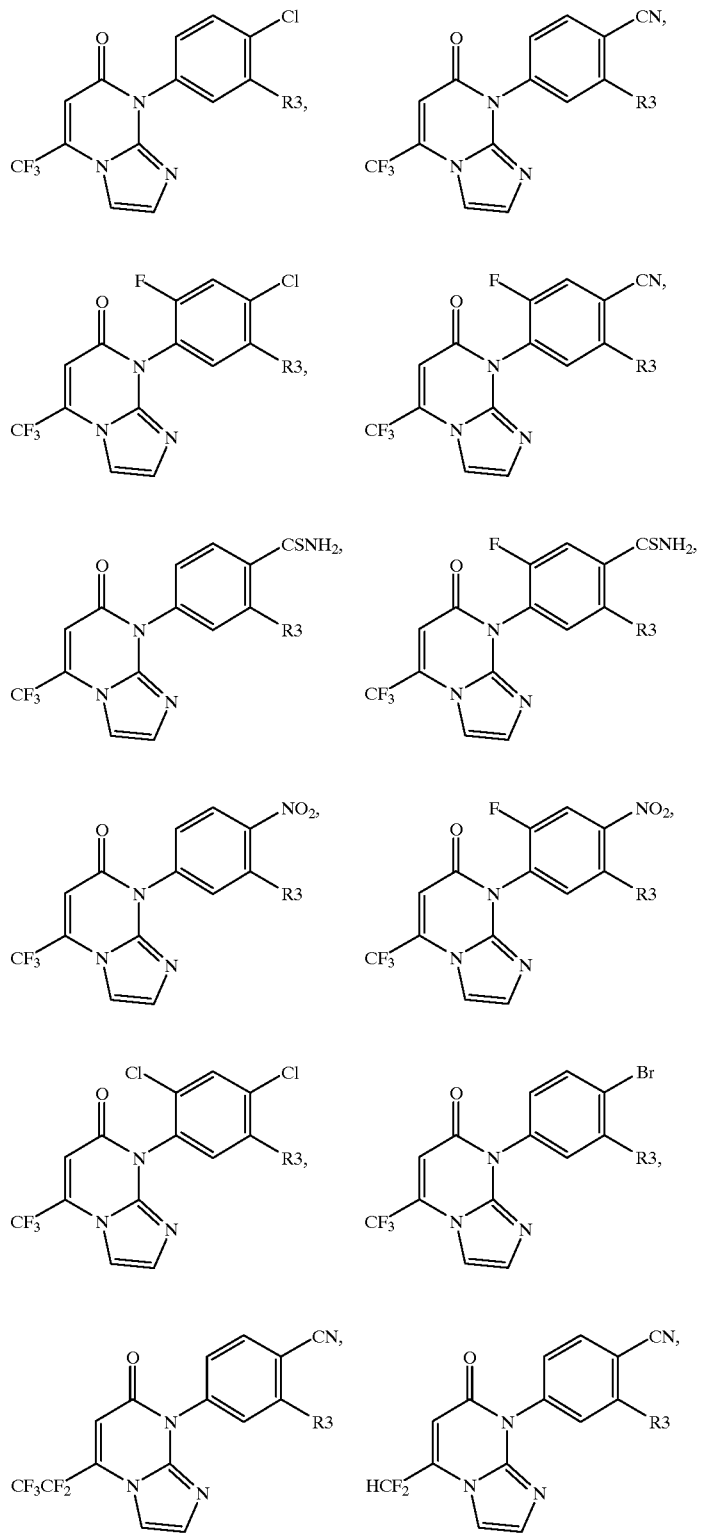

TABLE 3-continued
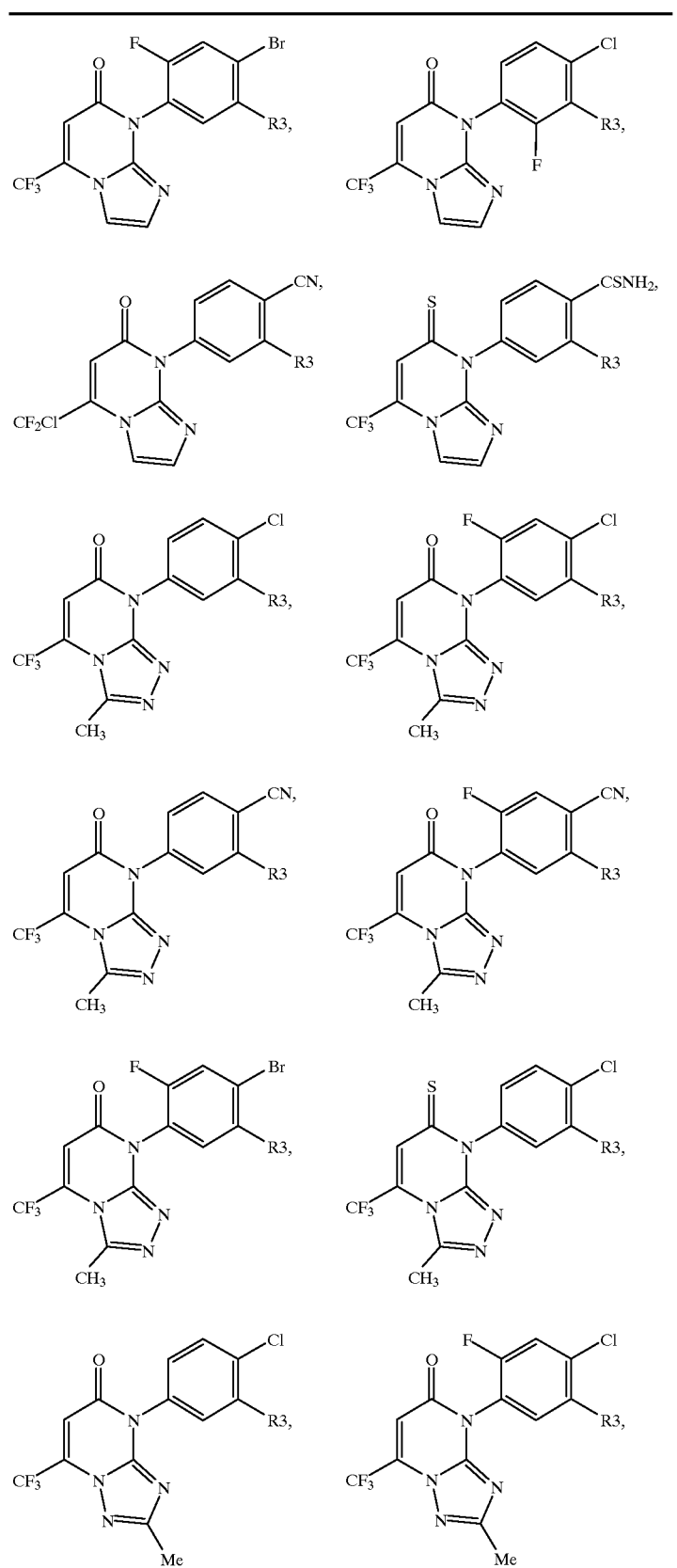

TABLE 3-continued
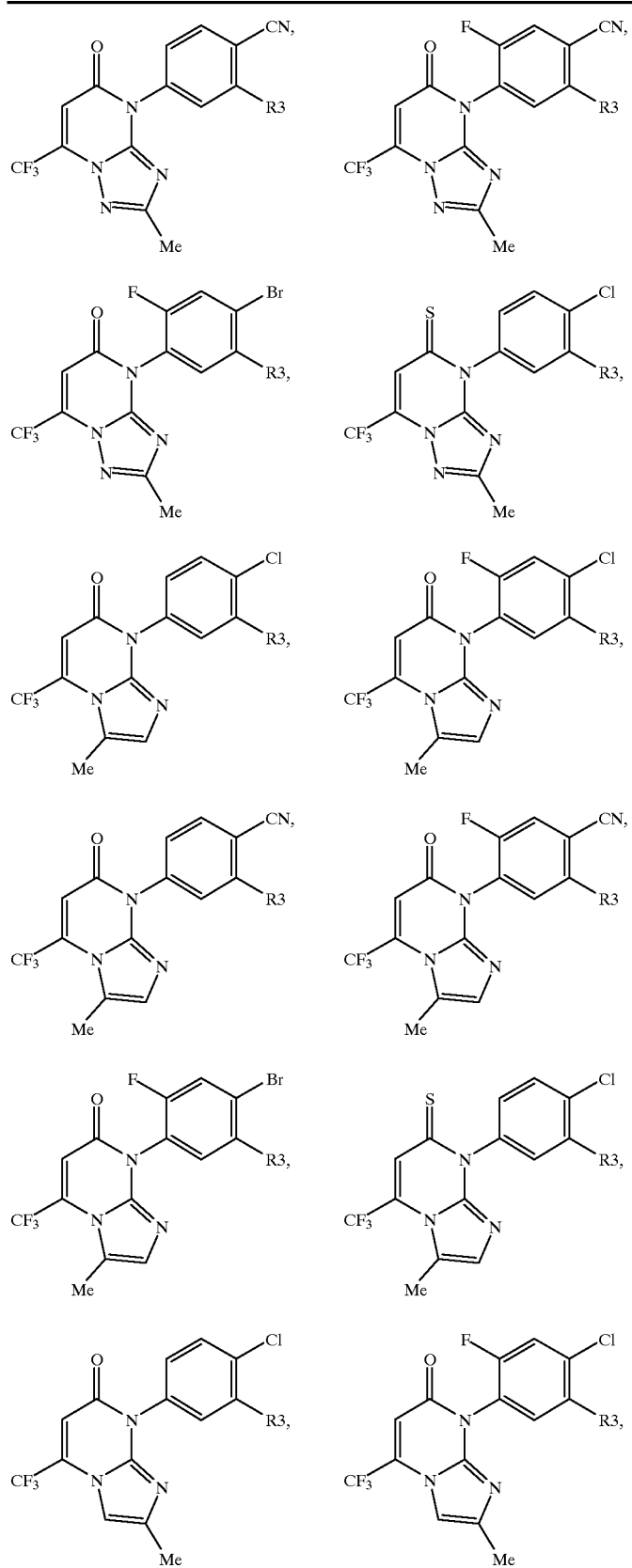

TABLE 3-continued
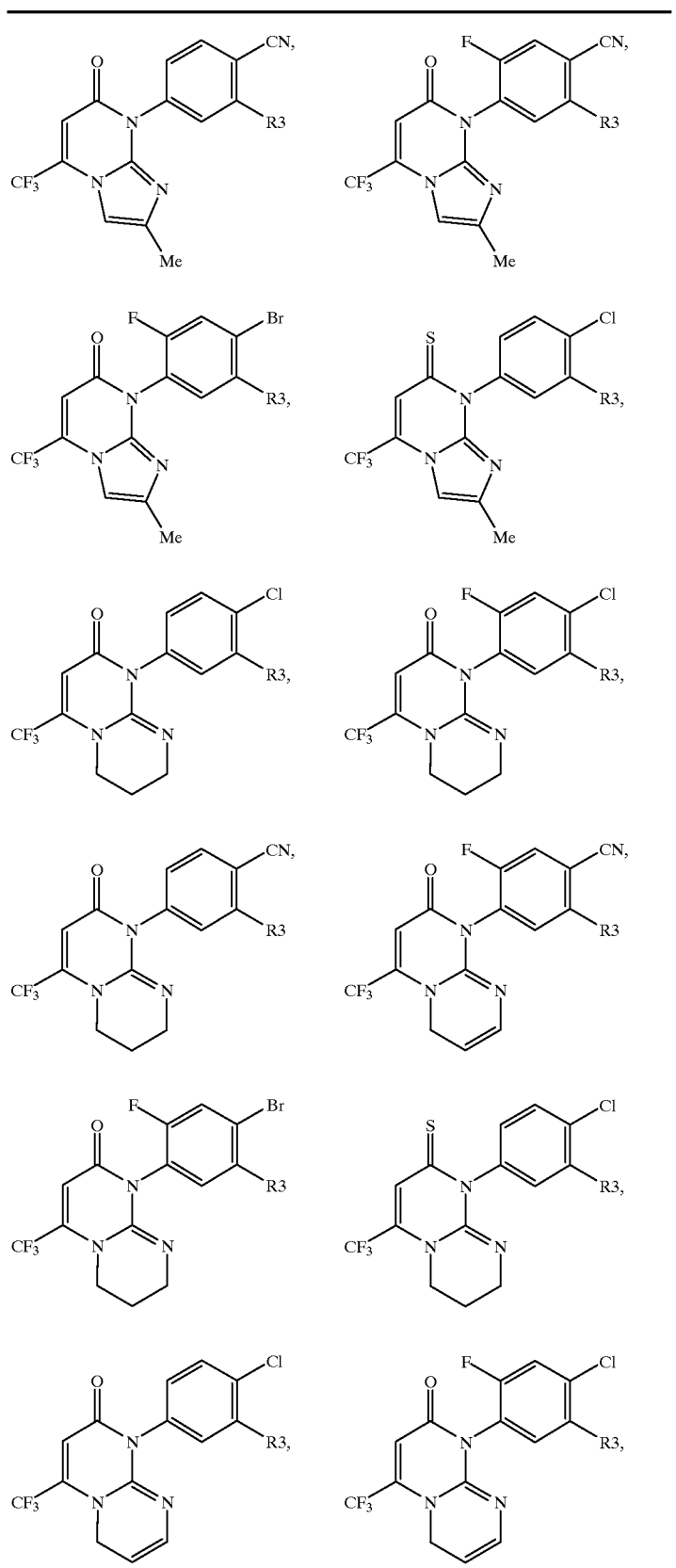

TABLE 3-continued
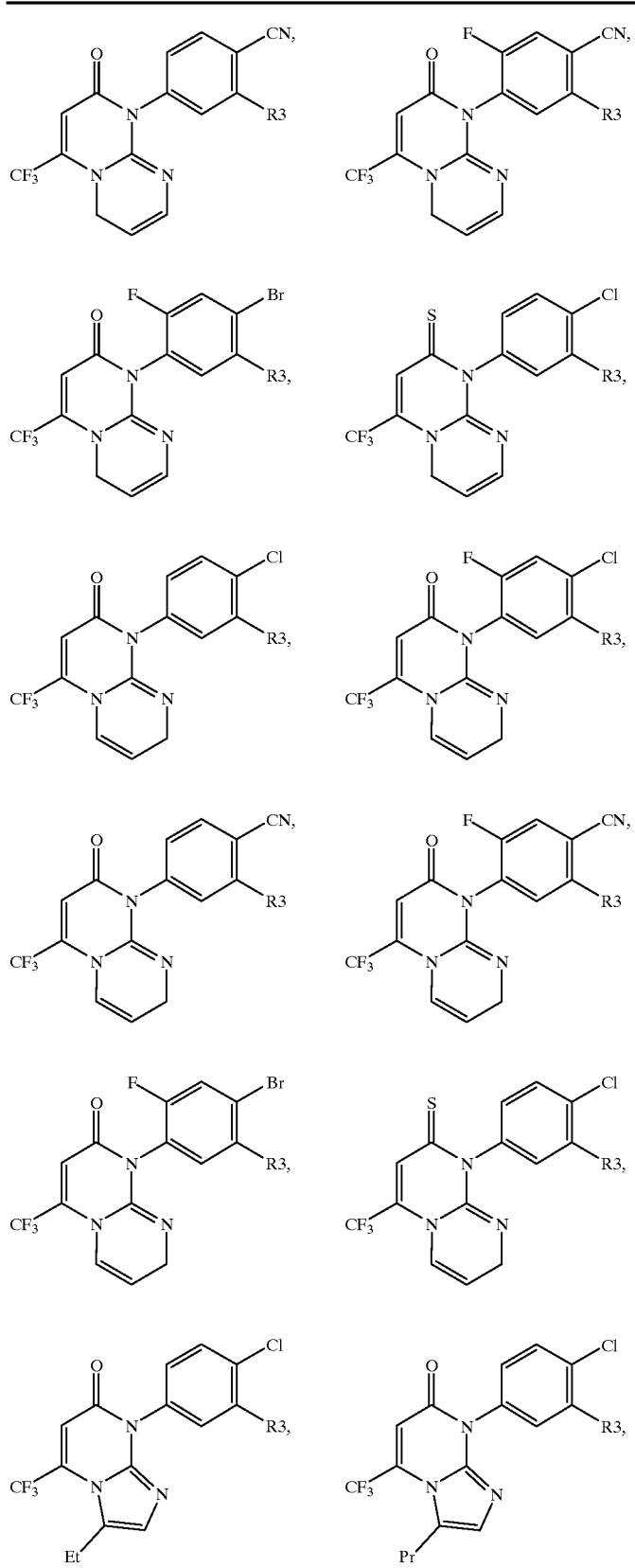

TABLE 3-continued
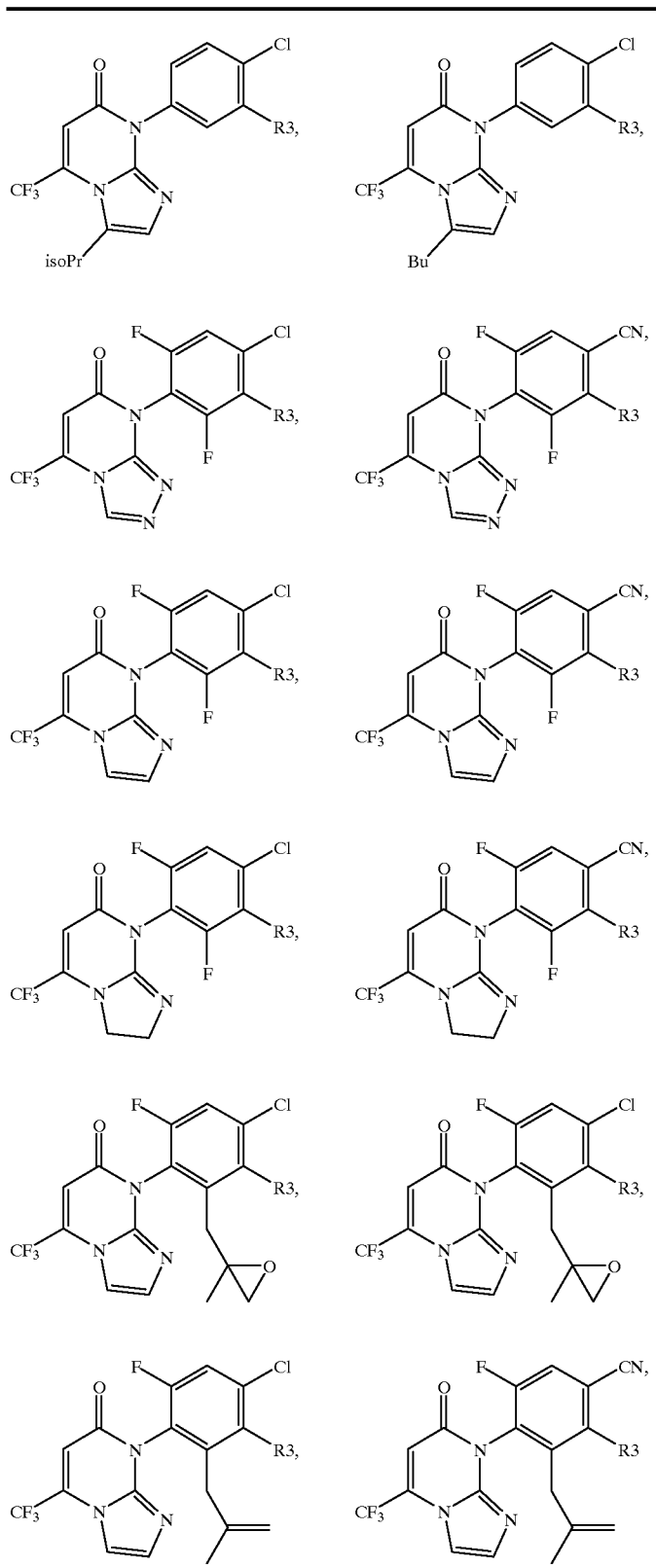

TABLE 3-continued
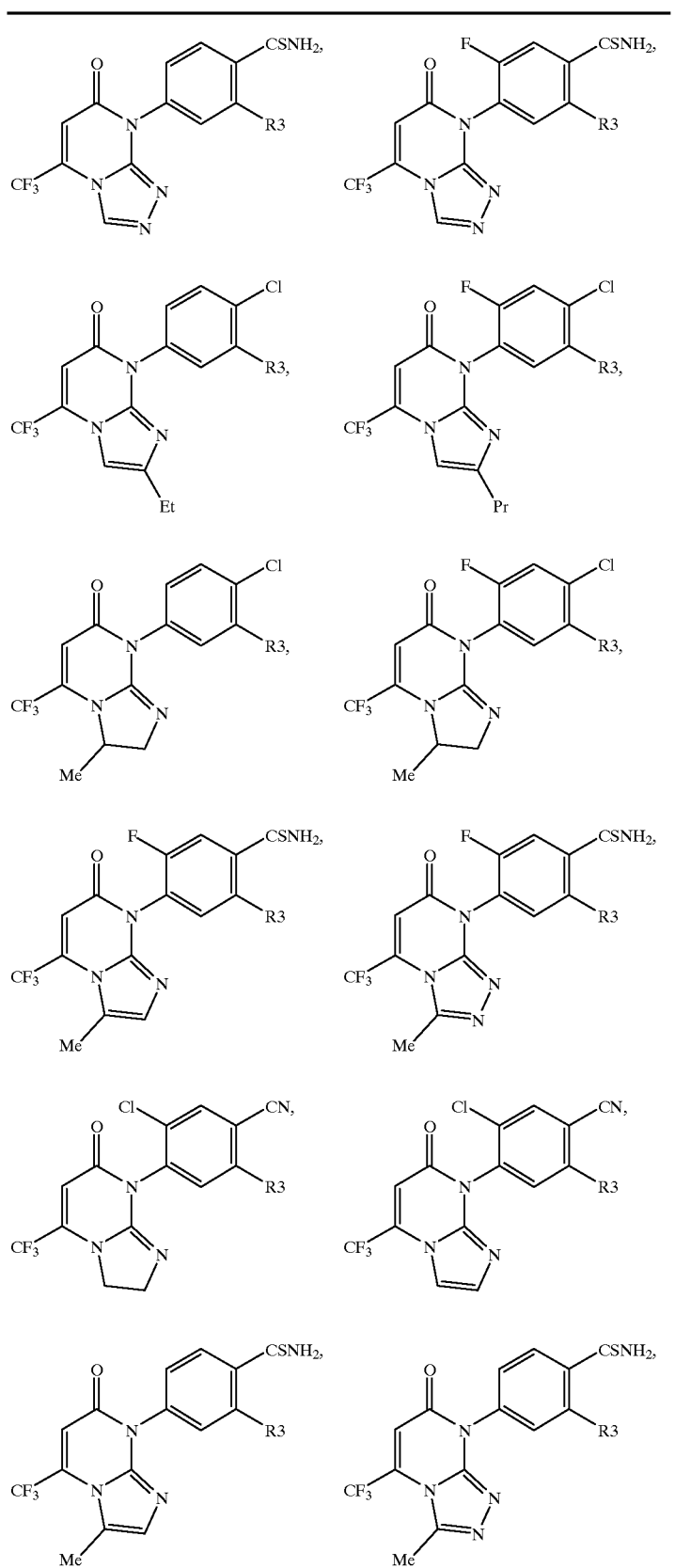

TABLE 3-continued
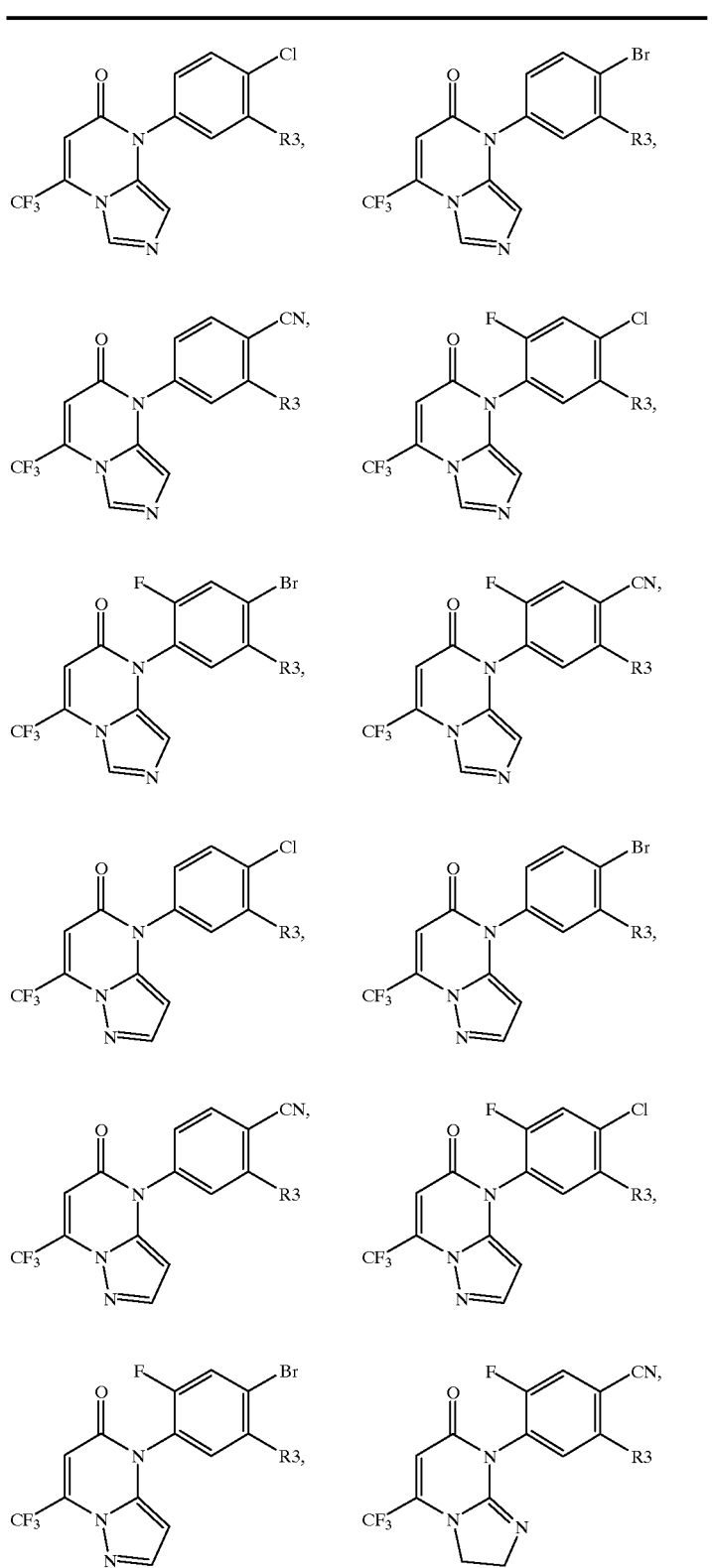

TABLE 3-continued
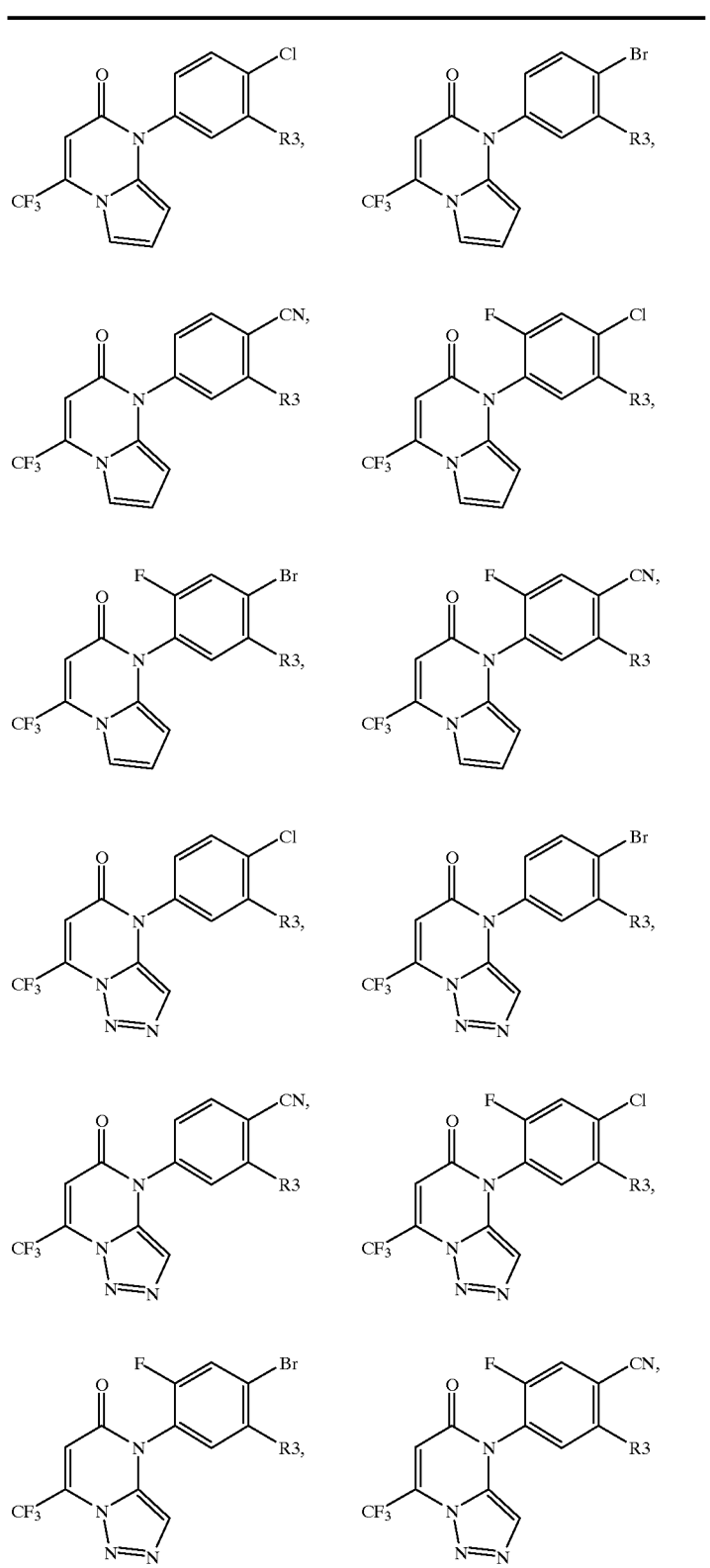

TABLE 3-continued
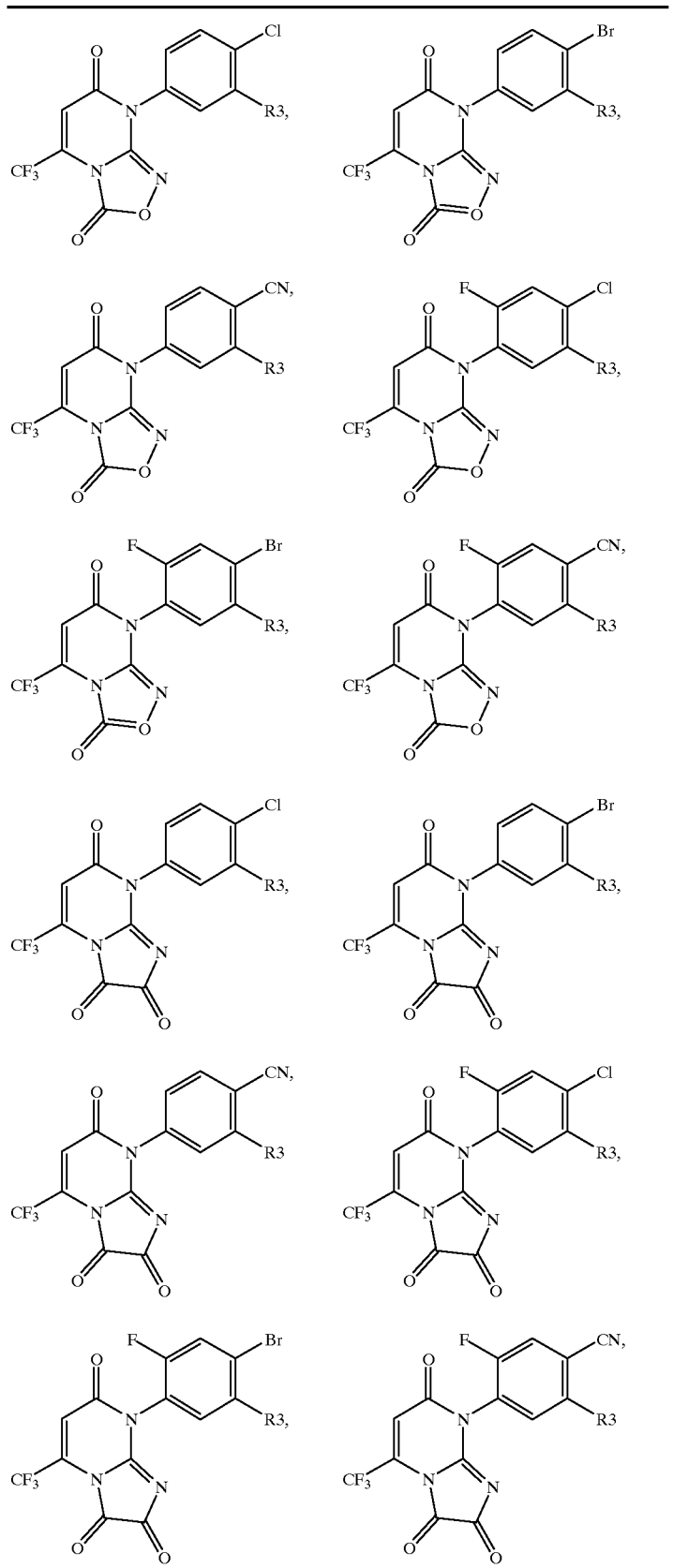

TABLE 3-continued
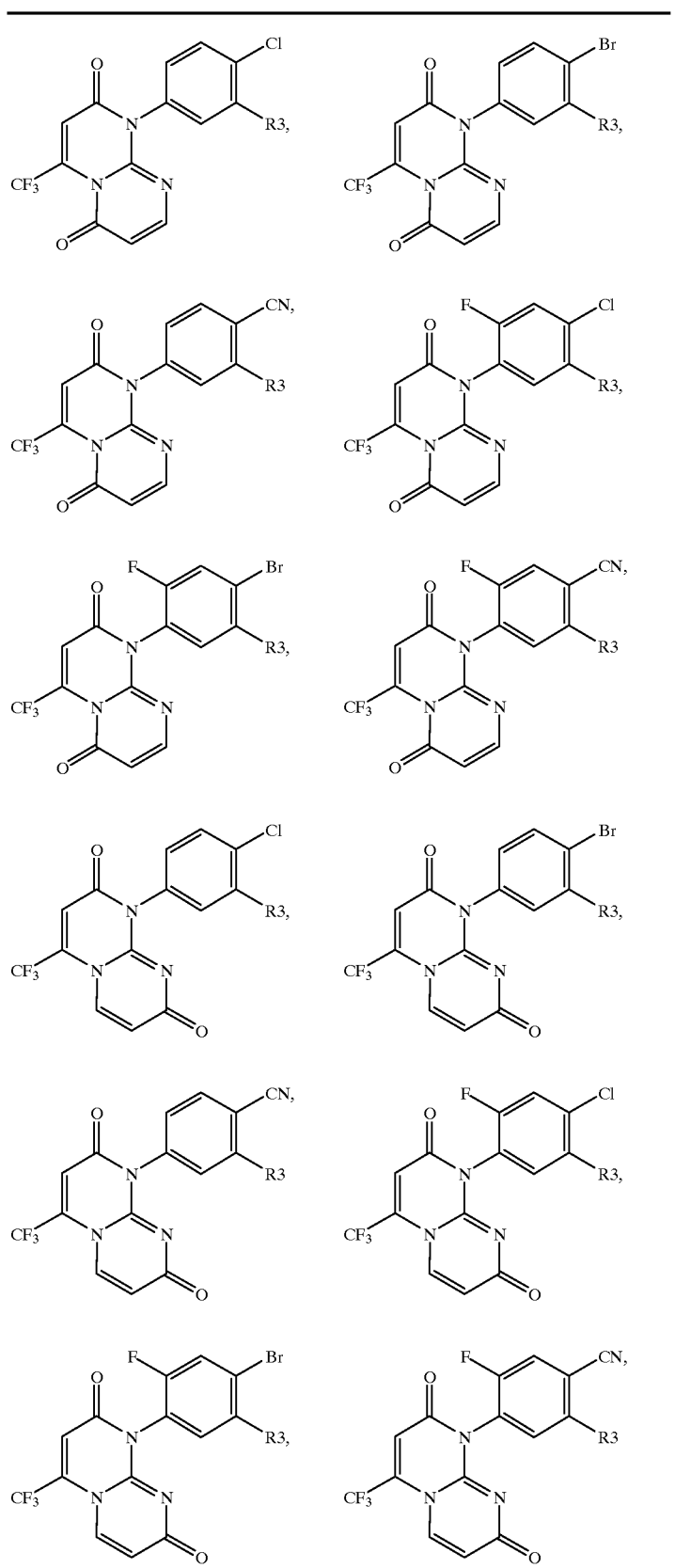

TABLE 3-continued
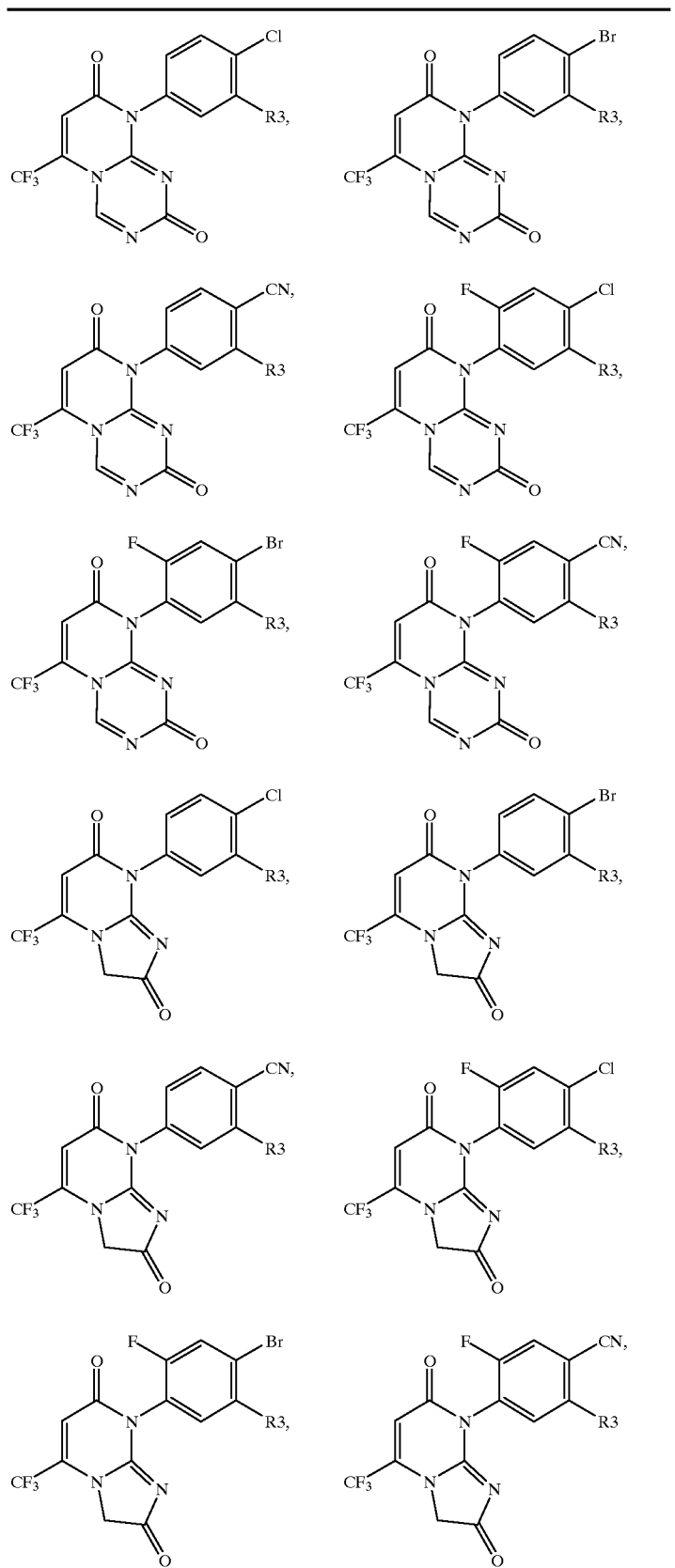

TABLE 3-continued
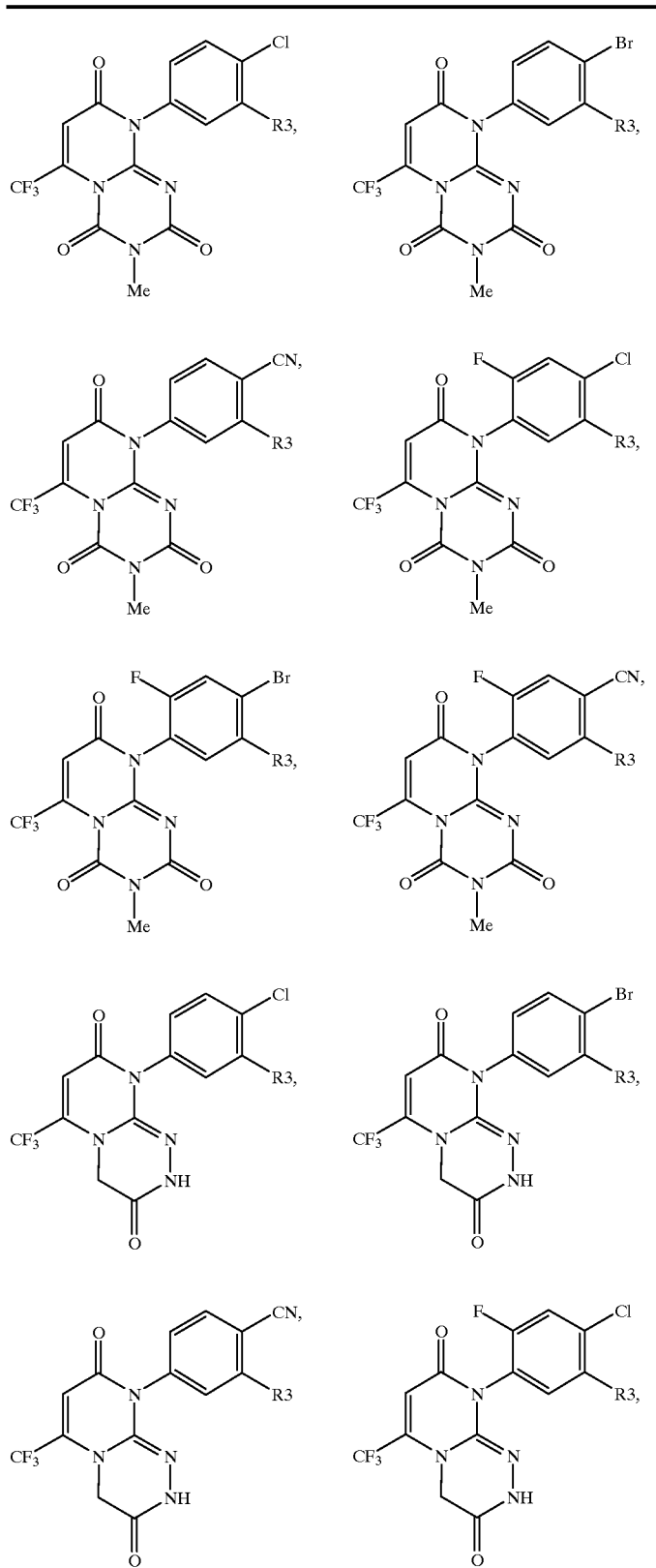

TABLE 3-continued
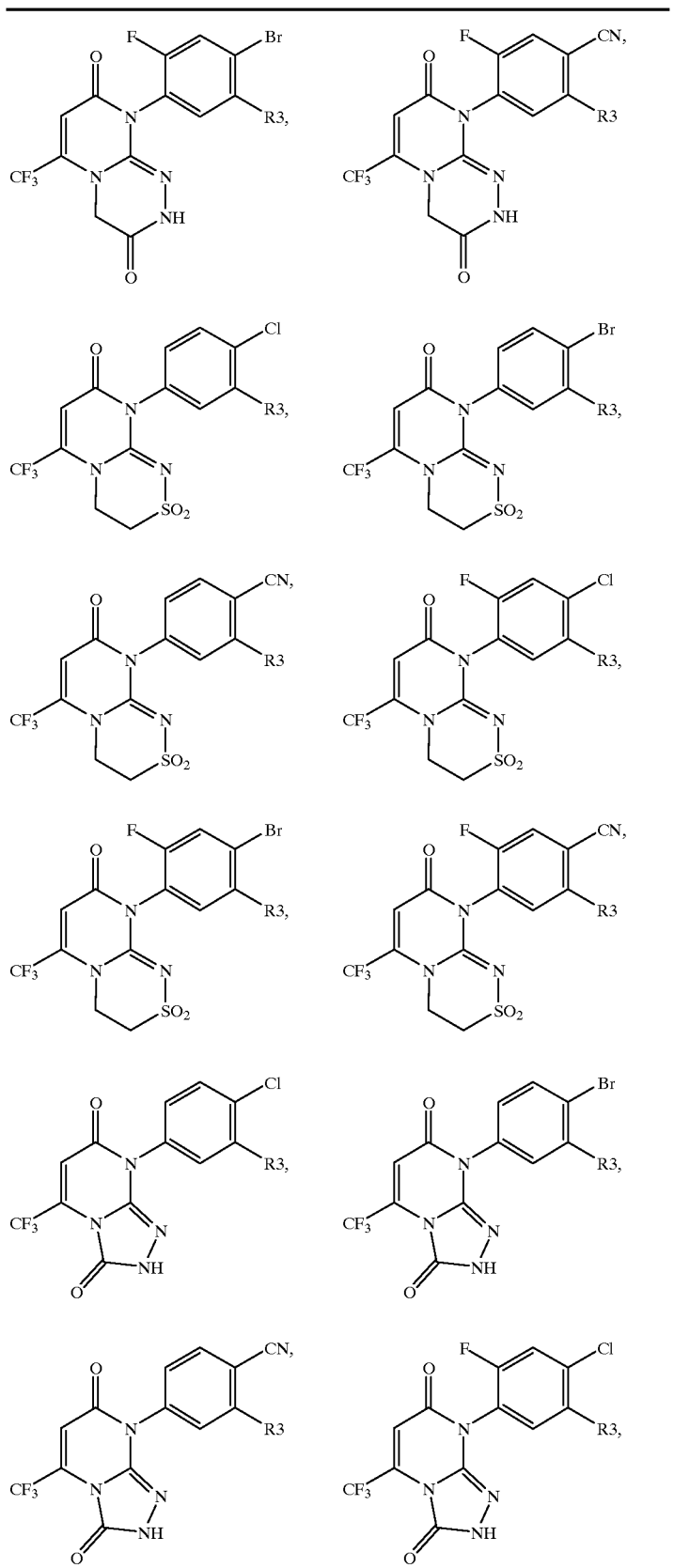

TABLE 3-continued
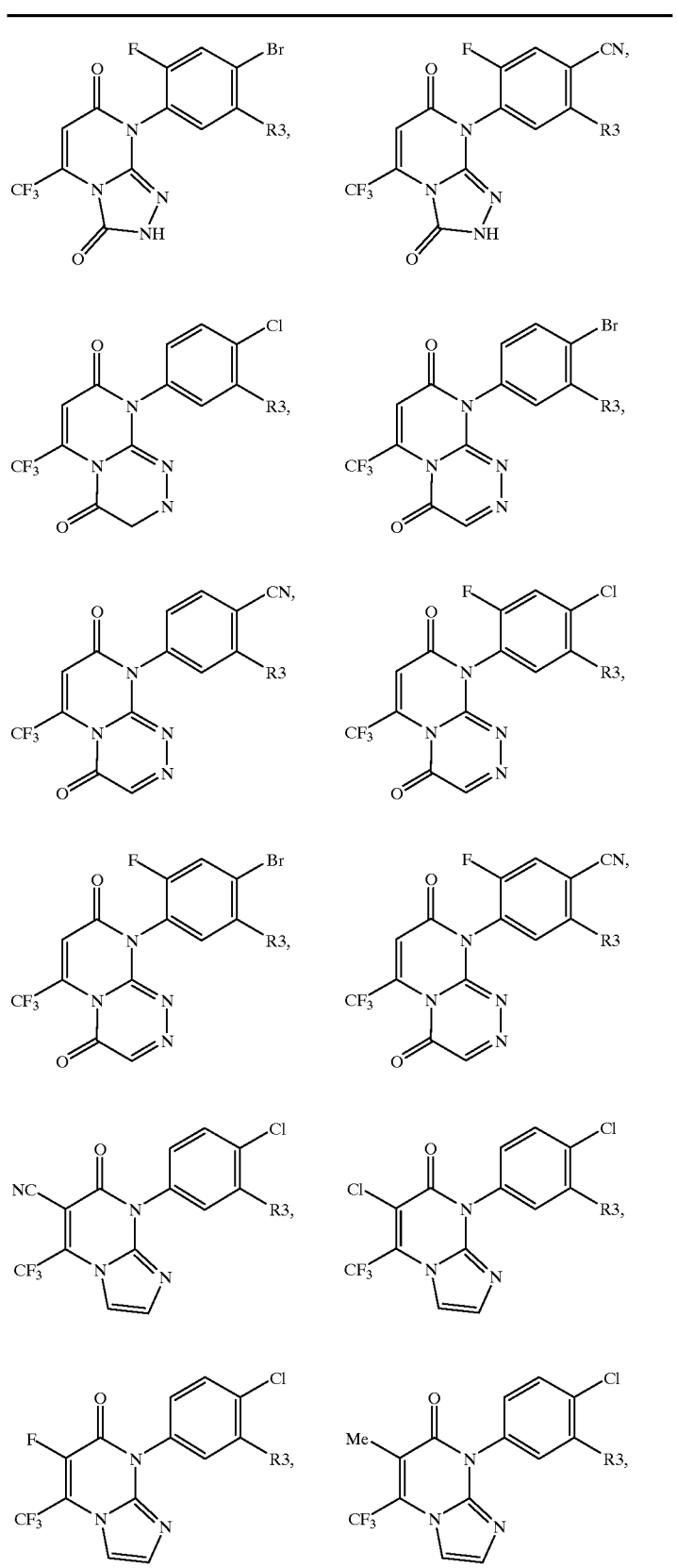

TABLE 3-continued
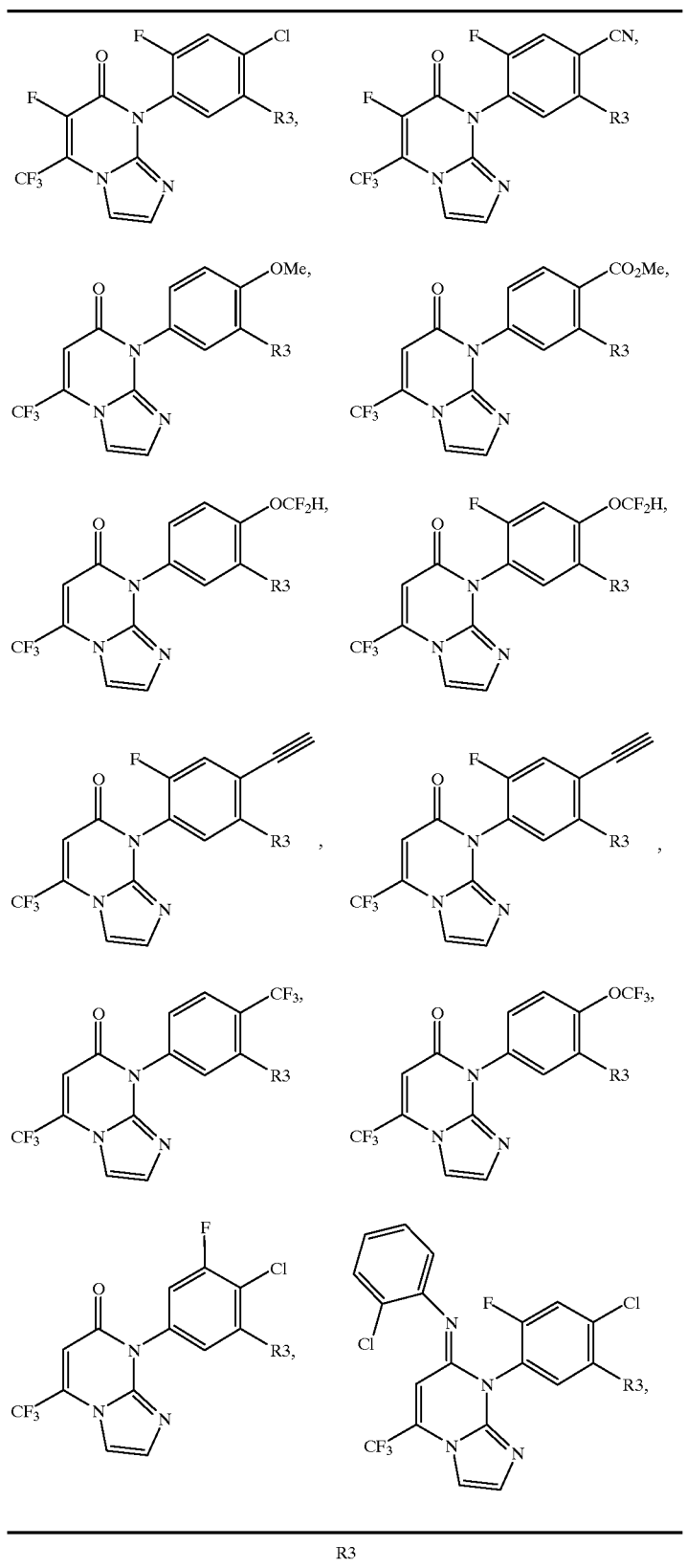
| R3 |
|---|
| H, Cl, F, Br, I, CHO, CO$_2$H, CONH$_2$, SO$_2$Cl, COMe, SH, OH, NH$_2$, NO$_2$, CN, phenyl, Me, Et, Pr, iso-Pr, Bu, sec-Bu, |

TABLE 3-continued iso-Bu, tert-Bu, Pn, neo-Pn, tert-Pn, cyclo-Pr, cyclo-Bu,
cyclo-Pn, cyclo-Hex, CH$_2$CH=CH$_2$, CH(Me)CH=CH$_2$, CH$_2$C≡CH,
CH(Me)C≡CH, O—Me, O—Et, O-iso-Pr, O—Pr, O—Bu, O-sec-Bu,
O-iso-Bu, O-cyclo-Pn, O-cyclo-Pr, O-cyclo-Hex, O-neo-Pn,
O-tert-Pn, O—Pn, O-Hex, O-Hep, O-Oct, OCH$_2$CH=CH$_2$,
OCH(Me)CH=CH$_2$, OC(Me)$_2$CH=CH$_2$, OCH$_2$C≡CH, OCH(Me)C≡CH,
OC(Me)$_2$C≡CH, OCH$_2$CH=C(Cl)H, OCH$_2$C(Cl)=CH$_2$, OCH$_2$CF$_3$,
OCH$_2$CH$_2$OMe, OCH$_2$CH$_2$OEt, OCH$_2$OMe, OCH$_2$OEt, OCH$_2$-cyclo-Pr,
OCH$_2$CN, OCOMe, OCOEt, OCOPr, OCO-iso-Pr, OCH$_2$C(Me)=CH$_2$,
O-iso-Pn, S—Me, S—Et, S-iso-Pr, S—Pr, S—Bu, S-sec-Bu, S-
iso-Bu, S-cyclo-Pn, S-cyclo-Pr, S-cyclo-Hex, S-neo-Pn,
S-tert-Pn, S—Pn, S-Hex, S-Hep, S-Oct, SCH$_2$CH=CH$_2$,
SCH(Me)CH=CH$_2$, SC(Me)$_2$CH=CH$_2$, SCH$_2$C≡CH, SCH(Me)C≡CH,
SC(Me)$_2$C≡CH, SCH$_2$CH=C(Cl)H, SCH$_2$C(Cl)=CH$_2$, SCH$_2$CF$_3$,
SCH$_2$CH$_2$OMe, SCH$_2$CH$_2$OEt, SCH$_2$OMe, SCH$_2$OEt, SCH$_2$-cyclo-Pr,
SCH$_2$CN, NH—Me, NH—Et, NH-iso-Pr, NH—Pr, NH—Bu, NH-sec-Bu,
NH-iso-Bu, NH-cyclo-Pn, NH-cyclo-Pr, NH-cyclo-Hex, NH-
neo-Pn, NH-tert-Pn, NH—Pn, NH-Hex, NH-Hep, NH-Oct,
NHCH$_2$CH=CH$_2$, NHCH(Me)CH=CH$_2$, NHC(Me)$_2$CH=CH$_2$, NHCH$_2$C≡CH,
NHCH(Me)C≡CH, NHC(Me)$_2$C≡CH, NHCH$_2$CH=C(Cl)H,
NHCH$_2$C(Cl)=CH$_2$, NHCH$_2$CF$_3$, NHCH$_2$CH$_2$OMe, NHCH$_2$CH$_2$OEt,
NHCH$_2$OMe, NHCH$_2$OEt, NHCH$_2$-cyclo-Pr, NHCH$_2$CN, CO$_2$Me, CO$_2$Et,
CO$_2$-iso-Pr, CO$_2$Pr, CO$_2$-cyclo-Pr, CO$_2$Bu, CO$_2$-sec-Bu, CO$_2$-
iso-Bu, CO$_2$-tert-Bu, CO$_2$-cyclo-Bu, CO$_2$Pn, CO$_2$-cyclo-Pn,
CO$_2$Pn, CO$_2$-neo-Pn, CO$_2$-tert-Pn, CO$_2$-Hex, CO$_2$-cyclo-Hex,
CO$_2$-Hep, CO$_2$-Oct, CO$_2$N(Me)$_2$, CO$_2$N(Et)$_2$, CO$_2$CH$_2$CO$_2$Me,
CO$_2$CH$_2$CO$_2$Et, CO$_2$CH$_2$CO$_2$Pr, CH$_2$CH(Cl)CO$_2$Me, CH$_2$CH(Cl)CO$_2$Et,
CH$_2$CH$_2$CO$_2$Me, CH$_2$CH$_2$CH$_2$CO$_2$Me, CH$_2$CO$_2$Me, CH=CHCO$_2$Me,
CH=CHCO$_2$Et, OCH$_2$CO$_2$Me, OCH$_2$CO$_2$Et, OCH$_2$CO$_2$Pr, OCH$_2$CO$_2$Bu,
OCH$_2$CO$_2$Pn, OCH$_2$CO$_2$Hex, OCH$_2$CO$_2$-cyclo-Pn, OCH$_2$CO$_2$-iso-Pr,
OCH$_2$CO$_2$CH$_2$Ph, OCH(Me)CO$_2$Me, OCH(Me)CO$_2$Et, OCH(Me)CO$_2$Pr,
OCH(Me)CO$_2$-iso-Pr, OCH(Me)(CO$_2$Pn, OCH(Me)CO$_2$-cyclo-Pn,
SCH$_2$CO$_2$Me, SCH$_2$CO$_2$Et, SCH$_2$CO$_2$Pr, SCH$_2$CO$_2$Bu, SCH$_2$CO$_2$Pn,
SCH$_2$CO$_2$Hex, SCH$_2$CO$_2$-cyclo-Pn, SCH$_2$CO$_2$-iso-Pr, SCH$_2$CO$_2$CH$_2$Ph,
SCH(Me)CO$_2$Me, SCH(Me)CO$_2$Et, SCH(Me)CO$_2$Pr, SCH(Me)CO$_2$-iso-
Pr, SCH(Me)CO$_2$Pn, SCH(Me)CO$_2$-cyclo-Pn, NHCH$_2$CO$_2$Me,
NHCH$_2$CO$_2$Et, NHCH$_2$CO$_2$Pr, NHCH$_2$CO$_2$Bu, NHCH$_2$CO$_2$Pn, NHCH$_2$CO$_2$Hex,
NHCH$_2$CO$_2$-cyclo-Pn, NHCH$_2$CO$_2$-iso-Pr, NHCH$_2$CO$_2$CH$_2$Ph,
NHCH(Me)CO$_2$Me, NHCH(Me)CO$_2$Et, NHCH(Me)CO$_2$Pr, NHCH(Me)CO$_2$-
iso-Pr, NHCH(Me)CO$_2$Pn, NHCH(Me)CO$_2$-cyclo-Pn, NHCO$_2$Me,
NHCO$_2$Et, NHCO$_2$Pr, NHCO$_2$-iso-Pr, NHCO$_2$Bu, NHCO$_2$cyclo-Pr,
NHCO$_2$-cyclo-Pn, NHCO$_2$-iso-Bu, NHCO$_2$sec-Bu, NHCO$_2$tert-Bu,
NHCO$_2$CH$_2$CH=CHCH$_3$, NHCO$_2$CH$_2$CH=CH$_2$, NHCO$_2$CH$_2$C≡CH, NHCO$_2$Ph,
NHCO$_2$CH$_2$Ph, NHCO$_2$CH$_2$-(2-Me—Ph), NHCO$_2$CH$_2$-(3-Me—Ph),
NHCO$_2$CH$_2$-(4-Me—Ph), NHCO$_2$CH$_2$-(4-Et—Ph), NHCO$_2$CH$_2$-(2-MeO—Ph),
NHCO$_2$CH$_2$-(3-MeO—Ph), NHCO$_2$CH$_2$-(4-MeO—Ph), NHCO$_2$CH$_2$-
(4-Cl—Ph), NHCO$_2$CH$_2$-(4-F—Ph)(, NHCO$_2$CH$_2$-(4-CF$_3$—Ph),
NHCO$_2$CH$_2$-(2-F—Ph), NHCO$_2$CH$_2$-(3-F—Ph), NHCO$_2$CH$_2$-(3-Cl—Ph),
NHCO$_2$CH$_2$-(2-Cl—Ph), NHCO$_2$CH$_2$-(4-CF$_3$O—Ph), NHSO$_2$Me, NHSO$_2$Et,
NHSO$_2$Pr, NHSO$_2$-iso-Pr, NHSO$_2$Bu, NHSO$_2$CH$_2$Ph, NHSO$_2$CHCl$_2$,
NHSO$_2$CH$_2$Cl, NHSO$_2$CH$_2$CH$_2$Cl, NHSO$_2$CH$_2$CH$_2$CH$_2$Cl, NHSO$_2$CH$_2$CF$_3$,
NHSO$_2$Ph, N(SO$_2$Et)CO$_2$Et, N(CH$_2$OMe)SO$_2$Et, N(CH$_2$CH=CH$_2$)SO$_2$Et,
N(CH$_2$C≡CH)SO$_2$Et, N(Me)SO$_2$Me, N(SO$_2$Me)$_2$, N(SO$_2$Et)$_2$,
N(SO$_2$Pr)$_2$, N(Et)SO$_2$Et, N(Me)SO$_2$Et, N(Et)SO$_2$Et, N(Pr)SO$_2$Et,
N(COMe)SO$_2$Et, N(CH$_2$OMe)SO$_2$Me, N(CH$_2$OEt)SO$_2$Me,
N(CH$_2$CH=CH2)SO$_2$Me, N(CH$_2$C≡CH)SO$_2$Me, CONHSO$_2$Me, CONHSO$_2$Et,
CONHSO$_2$CF$_3$, 1,3-dioxolan-2-yl, 1,3-dioxan-2-yl, 4-[1-
(ethoxycarbonyl)ethyloxy]phenyl, 4-[1-(ethoxycarbonyl)-
ethyloxy]phenyloxy, N(Me)CO$_2$Me, N(CH$_2$C≡CH)CO$_2$Me,
N(Me)COMe, NHCOMe, NHCOPr, N(CH$_2$C=CH)COMe, N(CH$_2$C≡CH)CO$_2$Me,
N(Me)CO$_2$CH$_2$-(4-Cl—Ph), N(CH$_2$C≡CH)CO$_2$Et, N(CO-
tert-Bu)SO$_2$Me, N(CO-tert-Bu)SO$_2$Et, N(2-Me[000f]-benzoyl)SO$_2$Me,
N-(3-MeO-benzoyl)SO$_2$Me, N(4-MeO-benzoyl)SO$_2$Me, N(2-MeO-
benzoyl)SO$_2$Et, N(3-MeO-benzoyl)SO$_2$Et, N(4-MeO-
benzoyl)SO$_2$Et, CO$_2$-(oxetan-3-yl), N(CHO)CH$_2$CO$_2$Me,
N(CHO)CH$_2$CO$_2$Et, N(CHO)CH(Me)CO$_2$Et, N(COMe)CH$_2$CO$_2$Me,
N(COMe)CH(Me)CO$_2$Me, N(CH$_2$C≡N)CO$_2$Me, CH=C(Cl)CO$_2$Me,
CH=C(Cl)CO$_2$Et, CH=C(Br)CO$_2$Me, CH=C(Br)CO$_2$Et, NHCOCF$_3$,
NHCOCCl$_3$, NHCOCF$_2$Cl, NHCOCF$_2$H, OCO$_2$Me, OCO$_2$Et, or N(CH$_2$C≡N)SO$_2$Me

[TABLE 4]
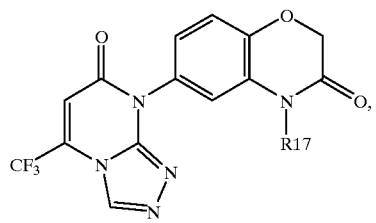
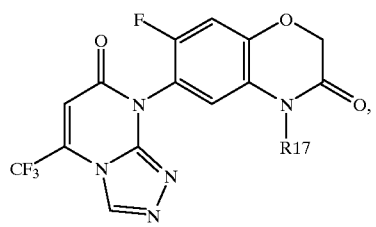
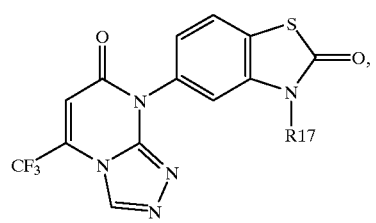
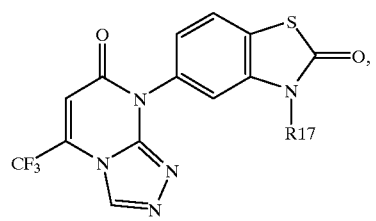
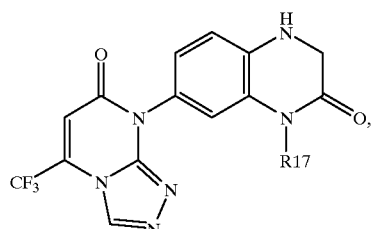
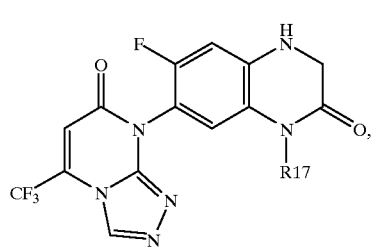
[TABLE 4]-continued
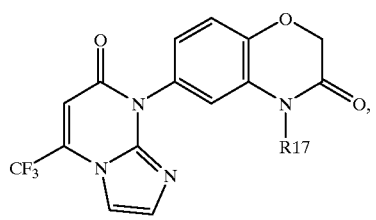
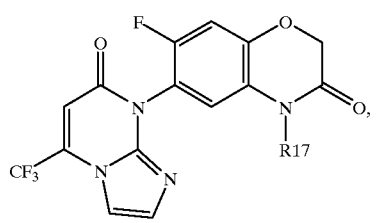
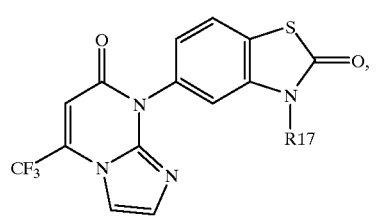
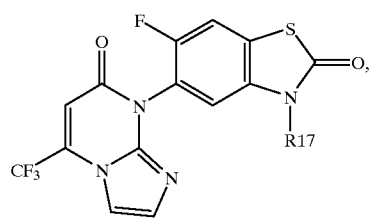
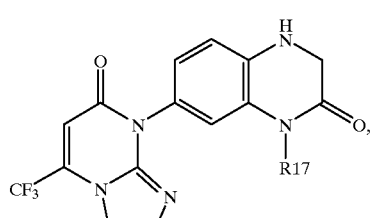
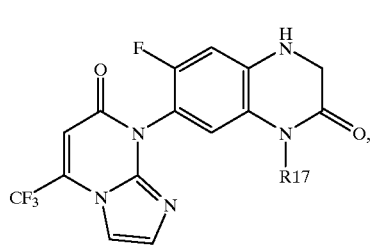

[TABLE 4]-continued
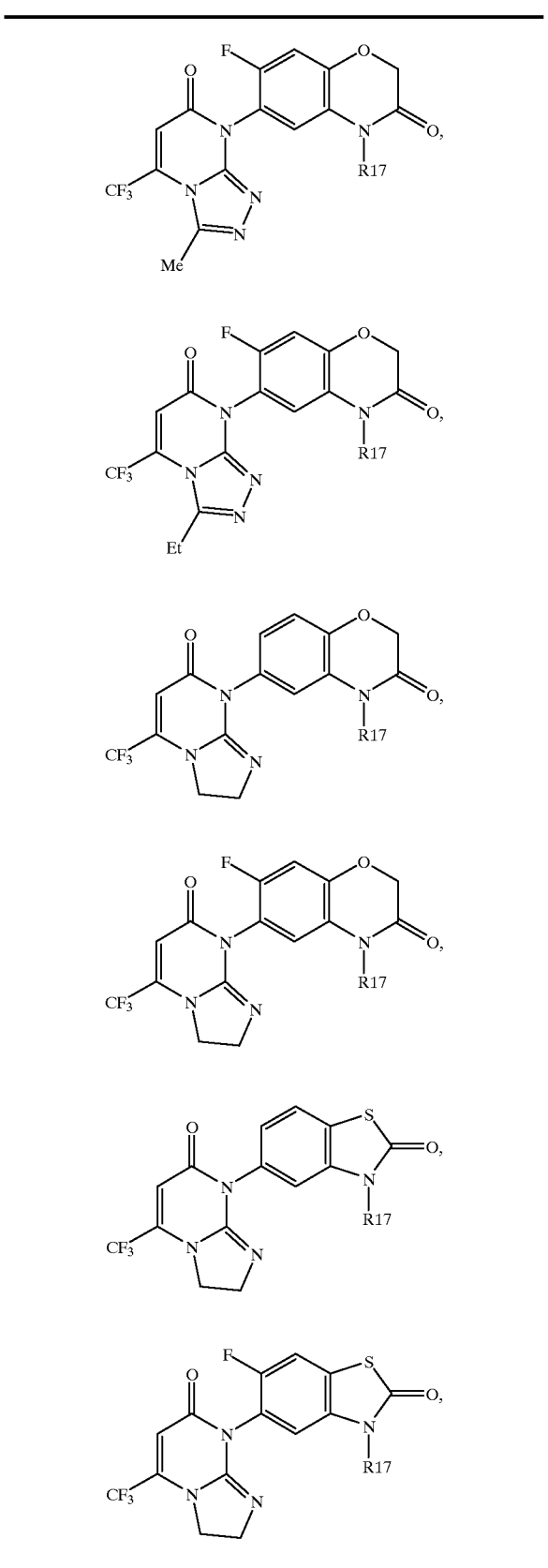
[TABLE 4]-continued
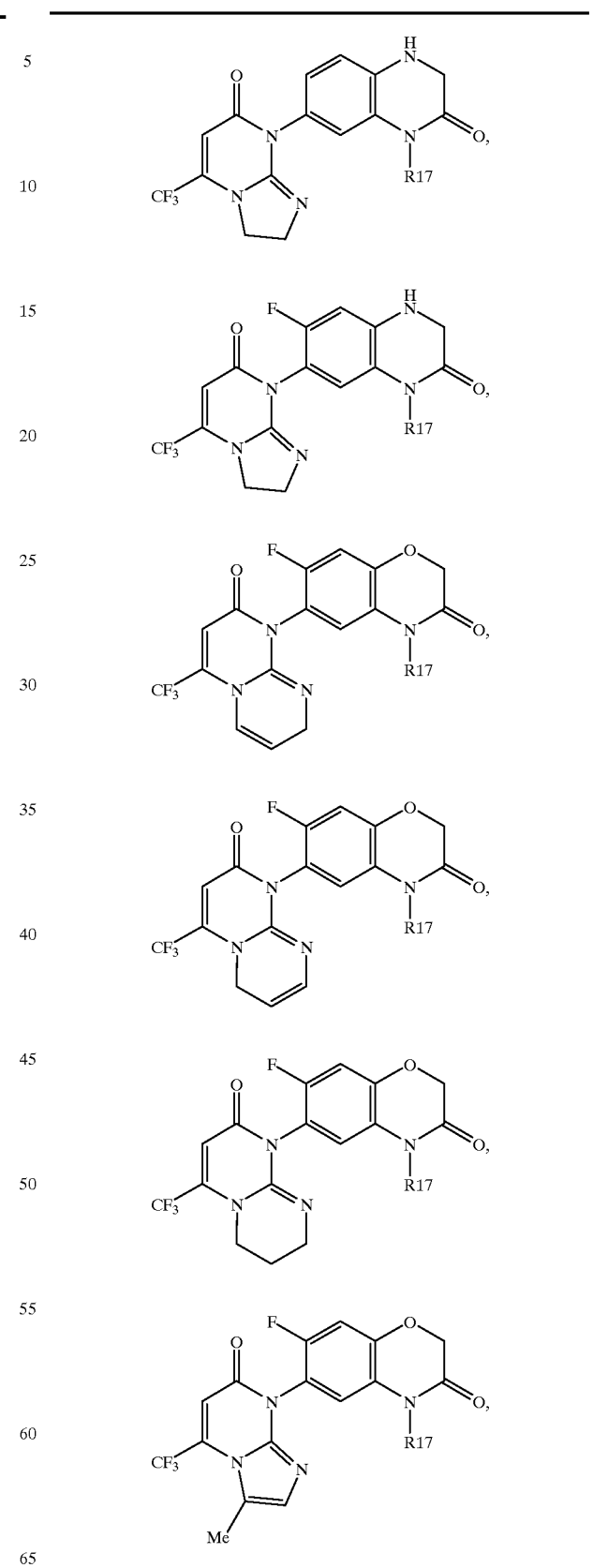

[TABLE 4]-continued

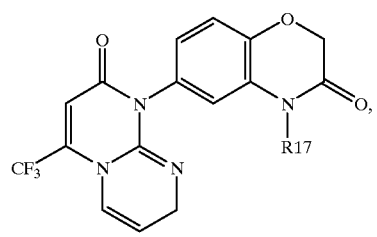
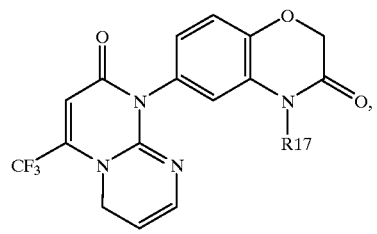
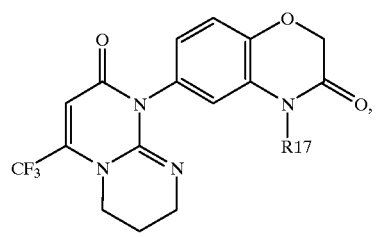
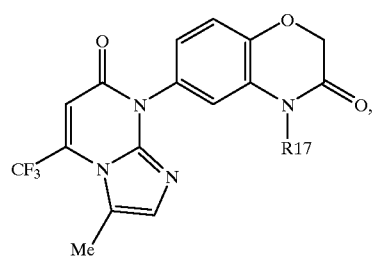
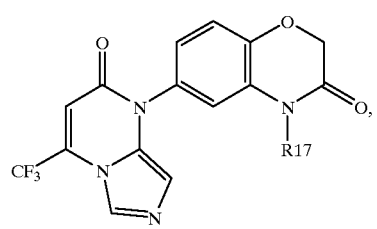
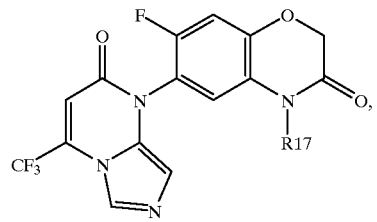

[TABLE 4]-continued

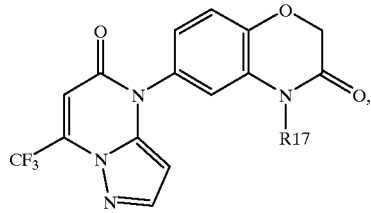
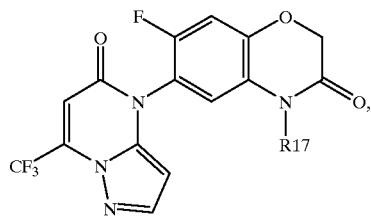
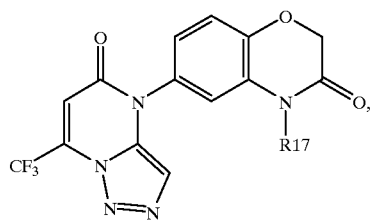
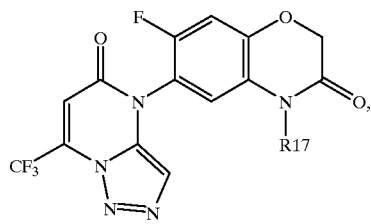

| R17 |
|---|
| Me, Et, Pr, iso-Pr, Bu, sec-Bu, iso-Bu, CH$_2$CH=CH$_2$, CH$_2$C≡CH, CH$_2$C≡N, CH$_2$CH$_2$F, CH$_2$CH$_2$Cl, CH$_2$CH$_2$CH$_2$F, CH$_2$OMe, CH$_2$OEt, CH$_2$CH$_2$CH$_2$Cl, CH$_2$CH$_2$CH$_2$CH$_2$F, CH$_2$CCl=CH$_2$, CH$_2$CBr=CH$_2$, OMe, OEt, CH(Me)C≡CH, CH(Me)CH=CH$_2$ or CH(Me)C≡N |

The abbreviations used in the above tables represent the following meanings:

Me: CH$_3$,
Et: CH$_2$CH$_3$,
Pr: CH$_2$CH$_2$CH$_3$,
iso-Pr: CH(CH$_3$)$_2$,
cyclo-Pr: CH(CH$_2$)$_2$,
Bu: CH$_2$CH$_2$CH$_2$CH$_3$,
sec-Bu: CH(CH$_3$)C$_2$H$_5$,
iso-Bu: CH$_2$CH(CH$_3$)$_2$,
tert-Bu: C(CH$_3$)$_3$,
cyclo-Bu: CH(CH$_2$)$_3$,
Pn: CH$_2$CH$_2$CH$_2$CH$_2$CH$_3$,
cyclo-Pn: CH(CH$_2$)$_4$,
iso-Pn: CH$_2$CH$_2$CH(CH$_3$)$_2$,
neo-Pn: CH$_2$C(CH$_3$)$_3$,
cyclo-Hex: CH(CH$_2$)$_5$, tert-Pn: $C(CH_3)_2C_2H_5$, Hex: $(CH_2)_5CH_3$, Hep: $(CH_2)_6CH_3$, Oct: $(CH_2)_7CH_3$, Ph, phenyl: $C_6H_5$, 4-Cl-Ph: 4-Cl-phenyl.

In use of the compounds of the present invention as a herbicide, they may be usually mixed with an appropriate carrier, for example, a solid carrier such as clay, talc, bentonite, urea, ammonium sulfate, walnut flour, diatomaceous earth and white carbon; or a liquid carrier such as water, alcohols (isopropanol, butanol, ethylene glycol, benzyl alcohol, furfuryl alcohol, etc.), aromatic hydrocarbons (toluene, xylene, methyl naphthalene, etc.), ethers (anisole, etc.), vegetable oils (soybean oil, cottonseed oil, etc), ketones (cyclohexanone, isophorone, etc.), esters (butyl acetate, etc.), acid amides (N-methylpyrrolidone, etc.), and halogenated hydrocarbons (chlorobenzene, etc.). Also, if necessary, they may be added with a suitable adjuvant such as surfactant, emulsifier, dispersant, penetrating agent, spreader, thickener, anti-freezing agent, coagulation preventing agent, stabilizer and the like, and can be practically used in various forms of formulation such as liquid formulation, emulsifiable concentrate, wettable powder, dry flowable, flowable, dust or granule.

The compounds of the present invention may be mixed, if necessary, with other kinds of herbicide, various kinds of insecticide, acaricide, nematocide, fungicide, plant growth regulator, synergist, fertilizer, soil conditioner and the like in the course of formulating process or at the time of application.

In particular, combined application of the compound of the present invention with other pesticide(s) can result in reducing the cost through decrease of the application rate, expanding the spectrum and improving herbicidal performance through synergistic effect between combined pesticides. In this connection, the compound of the present invention may be combined with two or more known pesticides. As the kinds of pesticides which can be combined with the compound of the present invention in use thereof, there can be mentioned, for instance, the compounds described in Farm Chemicals Handbook (1996).

The application rate of the compound of the present invention is variable depending on the place, time and method of its application, weather condition, formulation, soil condition and the crop to be treated and the like. It is, however, generally appropriate to apply the compound of the present invention as the active ingredient in an amount of about 0.0001–10 kg/ha, preferably about 0.001–5 kg/ha.

Shown below are the examples of formulations using the compounds of the present invention. It should be understood, however, that the formulations coming within the concept of the present invention are not limited to those shown below. In the following description of the examples of formulations, all "parts" are by weight unless otherwise noted.

| | Parts |
|---|---|
| Wettable Powder | |
| Compound of the present invention | 0.1–80 |
| Solid carrier | 10–90 |
| Surfactant | 1–10 |
| Others | 1–5 |
| (Others include coagulation preventing mg agent and the like.) | |
| Emulsifiable Concentrate | |
| Compound of the present invention | 0.1–30 |
| Liquid carrier | 30–95 |
| Surfactant | 5–15 |
| Flowable | |
| Compound of the present invention | 0.1–70 |
| Liquid carrier | 15–65 |
| Surfactant | 5–12 |
| Others | 5–30 |
| (Others include anti-freezing agent, thickener and the like.) | |
| Granular Wettable Powder (Dry Flowable) | |
| Compound of the present invention | 0.1–90 |
| Solid carrier | 10–70 |
| Surfactant | 1–20 |
| Granule | |
| Compound of the present invention | 0.0001–10 |
| Solid carrier | 90–99.9999 |
| Others | 0.1–10 |

Formulation Example 1; Wettable Powder

| | |
|---|---|
| Compound No. 4 of the present invention | 50 |
| Zeeklite PFP (trademark) | 43 |
| (kaolin type clay: mfd. by Zeeklite Industries Co., Ltd.) | |
| Sorpol 5050 (trademark) | 2 |
| (anionic surfactant: mfd. by Toho Chemical Co., Ltd.) | |
| Runox 1000 C (trademark) | 3 |
| (anionic surfactant: mfd. by Toho Chemical Co., Ltd.) | |
| Carplex #80 (trademark: coagulation preventing agent) | 2 |
| (white carbon: mfd. by Shionogi Pharmaceutical Co., Ltd.) | |

The above ingredients are homogeneously blended and ground to formulate a wettable powder.

Formulation Example 2: Emulsifiable Concentrate

| | |
|---|---|
| Compound No. 51 of the present invention | 3 |
| Xylene | 76 |
| Isophorone | 15 |
| Sorpol 3005 X (trademark) | 6 |
| (mixture of nonionic and anionic surfactants: mfd. by Toho Chemical Co., Ltd.) | |

The above ingredients are homogeneously blended to formulate an emulsifiable concentrate.

Formulation Example 3; Flowable

| | |
|---|---|
| Compound No. 6 of the present invention | 35 |
| Agrizole S-711 (trademark) | 8 |
| (nonionic surfactant: mfd. by Kao Corporation) | |
| Runox 1000 C (trademark) | 0.5 |
| (anionic surfactant: mfd. by Toho Chemical Co., Ltd.) | |
| 1% Rodopol water (trademark) | 20 |
| (thickener: mfd. by Rhone-Poulenc) | |
| Ethylene glycol (anti-freezing agent) | 8 |
| Water | 28.5 |

The above ingredients are homogeneously blended to formulate a flowable.

Formulation Example 4; Granular Wettable Powder (Dry Flowable)

| | |
|---|---|
| Compound No. 25 of the present invention | 75 |
| Isobam No. 1 (trademark) | 10 |
| (anionic surfactant: mfd. by Kuraray Isoprene Chemical Co., Ltd.) | |
| Vanilex N (trademark) | 5 |
| (anionic surfactant: mfd. by Sanyo Kokusaku Pulp K.K.) | |
| Carplex #80 (trademark) | 10 |
| (white carbon: mfd. by Shionogi Pharmaceutical Co., Ltd.) | |

-continued

| | Parts |
|---|---|
| The above ingredients are homogeneously blended and pulverized to formulate a dry flowable. | |
| Formulation Example 5; Granules | |
| Compound No. 34 of the present invention | 0.1 |
| Bentonite | 50.0 |
| Talc | 44.9 |
| Toxanon GR-31A (trademark) | 5.0 |
| (anionic surfactant: mfd. by Sanyo Kasei Co., Ltd.) | |

The above ingredients are homogeneously blended and ground, to which then a small amount of water is added, and the resulting mixture is kneaded with stirring, granulated by an extrusion granulator and dried to formulate granules.

In practical use of the above formulations, the wettable powder, emulsifiable concentrate, flowable and granular wettable powder are diluted 50–1000 times with water and then applied so that the active ingredient will be supplied at a rate of 0.0001 to 10 kg per hectare.

The following test examples specifically illustrate the utility of the compound of the present invention as an active ingredient of herbicides.

TEST EXAMPLE 1

Test on Herbicidal Effect by Pre-Emergence Treatment Under Flooded Condition

An alluvial soil was placed in 1/10000 are Wagner pots and then water was poured thereinto to puddle the soil to prepare a flooded condition with 4 cm of the depth of water. Rice seedlings of 2-leaf stage were transplanted to the pots and seeds of *Echinochloa crus-galli* (barnyardgrass), *Scirpus juncoides*, *Monochoria vaginalis* and *Rotala indica* and tubers of *Sagittaria pygmaea* and *Cyperus serotinus* were mix-seeded in the above pots. The pots were arranged in a greenhouse at the controlled temperature of 25 to 30° C. and the plants were grown therein. One day after seeding the weeds, the compounds of the present invention, which had been formulated according to the above Formulation Examples, were applied onto the water surface such that a predetermined application rate was applied. Three weeks after the application of each compound, its herbicidal effect on each weed and the influence on rice plant were examined on the basis of visual observation and evaluated according to the following Evaluation Criteria, which employs 5 grades wherein zero represents that there is no influence on plants treated, and 5 represents that plants treated is completely killed. The results obtained are shown in Table 5-1.

In this connection, "No." described in the following Tables corresponds to "Compound No." described in the above Examples, and symbols represent the following meanings;

A: *Echinochloa crus-galli*,
B: *Scirpus juncoides*,
C: *Monochoria vaginalis*,
D: *Rotala indica*
E: *Sagittaria pygmaea*,
F: *Cyperus serotinus*,
b: rice plant.

Evaluation Criteria

5: Control rate is at least 90% (almost completely killed);
4: Control rate is at least 70% to less than 90%;
3: Control rate is at least 40% to less than 70%;
2: Control rate is at least 20% to less than 40%;
1: Control rate is at least 5% to less than 20%;
0: Control rate is less than 5% (almost no effect shown).

TEST EXAMPLE 2

Test on Herbicidal Effect by Growing Stage Treatment Under Flooded Condition

An alluvial soil was placed in 1/10000 are Wagner pots and then water was poured thereinto to puddle the soil to prepare a flooded condition with 4 cm of the depth of water. Seeds of *Echinochloa crus-galli* (barnyardgrass), *Scirpus juncoides*, *Monochoria vaginalis* and *Rotala indica* were mix-seeded in the above pots. The pots were arranged in a greenhouse at the controlled temperature of 25 to 30° C. and the plants were grown therein. Fourteen days after seeding the weeds, the compounds of the present invention, which had been formulated according to the above Formulation Examples, were applied onto the water surface such that a predetermined application rate was applied. Three weeks after the application of each compound, its herbicidal effect on each weed was examined on the basis of visual observation and evaluated according to the Evaluation Criteria of the above Test Example 1. The results obtained are shown in Table 5-2.

In this connection, "No." described in the following Tables corresponds to "Compound No." described in the above Examples, and symbols represent the following meanings;

A: *Echinochloa crus-galli*,
B: *Scirpus juncoides*,
C: *Monochoria vaginalis*,
D: *Rotala indica*.

TEST EXAMPLE 3

Test on Herbicidal Effect by Soil Treatment

A sterilized diluvial soil was placed in a 33 cm×33 cm×8 cm plastic cases. Seeds of *Echinochloa crus-galli*, *Setaria viridis*, *Avena fatua*, *Alopecurus myosuroides*, *Abutilon theophrasti*, *Xanthium pensylvanicum*, *Amaranthus viridis*, *Ipomoea purpurea*, *Veronica persica*, *Stellaria media*, *Digitaria adscendens*, *Ambrosia artemisiaefolia*, *Amaranthus retroflexus*, *Chenopodium album*, *Polygonum Blumei*, corn, rice, wheat, soybean, cotton and sugar beet were mix-seeded, and covered with soil to the depth of about 1.5 cm, and then the compounds of the present invention, which had been formulated according to the above Formulation Examples, were uniformly sprayed on the soil surface such that a predetermined application rate was applied. Three weeks after the application of each compound, its herbicidal effect on each weed and the influence on each crop were examined on the basis of visual observation and evaluated according to the Evaluation Criteria of the above Test Example 1. The results obtained are shown in Table 5-3.

In this connection, "No." described in the following Tables corresponds to "Compound No." described in the above Examples, and symbols represent the following meanings;

G: *Echinochloa crus-galli*,
H: *Setaria viridis*,
I: *Avena fatua*,
J: *Alopecurus myosuroides*,
K: *Abutilon theophrasti*,
L: *Xanthium pensylvanicum*,
M: *Amaranthus viridis*,
N: *Ipomoea purpurea*,
O: *Veronica persica*, P: *Stellaria media*,
Q: *Digitaria adscendens*,
R: *Ambrosia artemisiaefolia*,
S: *Amaranthua retroflexus*,
T: *Chenopodium album*,
U: *Polygonum Blumei*,
 a: corn,
 b: rice,
 c: soybean,
 d: cotton,
 e: wheat,
 f: sugar beet.

TEST EXAMPLE 4

Test on Herbicidal Effect by Foliage Treatment

A sterilized diluvial soil was placed in a 33 cm×33 cm×8 cm plastic cases. Seeds of *Echinochloa crus-galli, Setaria viridis, Avena fatua, Alopecurus myosuroides, Abutilon theophrasti, Xanthium pensylvanicum, Amaranthus viridis, Ipomoea purpurea, Veronica persica, Stellaria media, Digitaria adscendens, Ambrosia artemisiaefolia, Amaranthus retroflexus, Chenopodium album, Polygonum Blumei*, corn, rice, wheat, soybean, cotton and sugar beet were mix-seeded, and covered with soil to the depth of about 1.5 cm. The plants were grown for 14 days at room temperature of 25 to 30° C., and then the compounds of the present invention which had been formulated according to the above Formulation Examples were uniformly sprayed on the foliage of each plant. Three weeks after the application of each compound, its herbicidal effect on each weed and the influence on each crop were examined on the basis of visual observation and evaluated according to the Evaluation Criteria of the above Test Example 1. The results obtained are shown in Table 5-4.

In this connection, "No." described in the following Tables corresponds to "Compound No." described in the above Examples, and symbols represent the following meanings;

G: *Echinochloa crus-galli*,
H: *Setaria viridis*,
I: *Avena fatla*,
J: *Alopecurus myosuroides*,
K: *Abutilon theophrasti*,
L: *Xanthium pensylvanicum*,
M: *Amaranthus viridis*,
N: *Ipomoea purpurea*,
O: *Veronica persica*,
P: *Stellaria media*,
Q: *Digitaria adscendens*,
R: *Ambrosia artemisiaefolia*,
S: *Amaranthus retroflexus*,
T: *Chenopodium album*,
U: *Polygonum Blumei*,
 a: corn,
 b: rice,
 c: soybean,
 d: cotton,
 e: wheat,
 f: sugar beet.

[TABLE 5-1]

| Compound No | Rate (g/a) | A | B | C | D | E | F | b |
|---|---|---|---|---|---|---|---|---|
| 3 | 0.64 | 0 | 0 | 5 | 3 | 0 | 0 | 0 |
| 4 | 0.64 | 5 | 5 | 5 | 5 | 5 | 5 | 0 |
| 5 | 0.64 | 5 | 5 | 5 | 5 | 5 | 5 | 0 |
| 6 | 0.64 | 5 | 5 | 5 | 5 | 5 | 5 | 1 |
| 9 | 0.64 | 5 | 5 | 5 | 5 | 5 | 5 | 0 |
| 10 | 0.64 | 5 | 5 | 5 | 5 | 5 | 5 | 0 |
| 11 | 0.64 | 5 | 5 | 5 | 5 | 5 | 5 | 1 |
| 12 | 0.64 | 5 | 5 | 5 | 5 | 5 | 5 | 1 |
| 13 | 0.64 | 3 | 5 | 5 | 5 | 2 | 0 | 0 |
| 14 | 0.64 | 3 | 0 | 0 | 0 | 0 | 0 | 0 |
| 15 | 0.64 | 3 | 3 | 3 | 2 | 0 | 0 | 0 |
| 16 | 0.64 | 5 | 5 | 5 | 5 | 5 | 5 | 0 |
| 17 | 0.64 | 4 | 5 | 5 | 5 | 5 | 5 | 0 |
| 18 | 0.64 | 5 | 5 | 5 | 5 | 5 | 5 | 0 |
| 19 | 0.64 | 5 | 5 | 5 | 5 | 5 | 5 | 0 |
| 21 | 0.64 | 5 | 5 | 5 | 5 | 5 | 5 | 0 |
| 22 | 0.64 | 5 | 5 | 5 | 5 | — | 5 | 0 |
| 23 | 0.64 | 5 | 5 | 5 | 5 | — | 1 | 0 |
| 24 | 0.64 | 5 | 5 | 5 | 5 | — | — | 0 |
| 25 | 0.64 | 5 | 5 | 5 | 5 | — | 5 | 5 |
| 26 | 0.64 | 5 | 5 | 5 | 5 | — | 5 | 5 |
| 27 | 0.64 | 5 | 5 | 5 | 5 | — | 5 | 0 |
| 28 | 0.64 | 4 | 5 | 5 | 5 | — | 0 | 0 |
| 29 | 0.64 | 4 | 5 | 5 | 5 | — | 5 | 0 |
| 30 | 0.64 | 0 | 5 | 5 | 1 | — | 0 | 0 |
| 31 | 0.64 | 5 | 5 | 5 | 5 | — | 5 | 0 |
| 32 | 0.64 | 5 | 5 | 5 | 5 | — | 5 | 0 |
| 33 | 0.64 | 5 | 5 | 5 | 5 | 5 | 1 | 0 |
| 34 | 0.64 | 5 | 5 | 5 | 5 | 5 | 5 | 5 |
| 35 | 0.64 | 5 | 5 | 5 | 5 | 5 | 5 | 0 |
| 36 | 0.64 | 5 | 5 | 5 | 5 | 5 | 5 | 1 |
| 37 | 0.64 | 5 | 4 | 5 | 5 | 0 | — | 0 |
| 38 | 0.64 | 0 | 0 | 5 | 4 | 0 | 0 | 0 |
| 39 | 0.64 | 5 | 5 | 5 | 5 | 5 | 5 | 0 |
| 40 | 0.64 | 5 | 5 | 5 | 5 | 5 | 5 | 1 |
| 41 | 0.64 | 0 | 3 | 5 | 5 | 5 | 5 | 0 |
| 42 | 0.64 | 5 | 5 | 5 | 5 | 5 | 5 | 5 |
| 43 | 0.64 | 5 | 5 | 5 | 5 | 5 | 5 | 0 |
| 44 | 0.64 | 4 | 1 | 5 | 5 | 2 | 0 | 0 |
| 45 | 0.64 | 5 | 5 | 5 | 5 | 5 | 5 | 0 |
| 46 | 0.64 | 5 | 5 | 5 | 5 | 5 | 5 | 0 |
| 47 | 0.64 | 5 | 5 | 5 | 5 | 5 | 5 | 0 |
| 48 | 0.64 | 5 | 5 | 5 | 5 | 5 | 5 | 0 |
| 49 | 0.64 | 5 | 5 | 5 | 5 | 5 | 5 | 0 |
| 50 | 0.64 | 5 | 5 | 5 | 5 | 5 | 5 | 0 |
| 51 | 0.64 | 5 | 5 | 5 | 5 | 5 | 5 | 0 |
| 52 | 0.64 | 1 | 0 | 5 | — | — | — | 0 |
| 53 | 0.64 | 5 | 0 | 5 | — | — | — | 0 |
| 54 | 0.64 | 3 | 5 | 5 | — | — | — | 0 |
| 55 | 0.64 | 5 | 5 | 5 | — | — | — | 0 |
| 56 | 0.64 | 5 | 5 | 5 | — | — | — | 0 |
| 57 | 0.64 | 5 | 5 | 5 | — | — | — | 0 |
| 59 | 0.64 | 4 | 0 | 5 | — | — | — | 0 |
| 60 | 0.64 | 5 | 5 | 5 | — | — | — | 0 |
| 62 | 0.64 | 4 | 0 | 5 | — | — | — | 0 |
| 63 | 0.64 | 5 | 5 | 5 | — | — | — | 0 |
| 64 | 0.64 | 5 | 5 | 5 | — | — | — | 0 |
| 65 | 0.64 | 5 | 5 | 5 | — | — | — | 0 |
| 66 | 0.64 | 3 | 5 | 5 | — | — | — | 0 |

[TABLE 5-2]

| Compound No. | Rate (g/a) | A | B | C | D |
|---|---|---|---|---|---|
| 2 | 0.64 | 3 | 0 | 0 | 0 |
| 4 | 0.64 | 5 | 5 | 5 | 5 |
| 5 | 0.64 | 4 | 3 | 5 | 5 |
| 6 | 0.64 | 5 | 5 | 5 | 5 |
| 9 | 0.64 | 5 | 5 | 5 | 5 |
| 10 | 0.64 | 5 | 5 | 5 | 5 |
| 11 | 0.64 | 5 | 5 | 5 | 5 |
| 12 | 0.64 | 5 | 5 | 5 | 5 |

[TABLE 5-2]-continued

| Compound No. | Rate (g/a) | A | B | C | D |
|---|---|---|---|---|---|
| 13 | 0.64 | 0 | 0 | 2 | 4 |
| 16 | 0.64 | 5 | 5 | 5 | 5 |
| 17 | 0.64 | 5 | 5 | 5 | 5 |
| 18 | 0.64 | 5 | 5 | 5 | 5 |
| 19 | 0.64 | 5 | 5 | 5 | 5 |
| 20 | 0.64 | 0 | 0 | 4 | 0 |
| 21 | 0.64 | 5 | 5 | 5 | 5 |
| 22 | 0.64 | 5 | 5 | 5 | 5 |
| 23 | 0.64 | 0 | 5 | 5 | 5 |
| 24 | 0.64 | 0 | 0 | 4 | 5 |
| 25 | 0.64 | 5 | 5 | 5 | 5 |
| 26 | 0.64 | 5 | 5 | 5 | 5 |
| 27 | 0.64 | 3 | 3 | 5 | 5 |
| 28 | 0.64 | 0 | 2 | 0 | 5 |
| 29 | 0.64 | 0 | 0 | 5 | 5 |
| 30 | 0.64 | 0 | 1 | 4 | 5 |
| 31 | 0.64 | 5 | 2 | 5 | 5 |
| 32 | 0.64 | 5 | 5 | 5 | 5 |
| 33 | 0.64 | 0 | 5 | 5 | 5 |
| 34 | 0.64 | 5 | 5 | 5 | 5 |
| 35 | 0.64 | 5 | 5 | 5 | 5 |
| 36 | 0.64 | 4 | 5 | 4 | 5 |
| 37 | 0.64 | 1 | 3 | 3 | 4 |
| 38 | 0.64 | 3 | 0 | 5 | 2 |
| 39 | 0.64 | 5 | 5 | 5 | 5 |
| 40 | 0.64 | 5 | 5 | 5 | 5 |
| 41 | 0.64 | 0 | 1 | 3 | 5 |
| 42 | 0.64 | 5 | 5 | 5 | 5 |
| 43 | 0.64 | 5 | 5 | 5 | 5 |
| 44 | 0.64 | 0 | 0 | 5 | 0 |
| 45 | 0.64 | 5 | 5 | 5 | 5 |
| 46 | 0.64 | 4 | 3 | 4 | 5 |
| 47 | 0.64 | 5 | 5 | 5 | 5 |
| 48 | 2.52 | 5 | 5 | 5 | 5 |
| 49 | 2.52 | 5 | 5 | 5 | 5 |
| 50 | 2.52 | 5 | 5 | 5 | 5 |
| 51 | 0.64 | 0 | 5 | 5 | 5 |
| 53 | 0.64 | 5 | 3 | 5 | — |
| 54 | 0.64 | 0 | 5 | 5 | — |
| 55 | 0.64 | 5 | 5 | 5 | — |
| 56 | 0.64 | 3 | 0 | 0 | — |
| 57 | 0.64 | 4 | 3 | 5 | — |
| 60 | 0.64 | 0 | 3 | 5 | — |
| 62 | 0.64 | 0 | 0 | 5 | — |
| 63 | 0.64 | 1 | 0 | 5 | — |
| 64 | 0.64 | 5 | 5 | 5 | — |
| 65 | 0.64 | 2 | 5 | 5 | — |
| 66 | 0.64 | 3 | 5 | 5 | — |

[TABLE 5-3]

| Compound No. | Rate (g/a) | G | H | I | J | K | L | M | N | O | P | Q | R | S | T | U | a | b | c | d | e | f |
|---|---|---|---|---|---|---|---|---|---|---|---|---|---|---|---|---|---|---|---|---|---|---|
| 2 | 1.6 | 0 | 0 | 0 | 0 | 2 | 1 | 2 | 1 | 0 | 0 | — | — | — | — | — | 0 | 0 | 0 | 0 | 0 | 0 |
| 3 | 1.6 | 0 | 0 | 0 | 0 | 4 | 1 | 0 | 5 | 4 | 1 | — | — | — | — | — | 0 | 0 | 0 | 0 | 0 | 4 |
| 4 | 1.6 | 5 | 5 | 5 | 5 | 1 | 5 | 5 | 5 | 5 | 5 | — | — | — | — | — | 5 | 1 | 0 | 1 | 0 | 5 |
| 5 | 1.6 | 5 | 5 | 5 | 5 | 5 | 4 | 5 | 5 | 5 | 5 | — | — | — | — | — | 1 | 0 | 1 | 1 | 3 | 5 |
| 6 | 1.6 | 5 | 5 | 3 | 5 | 5 | 5 | 5 | 5 | 5 | 5 | — | — | — | — | — | 4 | 5 | 5 | 0 | 1 | 5 |
| 9 | 1.6 | 5 | 5 | 1 | 3 | 5 | 5 | 5 | 5 | 5 | 5 | — | — | — | — | — | 1 | 1 | 0 | 4 | 0 | 5 |
| 10 | 1.6 | 1 | 5 | 3 | 2 | 1 | 5 | 5 | 5 | 5 | 2 | — | — | — | — | — | 0 | 0 | 1 | 0 | 0 | 5 |
| 11 | 1.6 | 5 | 5 | 5 | 4 | 5 | 2 | 5 | 5 | 5 | 5 | — | — | — | — | — | 0 | 4 | 0 | 0 | 0 | 5 |
| 12 | 1.6 | 5 | 5 | 5 | 5 | 5 | 4 | 5 | 5 | 5 | 5 | — | — | — | — | — | 3 | 4 | 2 | 0 | 5 | 5 |
| 13 | 1.6 | 1 | 5 | 0 | 0 | 5 | 0 | 5 | 0 | 5 | 5 | — | — | — | — | — | 0 | 0 | 0 | 0 | 0 | 5 |
| 16 | 1.6 | 4 | 4 | 2 | 2 | 5 | 5 | 5 | 5 | 5 | 4 | — | — | — | — | — | 1 | 0 | 0 | 0 | 0 | 5 |
| 17 | 1.6 | 3 | 3 | 0 | 0 | 5 | 1 | 5 | — | 5 | 1 | — | — | — | — | — | 0 | 0 | 0 | 0 | 0 | 5 |
| 18 | 1.6 | 4 | 3 | 1 | 1 | 4 | 0 | 5 | 0 | 5 | 3 | — | — | — | — | — | 0 | 1 | 0 | 0 | 0 | 2 |
| 19 | 1.6 | 5 | 5 | 1 | 3 | 5 | 0 | 5 | 0 | 5 | 5 | — | — | — | — | — | 1 | 1 | 0 | 0 | 0 | 5 |
| 20 | 1.6 | 5 | 5 | 0 | 0 | 0 | 0 | 5 | 4 | 1 | 1 | — | — | — | — | — | 0 | 0 | 0 | 0 | 0 | 5 |
| 21 | 1.6 | 5 | 5 | 5 | 5 | 5 | 5 | 5 | 5 | 5 | 5 | — | — | — | — | — | 2 | 3 | 3 | 4 | 4 | 5 |
| 22 | 1.6 | 5 | 5 | 5 | 5 | 5 | 1 | 2 | 4 | 4 | 3 | — | — | — | — | — | 1 | 1 | 1 | 0 | 4 | 5 |
| 23 | 1.6 | 0 | 0 | 0 | 0 | 5 | 0 | 5 | 0 | 0 | 0 | — | — | — | — | — | 0 | 0 | 0 | 0 | 0 | 5 |
| 24 | 1.6 | 2 | 3 | 3 | 1 | 5 | 0 | 3 | 0 | 5 | 5 | — | — | — | — | — | 0 | 0 | 0 | 0 | 0 | 5 |

[TABLE 5-3]-continued

| Compound No. | Rate (g/a) | G | H | I | J | K | L | M | N | O | P | Q | R | S | T | U | a | b | c | d | e | f |
|---|---|---|---|---|---|---|---|---|---|---|---|---|---|---|---|---|---|---|---|---|---|---|
| 25 | 1.6 | 5 | 5 | 5 | 5 | 5 | 5 | 5 | 5 | 5 | 5 | — | — | — | — | — | 5 | 5 | 5 | 5 | 5 | 5 |
| 26 | 1.6 | 5 | 5 | 5 | 5 | 5 | 3 | 5 | 5 | 5 | 5 | — | — | — | — | — | 2 | 4 | 1 | 0 | 2 | 5 |
| 27 | 1.6 | 3 | 1 | 0 | 0 | 5 | 0 | 5 | 5 | 5 | 0 | — | — | — | — | — | 0 | 0 | 0 | 0 | 0 | 5 |
| 28 | 1.6 | 3 | 1 | 0 | 1 | 5 | 1 | 5 | 3 | 2 | 1 | — | — | — | — | — | 0 | 0 | 0 | 0 | 0 | 5 |
| 29 | 1.6 | 2 | 2 | 0 | 0 | 5 | 2 | 5 | 5 | 3 | 1 | — | — | — | — | — | 0 | 0 | 0 | 0 | 0 | 5 |
| 30 | 1.6 | 1 | 4 | 0 | 1 | 5 | 2 | 5 | 3 | 3 | 3 | — | — | — | — | — | 0 | 0 | 0 | 0 | 0 | 5 |
| 31 | 1.6 | 5 | 5 | 5 | 4 | 5 | 4 | 5 | 4 | 5 | 5 | — | — | — | — | — | 5 | 3 | 1 | 1 | 4 | 5 |
| 32 | 1.6 | 4 | 5 | 4 | 2 | 5 | 3 | 5 | 5 | 5 | 5 | — | — | — | — | — | 1 | 2 | 1 | 0 | 0 | 5 |
| 33 | 1.6 | 2 | 2 | 0 | 0 | 2 | 2 | 3 | 3 | 5 | 0 | — | — | — | — | — | 0 | 0 | 0 | 0 | 0 | 5 |
| 34 | 1.6 | 5 | 5 | 5 | 5 | 5 | 5 | 5 | 5 | 5 | 5 | — | — | — | — | — | 5 | 5 | 5 | 5 | 5 | 5 |
| 35 | 1.6 | 5 | 5 | 4 | 3 | 5 | 5 | 5 | 5 | 5 | 5 | — | — | — | — | — | 3 | 5 | 3 | 2 | 3 | 5 |
| 36 | 1.6 | 5 | 5 | 5 | 4 | 5 | 1 | 5 | 3 | 5 | 5 | — | — | — | — | — | 0 | 1 | 0 | 0 | 0 | 5 |
| 37 | 1.6 | 0 | 0 | 0 | 0 | 4 | 0 | 5 | 0 | 0 | 1 | — | — | — | — | — | 0 | 0 | 0 | 0 | 0 | 0 |
| 39 | 1.6 | 5 | 5 | 5 | 5 | 5 | 5 | 5 | 5 | 5 | 5 | — | — | — | — | — | 3 | 3 | 2 | 2 | 5 | 5 |
| 40 | 1.6 | 5 | 5 | 5 | 5 | 5 | 5 | 5 | 5 | 5 | 5 | — | — | — | — | — | 5 | 5 | 4 | 5 | 5 | 5 |
| 41 | 1.6 | 1 | 4 | 0 | 0 | 4 | 0 | 0 | 0 | 1 | 0 | — | — | — | — | — | 0 | 0 | 0 | 0 | 0 | 0 |
| 42 | 1.6 | 5 | 5 | 5 | 5 | 5 | 4 | 5 | 5 | 5 | 5 | — | — | — | — | — | 3 | 5 | 3 | 4 | 5 | 5 |
| 43 | 1.6 | 5 | 5 | 4 | 5 | 5 | 5 | 5 | 5 | 5 | 5 | — | — | — | — | — | 4 | 5 | 3 | 3 | 5 | 5 |
| 44 | 1.6 | 0 | 0 | 0 | 0 | 1 | 0 | 3 | 0 | 0 | 0 | — | — | — | — | — | 0 | 0 | 0 | 0 | 0 | 0 |
| 45 | 1.6 | 5 | 5 | 5 | 5 | 5 | 5 | 5 | 5 | 5 | 5 | — | — | — | — | — | 5 | 5 | 3 | 4 | 4 | 5 |
| 46 | 1.6 | 5 | 5 | 0 | 1 | 5 | 5 | 5 | 5 | 5 | 5 | — | — | — | — | — | 2 | 1 | 0 | 5 | 0 | 5 |
| 47 | 1.6 | 5 | 5 | 5 | 5 | 5 | 1 | 5 | 5 | 5 | 5 | — | — | — | — | — | 3 | 4 | 2 | 0 | 3 | 3 |
| 48 | 1.6 | 5 | 5 | 2 | 5 | 5 | 0 | 5 | 4 | 5 | 5 | — | — | — | — | — | 1 | 0 | 0 | 0 | 1 | 5 |
| 49 | 1.6 | 5 | 5 | 0 | 0 | 5 | 3 | 5 | 5 | 5 | 5 | — | — | — | — | — | 1 | 2 | 0 | 3 | 0 | 5 |
| 50 | 1.6 | 0 | 5 | 0 | 0 | 5 | 5 | 5 | 5 | 5 | 5 | — | — | — | — | — | 0 | 0 | 0 | 0 | 0 | 5 |
| 51 | 1.6 | 2 | 4 | 0 | 0 | 5 | 5 | 5 | 5 | 4 | 5 | — | — | — | — | — | 0 | 2 | 0 | 5 | 0 | 5 |
| 52 | 1.6 | 0 | 0 | 0 | 0 | 4 | 0 | 5 | 0 | 1 | 1 | — | — | — | — | — | 0 | 0 | 0 | 0 | 0 | 4 |
| 53 | 1.6 | 5 | 4 | 5 | 5 | 5 | 3 | 5 | 5 | 5 | 5 | — | — | — | — | — | 1 | 4 | 1 | 1 | 5 | 5 |
| 54 | 1.6 | 0 | 0 | 0 | 0 | 0 | 5 | 0 | 5 | 0 | 0 | — | — | — | — | — | 0 | 0 | 0 | 0 | 0 | 0 |
| 55 | 1.6 | 5 | 3 | 0 | 0 | 1 | 0 | 5 | 0 | 0 | 0 | — | — | — | — | — | 1 | 0 | 0 | 0 | 0 | 0 |
| 56 | 1.6 | 0 | 0 | 0 | 0 | 0 | 0 | 5 | 0 | 0 | 0 | — | — | — | — | — | 0 | 0 | 0 | 0 | 0 | 0 |
| 57 | 1.6 | 5 | 5 | 5 | 5 | 5 | 1 | 5 | 5 | 5 | 5 | — | — | — | — | — | 2 | 5 | 1 | 1 | 4 | 5 |
| 58 | 1.6 | 0 | 5 | 1 | 0 | 5 | — | 5 | 5 | 4 | 0 | — | — | — | — | — | 2 | 0 | 2 | 5 | 0 | 3 |
| 59 | 1.6 | 4 | 0 | 0 | — | 0 | 0 | 0 | 0 | 3 | 0 | — | — | — | — | — | 0 | 0 | 0 | 0 | 0 | 0 |
| 60 | 1.6 | 5 | 5 | 0 | 0 | 5 | 3 | 5 | 4 | 5 | 5 | — | — | — | — | — | 0 | 0 | 1 | 1 | 0 | 5 |
| 61 | 1.6 | — | 3 | — | 0 | 5 | — | — | — | 0 | 0 | 5 | 4 | 4 | 5 | — | 0 | — | 0 | 0 | 0 | 5 |
| 62 | 1.6 | — | 0 | 0 | 0 | 0 | — | — | — | — | 4 | 3 | 0 | 3 | 5 | — | 0 | 0 | — | 0 | 0 | 5 |
| 63 | 1.6 | — | 4 | 0 | 0 | 1 | — | — | — | — | 5 | 5 | 4 | 0 | 4 | — | — | 0 | — | 0 | 0 | 3 |
| 64 | 1.6 | — | 5 | 5 | 5 | 5 | — | — | — | — | 5 | 5 | 5 | 5 | 5 | 5 | 2 | — | 1 | 2 | 4 | 5 |
| 65 | 1.6 | — | 5 | 0 | 0 | 5 | — | — | — | — | 5 | 5 | 5 | 5 | 5 | 0 | 1 | — | 1 | 1 | 0 | 5 |
| 66 | 1.6 | — | 4 | 0 | 0 | 0 | — | — | — | — | 5 | 5 | 5 | 3 | 2 | 2 | — | 0 | — | 0 | 0 | 5 |

[TABLE 5-4]

| Compound No. | Rate (g/a) | G | H | I | J | K | L | M | N | O | P | Q | R | S | T | U | a | b | c | d | e | f |
|---|---|---|---|---|---|---|---|---|---|---|---|---|---|---|---|---|---|---|---|---|---|---|
| 1 | 1.6 | 0 | 0 | 0 | 0 | 1 | 0 | 0 | 0 | 0 | 0 | — | — | — | — | — | 0 | 0 | 0 | 0 | 0 | 0 |
| 2 | 1.6 | 0 | 0 | 0 | 0 | 5 | 1 | 5 | 4 | 0 | 0 | — | — | — | — | — | 0 | 0 | 0 | 0 | 0 | 0 |
| 3 | 1.6 | 0 | 1 | 0 | 1 | 5 | 2 | 4 | 4 | 5 | 4 | — | — | — | — | — | 0 | 0 | 0 | 0 | 0 | 3 |
| 4 | 1.6 | 4 | 4 | 5 | 5 | 5 | 5 | 5 | 5 | 5 | 5 | — | — | — | — | — | 1 | 2 | 0 | 1 | 4 | 5 |
| 5 | 1.6 | 3 | 3 | 1 | 5 | 5 | 5 | 5 | 5 | 5 | 5 | — | — | — | — | — | 0 | 0 | 2 | 1 | 0 | 4 |
| 6 | 1.6 | 5 | 5 | 3 | 5 | 5 | 5 | 5 | 5 | 5 | 5 | — | — | — | — | — | 2 | 2 | 5 | 1 | 2 | 5 |
| 9 | 1.6 | 5 | 5 | 1 | 5 | 5 | 5 | 5 | 5 | 5 | 5 | — | — | — | — | — | 2 | 1 | 1 | 5 | 0 | 5 |
| 10 | 1.6 | 4 | 5 | 1 | 3 | 5 | 5 | 5 | 5 | 5 | 5 | — | — | — | — | — | 1 | 0 | 4 | 5 | 1 | 5 |
| 11 | 1.6 | 5 | 5 | 5 | 5 | 5 | 5 | 5 | 5 | 5 | 5 | — | — | — | — | — | 3 | 1 | 5 | 5 | 2 | 5 |
| 12 | 1.6 | 5 | 5 | 5 | 5 | 5 | 5 | 5 | 5 | 5 | 5 | — | — | — | — | — | 5 | 5 | 5 | 5 | 5 | 5 |
| 13 | 1.6 | 2 | 5 | 1 | 2 | 5 | 5 | 5 | 5 | 5 | 5 | — | — | — | — | — | 1 | 0 | 2 | 1 | 0 | 5 |
| 14 | 1.6 | 0 | 0 | 0 | 0 | 1 | 2 | 5 | 3 | 0 | 0 | — | — | — | — | — | 0 | 0 | 0 | 0 | 0 | 0 |
| 15 | 1.6 | 3 | 1 | 0 | 1 | 5 | 2 | 5 | 5 | 5 | 5 | — | — | — | — | — | 0 | 0 | 0 | 5 | 0 | 5 |
| 16 | 1.6 | 3 | 3 | 2 | 5 | 5 | 5 | 5 | 5 | 5 | 5 | — | — | — | — | — | 2 | 0 | 1 | 5 | 0 | 5 |
| 17 | 1.6 | 3 | 5 | 2 | 5 | 5 | 5 | 5 | 5 | 5 | 5 | — | — | — | — | — | 1 | 0 | 1 | 5 | 0 | 5 |
| 18 | 1.6 | 5 | 4 | 4 | 4 | 5 | 5 | 5 | 5 | 5 | 5 | — | — | — | — | — | 2 | 3 | 2 | 5 | 1 | 5 |
| 19 | 1.6 | 3 | 5 | 5 | 4 | 5 | 5 | 5 | 5 | 5 | 5 | — | — | — | — | — | 3 | 2 | 4 | 5 | 1 | 5 |
| 20 | 1.6 | 3 | 3 | 1 | 1 | 5 | 5 | 5 | 5 | 5 | 5 | — | — | — | — | — | 1 | 0 | 1 | 5 | 0 | 5 |
| 21 | 1.6 | 5 | 5 | 5 | 5 | 5 | 5 | 5 | 5 | 5 | 5 | — | — | — | — | — | 1 | 3 | 5 | 5 | 3 | 5 |
| 22 | 1.6 | 5 | 5 | 4 | 3 | 5 | 5 | 5 | 5 | 5 | 5 | — | — | — | — | — | 1 | 1 | 3 | 5 | 3 | 5 |
| 23 | 1.6 | 5 | 5 | 1 | 1 | 5 | 5 | 5 | 5 | 5 | 1 | — | — | — | — | — | 1 | 0 | 1 | 5 | 0 | 5 |
| 24 | 1.6 | 2 | 5 | 1 | 2 | 5 | 5 | 5 | 5 | 5 | 1 | — | — | — | — | — | 1 | 0 | 1 | 5 | 0 | 5 |
| 25 | 1.6 | 5 | 5 | 5 | 5 | 5 | 5 | 5 | 5 | 5 | 5 | — | — | — | — | — | 5 | 5 | 5 | 5 | 5 | 5 |
| 26 | 1.6 | 5 | 5 | 5 | 5 | 5 | 5 | 5 | 5 | 5 | 5 | — | — | — | — | — | 4 | 4 | 5 | 5 | 3 | 5 |
| 27 | 1.6 | 5 | 5 | 3 | 3 | 5 | 5 | 4 | 5 | 5 | 5 | — | — | — | — | — | 1 | 0 | 5 | 5 | 0 | 5 |
| 28 | 1.6 | 3 | 3 | 1 | 1 | 5 | 5 | 5 | 5 | 5 | 5 | — | — | — | — | — | 1 | 0 | 0 | 5 | 0 | 5 |

[TABLE 5-4]-continued

| Compound No. | Rate (g/a) | G | H | I | J | K | L | M | N | O | P | Q | R | S | T | U | a | b | c | d | e | f |
|---|---|---|---|---|---|---|---|---|---|---|---|---|---|---|---|---|---|---|---|---|---|---|
| 29 | 1.6 | 1 | 4 | 2 | 2 | 5 | 5 | 5 | 5 | 5 | 5 | — | — | — | — | — | 1 | 0 | 0 | 5 | 0 | 5 |
| 30 | 1.6 | 0 | 3 | 0 | 1 | 5 | 0 | 1 | 2 | 2 | 2 | — | — | — | — | — | 0 | 0 | 0 | 0 | 0 | 5 |
| 31 | 1.6 | 5 | 5 | 5 | 5 | 5 | 5 | 5 | 5 | 5 | 5 | — | — | — | — | — | 5 | 5 | 5 | 5 | 5 | 5 |
| 32 | 1.6 | 5 | 5 | 1 | 4 | 5 | 5 | 5 | 5 | 5 | 5 | — | — | — | — | — | 3 | 4 | 2 | 1 | 2 | 5 |
| 33 | 1.6 | 5 | 5 | 2 | 1 | 5 | 5 | 5 | 5 | 5 | 5 | — | — | — | — | — | 0 | 0 | 1 | 5 | 0 | 4 |
| 34 | 1.6 | 5 | 5 | 5 | 5 | 5 | 5 | 5 | 5 | 5 | 5 | — | — | — | — | — | 5 | 5 | 5 | 5 | 5 | 5 |
| 35 | 1.6 | 5 | 5 | 5 | 4 | 5 | 5 | 5 | 5 | 5 | 5 | — | — | — | — | — | 2 | 2 | 4 | 5 | 5 | 5 |
| 36 | 1.6 | 4 | 5 | 2 | 5 | 5 | 5 | 5 | 5 | 5 | 5 | — | — | — | — | — | 1 | 1 | 1 | 5 | 0 | 5 |
| 37 | 1.6 | 1 | 1 | 1 | 1 | 5 | 3 | 5 | 5 | 5 | 5 | — | — | — | — | — | 0 | 0 | 1 | 4 | 0 | 5 |
| 38 | 1.6 | 1 | 1 | 1 | 0 | 3 | 1 | 1 | 1 | 3 | 2 | — | — | — | — | — | 0 | 0 | 1 | 0 | 0 | 0 |
| 39 | 1.6 | 5 | 5 | 3 | 5 | 5 | 5 | 5 | 5 | 5 | 5 | — | — | — | — | — | 5 | 5 | 5 | 5 | 5 | 5 |
| 40 | 1.6 | 5 | 5 | 5 | 5 | 5 | 5 | 5 | 5 | 5 | 5 | — | — | — | — | — | 5 | 5 | 4 | 5 | 5 | 5 |
| 41 | 1.6 | 0 | 4 | — | 1 | 5 | 1 | 1 | 1 | 5 | 4 | — | — | — | — | — | 0 | 0 | 1 | 0 | 0 | 1 |
| 42 | 1.6 | 5 | 5 | 5 | 5 | 5 | 5 | 5 | 5 | 5 | 5 | — | — | — | — | — | 5 | 5 | 5 | 5 | 5 | 5 |
| 43 | 1.6 | 5 | 5 | 4 | 5 | 5 | 5 | 5 | 5 | 5 | 5 | — | — | — | — | — | 3 | 5 | 5 | 5 | 5 | 5 |
| 44 | 1.6 | 1 | 1 | 0 | 0 | 5 | 5 | 1 | 3 | 2 | 1 | — | — | — | — | — | 0 | 0 | 0 | 0 | 0 | 1 |
| 45 | 1.6 | 5 | 5 | 5 | 5 | 5 | 5 | 5 | 5 | 5 | 5 | — | — | — | — | — | 3 | 4 | 5 | 5 | 5 | 5 |
| 46 | 1.6 | 4 | 4 | 3 | 5 | 5 | 5 | 5 | 3 | 5 | 5 | — | — | — | — | — | 1 | 0 | 0 | 5 | 0 | 5 |
| 47 | 1.6 | 5 | 5 | 4 | 5 | 5 | 5 | 5 | 5 | 5 | 5 | — | — | — | — | — | 3 | 5 | 5 | 5 | 2 | 5 |
| 48 | 1.6 | 4 | 5 | 3 | 3 | 5 | 5 | 5 | 5 | 5 | 5 | — | — | — | — | — | 1 | 1 | 3 | 5 | 1 | 5 |
| 49 | 1.6 | 5 | 5 | 1 | 3 | 5 | 5 | 5 | 5 | 5 | 5 | — | — | — | — | — | 1 | 0 | 0 | 5 | 0 | 5 |
| 50 | 1.6 | 1 | 3 | 1 | 3 | 5 | 5 | 5 | 3 | 5 | 5 | — | — | — | — | — | 0 | 0 | 0 | 5 | 0 | 5 |
| 51 | 1.6 | 1 | 3 | 0 | 2 | 5 | 5 | 5 | 3 | 5 | 5 | — | — | — | — | — | 0 | 0 | 0 | 5 | 0 | 5 |
| 52 | 1.6 | 0 | 0 | 0 | 0 | 4 | 0 | 2 | 1 | 4 | 1 | — | — | — | — | — | 0 | 0 | 0 | 0 | 0 | 0 |
| 53 | 1.6 | 4 | 4 | 4 | 5 | 5 | 5 | 5 | 5 | 5 | 5 | — | — | — | — | — | 2 | 2 | 2 | 2 | 3 | 5 |
| 54 | 1.6 | 0 | 0 | 2 | 0 | 5 | 5 | 4 | 5 | 5 | 5 | — | — | — | — | — | 0 | 0 | 1 | 5 | 0 | 5 |
| 55 | 1.6 | 2 | 2 | 0 | 0 | 5 | 1 | 5 | 1 | 5 | 0 | — | — | — | — | — | 1 | 0 | 0 | 3 | 2 | 5 |
| 56 | 1.6 | 0 | 0 | 1 | 0 | 3 | 1 | 5 | 0 | 5 | 0 | — | — | — | — | — | 0 | 0 | 0 | 0 | 0 | 0 |
| 57 | 1.6 | 4 | 5 | 3 | 5 | 5 | 3 | 3 | 4 | 5 | 4 | — | — | — | — | — | 4 | 1 | 1 | 1 | 2 | 5 |
| 58 | 1.6 | 0 | 0 | 0 | 0 | 5 | 5 | 0 | 5 | 5 | 0 | — | — | — | — | — | 0 | 0 | 0 | 0 | 0 | 1 |
| 59 | 1.6 | 4 | 1 | 0 | 1 | 5 | 3 | 0 | 0 | 5 | 5 | — | — | — | — | — | 0 | 0 | 0 | 0 | 0 | 0 |
| 60 | 1.6 | 0 | 0 | 1 | 1 | 5 | 5 | 1 | 3 | 5 | 5 | — | — | — | — | — | 0 | 0 | 1 | 1 | 0 | 5 |
| 61 | 1.6 | — | 0 | 0 | 0 | 4 | — | — | — | 5 | 0 | 0 | 0 | 3 | — | — | 0 | — | 0 | 0 | 0 | 4 |
| 62 | 1.6 | — | 1 | 5 | 4 | 5 | — | — | — | 5 | 5 | 1 | 5 | 5 | — | — | 0 | — | 2 | 5 | 1 | 5 |
| 63 | 1.6 | — | 3 | 2 | 1 | 5 | — | — | — | 5 | 5 | 0 | 5 | 5 | — | — | 1 | — | 1 | 5 | 0 | 5 |
| 64 | 1.6 | — | 5 | 3 | 5 | 5 | — | — | — | 5 | 5 | 5 | 5 | 5 | 5 | 5 | 1 | — | 1 | 5 | 4 | 5 |
| 65 | 1.6 | — | 5 | 2 | 2 | 5 | — | — | — | 5 | 5 | 5 | 5 | 5 | 5 | 0 | — | 2 | 5 | 0 | 5 |   |
| 66 | 1.6 | — | 2 | 0 | 0 | 4 | — | — | — | 2 | 2 | 2 | 1 | 5 | — | 5 | 0 | — | 1 | 0 | 0 | 1 |

What is claimed is:

1. A compound having the formula (I) or a salt thereof:

(I)

wherein:

Rf represents $(C_1-C_4)$haloalkyl;

X~Y represents:

N=N,

C(Ra)=C(Rb), wherein Ra and Rb each independently represents hydrogen, halogen, $(C_1-C_4)$alkyl, $(C_1-C_4)$alkoxy, $(C_1-C_4)$haloalkyl, hydroxy, amino, mercapto, carboxyl, hydroxymethyl, carbamoyl, formyl, $(C_1-C_4)$alkylcarbonyl, $(C_1-C_4)$alkoxycarbonyl, $(C_1-C_4)$alkylamino, $(C_2-C_6)$alkenyl, $(C_2-C_6)$alkynyl, $(C_1-C_4)$alkymercapto, $(C_3-C_6)$alkenylamino, $(C_3-C_6)$alkynylamino, benzyloxy, benzylamino, $(C_1-C_4)$alkylsulfinyl, $(C_1-C_4)$alkylsulfonyl or pyridyl or phenyl, which is optionally substituted with halogen, $(C_1-C_4)$alkyl, $(C_1-C_4)$alkoxy, $(C_1-C_4)$haloalkyl, $(C_1-C_4)$haloalkoxy or phenyl, C(Ra)=N, wherein Ra is as defined above, N=C(Ra), wherein Ra is as defined above, CH(Ra)CH(Rb), wherein Ra and Rb are each as defined above, or $CH_2CH_2CH_2$, CH=$CHCH_2$ or $CH_2CH$=CH, or NHC(Ra)Rb, wherein Ra and Rb are each as defined above, C(Ra)(Rb)NH, wherein Ra and Rb are each as defined above, or C(=O)C(=O), $CH_2C$(=O)NH or $CH_2CH_2SO_2$, or C(=O)CH(Ra), wherein Ra is as defined above, CH(Ra)C(=O), wherein Ra is as defined above, or C(=O)NH, C(=S)NH, NHC(=O) or NHC(=S), or C(=O)C(Ra)=N, wherein Ra is as defined above, C(=O)C(Ra)=C(Rb), wherein Ra and Rb are each as defined above, C(Ra)=C(Rb)C(=O), wherein Ra and Rb are each as defined above, N=C(Ra)C(=O), wherein Ra is as defined above, CH(Ra)C(=O)NH, wherein Ra is as defined above, C(=O)N(Ra)C(=O), wherein Ra is as defined above, C(Ra)=NC(=O), wherein Ra is as defined above, C(Ra)O, wherein Ra is as defined above, or C(=O)O, OC(=O) or SC(=O);

A represents nitrogen or CH;

Z represents:

oxygen or sulfur,

NRc, wherein Rc is hydrogen, $(C_1-C_4)$alkyl, $(C_1-C_4)$alkoxycarbonyl or $(C_1-C_4)$alkoxycarbonylmethyl group, or phenyl which is optionally substituted with halogen, $(C_1-C_4)$alkyl, $(C_1-C_4)$alkoxy or $(C_1-C_4)$haloalkyl, or NNHRc, wherein Rc is as defined above;

Rg represents hydrogen, halogen, cyano, $(C_1-C_6)$alkoxycarbonyl, $(C_3-C_6)$alkenyl, $(C_3-C_6)$alkynyl or $(C_1-C_4)$alkyl;

R1, R2, R3, R4 and R5 each independently represents:

hydrogen, halogen, nitro, cyano, thiocarbamoyl, carbamoyl, mercapto, hydroxyl, amino, formyl, carboxyl, vinyl, ethynyl, trimethylsilylethynyl, cyanomethyl, sulfamoyl, $(C_1-C_8)$alkyl, $(C_3-C_8)$alkenyl, $(C_1-C_4)$alkylsulfonyl, $(C_3-C_8)$alkynyl, $(C_3-C_8)$cycloalkyl, $(C_1-C_4)$haloalkyl, $(C_3-C_8)$haloalkenyl, $(C_3-C_8)$haloalkynyl, $(C_1-C_4)$acyl, $(C_1-C_4)$alkoxy$(C_1-C_2)$alkyl or $(C_1-C_4)$alkylsulfinyl, or phenyl which is optionally substituted with halogen, $(C_1-C_4)$haloalkyl, $(C_1-C_4)$alkyl, $(C_1-C_4)$alkoxy, $(C_1-C_4)$haloalkoxy, methanesulfonyl, $(C_1-C_4)$alkoxycarbonyl, nitro, hydroxyl, amino or cyano, or a group —O—CH($CH_3$)COR$_1$–$C_4$)alkyl or —O—CH$_2$COR$_1$–$C_4$)alkyl, a group —Q-(optionally substituted phenyl group), wherein Q is a saturated or unsaturated $(C_1-C_6)$ alkylene chain which is optionally branched and substituted with a halogen atom, and the optionally substituted phenyl group is as defined above, a group —O—Q-(optionally substituted phenyl group), wherein Q and the optionally substituted phenyl group are each as defined above, a group —S—Q-(optionally substituted phenyl group), wherein Q and the optionally substituted phenyl group are each as defined above, a group —NH—Q-(optionally substituted phenyl group), wherein Q and the optionally substituted phenyl group are each as defined above, a group —O-(optionally substituted phenyl group), wherein the optionally substituted phenyl group is as defined above, a group —S-(optionally substituted phenyl group), wherein the optionally substituted phenyl group is as defined above, a group —NH-(optionally substituted phenyl group), wherein the optionally substituted phenyl group is as defined above, —O—R11, wherein R11 represents $(C_1-C_8)$alkyl, $(C_3-C_8)$cycloalkyl, $(C_3-C_8)$cycloalkyl$(C_1-C_4)$alkyl, $(C_3-C_8)$alkenyl, $(C_3-C_8)$alkynyl, $(C_3-C_8)$haloalkenyl, $(C_1-C_4)$haloalkylcarbonyl, $(C_3-C_8)$haloalkynyl, $(C_1-C_4)$haloalkyl, $(C_1-C_4)$alkoxy$(C_1-C_4)$alkyl, cyanomethyl or $(C_1-C_4)$acyl, —NH—R11, wherein R11 is as defined above, —S—R11, wherein R11 is as defined above, or a group —CON$[(C_1-C_4)$alkyl$]_2$ or —CONH$[(C_1-C_4)$alkyl], or —CO$_2$R12, wherein R12 represents $(C_1-C_8)$alkyl, $(C_3-C_8)$cycloalkyl, $(C_3-C_8)$alkenyl or $(C_3-C_8)$alkynyl, or optionally substituted phenyl, wherein the optionally substituted phenyl is as defined above, or a group —Q-(optionally substituted phenyl group), wherein Q and the optionally substituted phenyl group are each as defined above, or oxetan-3-yl, $(C_1-C_4)$alkoxycarbonylmethyl or $[(C_1-C_4)$alkyl$]_2$amino group, —CONHR12, wherein R12 is as defined above, —Q—CO$_2$R12, wherein Q and R12 are each as defined above, —O—Q—CO$_2$R12, wherein Q and R12 are each as defined above, —NH—Q—CO$_2$R12, wherein Q and R12 are each as defined above, —S—Q—CO$_2$R12, wherein Q and R12 are each as defined above, —NHSO$_2$R13, wherein R13 represents $(C_1-C_8)$alkyl, $(C_1-C_4)$haloalkyl, $(C_3-C_6)$cycloalkyl, $(C_3-C_8)$alkenyl, $(C_3-C_8)$alkynyl, benzyl or phenyl, —N(SO$_2$R13)$_2$, wherein R13 is as defined above, —CONHSO$_2$R14, wherein R14 is $(C_1-C_4)$alkyl or $(C_1-C_4)$haloalkyl, —N(R15)SO$_2$R13, wherein R13 is as defined above and R15 represents a $(C_1-C_6)$alkyl, $(C_3-C_8)$alkenyl, $(C_3-C_8)$alkynyl, $(C_1-C_4)$haloalkyl, $(C_3-C_8)$haloalkenyl, $(C_3-C_8)$haloalkynyl, $(C_1-C_6)$acyl, fornyl, cyano $(C_1-C_4)$alkyl, $(C_1-C_4)$alkoxy$(C_1-C_4)$alkyl or $(C_1-C_4)$alkoxycarbonyl, or a group —C(=O)(optionally substituted phenyl group), wherein the optionally substituted phenyl group is as defined above, —NHCO$_2$R16, wherein R16 represents $(C_1-C_6)$alkyl, $(C_3-C_8)$alkenyl, $(C_3-C_8)$alkynyl, $(C_1-C_4)$haloalkyl or phenyl, or a group —Q-(optionally substituted phenyl group), wherein Q and the optionally substituted phenyl group are each as defined above, —O—CO$_2$R16, wherein R16 is as defined above, —N(R15)CO$_2$R16, wherein R15 and R16 are each as defined above, —N(R15)R11, wherein R11 and R15 are each as defined above, or 2,3-epoxy-2-methylpropyl, 2-methyl-2-propenyl, 1,3dioxolan-2-yl or 1,3-dioxan-2-yl; or alternatively, R2 and R3 optionally form together a heterocyclic ring, whereby the compound of the formula (I) has the formula (a), (b) or (c):

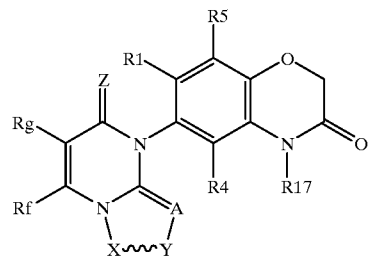

(a)

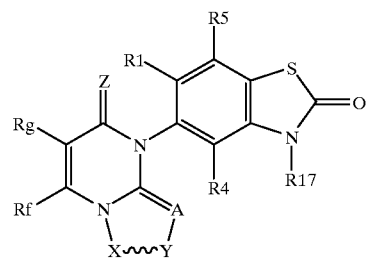

(b)

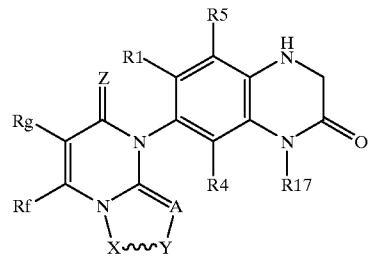

(c)

wherein Rf, Rg, A, X, Y, Z, R1, R4 and R5 of (a), (b) and (c) are each as defined above, and R17 represents $(C_1-C_6)$alkyl, $(C_3-C_8)$alkenyl, $(C_3-C_8)$alkynyl, $(C_1-C_4)$haloalkyl, $(C_3-C_8)$haloalkenyl, $(C_3-C_8)$haloalkynyl, $(C_1-C_6)$acyl, formyl, benzoyl, $(C_1-C_6)$haloalkylcarbonyl, phenacyl, $(C_3-C_8)$cycloalkyl$(C_1-C_4)$alkyl or $(C_1-C_4)$alkoxy$(C_1-C_4)$alkyl, or a group —Q—COR$_1$–C$_4$)alkyl, wherein Q is as defined above, —Q—CN, wherein Q is as defined above, or —Q-(optionally substituted phenyl group), wherein Q and the optionally substituted phenyl group are each as defined above;

provided that when optical isomers, diastereomers or geometrical isomers of the compounds defined above exist, both the mixture of said isomers and the isolated isomers are included.

2. The compound of claim 1, or a salt thereof, wherein:

Rf represents $(C_1-C_4)$haloalkyl;

X~Y represents:

N=N,

C(Ra)=C(Rb), wherein Ra and Rb each independently represents hydrogen, halogen, $(C_1-C_4)$alkyl, $(C_1-C_4)$alkoxy, $(C_1-C_4)$haloalkyl, hydroxy, amino, mercapto, carboxyl, hydroxymethyl, carbamoyl, formyl, $(C_1-C_4)$alkylcarbonyl, $(C_1-C_4)$alkoxycarbonyl, $(C_1-C_4)$alkylamino, $(C_2-C_6)$alkenyl, $(C_2-C_6)$alkynyl, $(C_1-C_4)$alkylmercapto, $(C_3-C_6)$alkenylamin $(C_3-C_6)$alkynylamino, benzyloxy, benzylamino, $(C_1-C_4)$alkylsulfinyl, $(C_1-C_4)$alkylsulfonyl or pyridyl, or phenyl which is optionally substituted with halogen, $(C_1-C_4)$alkyl, $(C_1-C_4)$alkoxy, $(C_1-C_4)$haloalkyl, $(C_1-C_4)$ haloalkoxy or phenyl,
C(Ra)=N, wherein Ra is as defined above,
N=C(Ra), wherein Ra is as defined above,
CH(Ra)CH(Rb), wherein Ra and Rb are each as defined above, or
$CH_2CH_2CH_2$, CH=$CHCH_2$ or $CH_2$CH=CH, or
NHC(Ra)Rb, wherein Ra and Rb are each as defined above,
C(Ra)(Rb)NH, wherein Ra and Rb are each as defined above, or
C(=O)C(=O), $CH_2$C(=O)NH or $CH_2CH_2SO_2$ or
C(=O)CH(Ra), wherein Ra is as defined above,
CH(Ra)C(=O), wherein Ra is the same as defined above, or
C(=O)NH, C(=S)NH, NHC(=O) or NHC(=S), or
C(=O)C(Ra)=N, wherein Ra is the as defined above,
C(=O)C(Ra)=C(Rb), wherein Ra and Rb are as defined above,
C(Ra)=C(Rb)C(=O), wherein Ra and Rb are as defined above,
N=C(Ra)C(=O), wherein Ra is as defined above,
CH(Ra)C(=O)NH, wherein Ra is as defined above,
C(=O)N(Ra)C(=O), wherein Ra is as defined above,
C(Ra)=NC(=O), wherein Ra is as defined above,
C(Ra)O, wherein Ra is as defined above,
C(=O)O, OC(=O) or SC(=O);

A is a nitrogen atom or CH;

Z is:
  oxygen or sulfur,
  NRc, wherein Rc is a hydrogen atom, or $(C_1-C_4)$alkyl, $(C_1-C_4)$alkoxycarbonyl or $(C_1-C_4)$ alkoxycarbonylmethyl, or phenyl which is optionally substituted with halogen or $(C_1-C_4)$alkyl, $(C_1-C_4)$ alkoxy or $(C_1-C_4)$haloalkyl, or
  $NNHR_c$, wherein Rc is as defined above;

Rg represents hydrogen, halogen, cyano, $(C_1-C_4)$ alkoxycarbonyl, $(C_3-C_6)$alkenyl, $(C_3-C_6)$alkynyl or $(C_1-C_4)$alkyl;

R1 represents hydrogen or halogen;

R5 represents hydrogen or halogen;

R2 represents:
  hydrogen, halogen, nitro, cyano, thiocarbamoyl, carbamoyl, mercapto, hydroxyl, amino, formyl, carboxyl, vinyl, ethynyl, trimethylsilylethynyl, cyanomethyl, sulfamoyl, phenyl, benzyl, $(C_1-C_8)$ alkyl, $(C_3-C_8)$alkenyl, $(C_3-C_8)$alkynyl, $(C_1-C_4)$ haloalkyl, $(C_1-C_4)$alkoxy, $(C_1-C_4)$haloalkoxy, $(C_3-C_8)$haloalkenyl, $(C_3-C_8)$haloalkynyl, $(C_1-C_4)$ acyl, $(C_1-C_4)$alkylsulfonyl, $(C_1-C_4)$alkylthio or $(C_1-C_4)$alkoxy$(C_1-C_2)$alkyl group, or a group —CO$R_1-C_4)$alkyl, —CON[$(C_1-C_4)$alkyl]$_2$, —CONH$(C_1-C_4)$alkyl, —NH—$(C_1-C_4)$alkyl, —N[$(C_1-C_4)$alkyl]$_2$, —O—$CH_2CO_2(C_1-C_4)$alkyl, —S—$CO_2(C_1-C_4)$alkyl or —$NHCH_2CO_2(C_1-C_4)$ alkyl, or a group —O—Q-(optionally substituted phenyl group, wherein Q represents a saturated or unsaturated $(C_1-C_6)$alkylene chain which is optionally branched and substituted with halogen and the optionally substituted phenyl group is a phenyl which is optionally substituted with halogen, $(C_1-C_4)$haloalkyl, $(C_1-C_4)$alkyl, $(C_1-C_4)$alkoxy, $(C_1-C_4)$haloalkoxy, methanesulfonyl, $(C_1-C_4)$ alkoxycarbonyl, nitro, hydroxyl, amino or cyano, or a group —O—CH($CH_3$)$CO_2(C_1-C_4)$alkyl or —O—$CH_2$COR$_1-C_4)$alkyl;

R3 represents:
  hydrogen, halogen, nitro, cyano, thiocarbamoyl, carbamoyl, mercapto, hydroxyl, amino, formyl, carboxyl, vinyl, ethynyl, cyanomethyl, sulfamoyl, $(C_1-C_8)$alkyl, $(C_3-C_8)$alkenyl, $(C_1-C_4)$ alkylsulfonyl, $(C_3-C_8)$alkynyl, $(C_3-C_8)$cycloalkyl, $(C_1-C_4)$haloalkyl, $(C_3-C_8)$haloalkenyl, $(C_3-C_8)$ haloalkynyl, $(C_1-C_4)$acyl, $(C_1-C_4)$alkoxy$(C_1-C_2)$ alkyl or $(C_1-C_4)$alkylsulfinyl, or
  phenyl which is optionally substituted with halogen or $(C_1-C_4)$haloalkyl, $(C_1-C_4)$alkyl, $(C_1-C_4)$alkoxy, $(C_1-C_4)$haloalkoxy, methanesulfonyl, $(C_1-C_4)$ alkoxycarbonyl, nitro hydroxyl, amino or cyano, or a group —O—CH($CH_3$)$CO_2(C_1-C_4)$alkyl or —O—$CH_2$COR$_1-C_4)$alkyl,
  a group —Q-(optionally substituted phenyl group), wherein Q and the optionally substituted phenyl group are each as defined above,
  a group —O—Q-(optionally substituted phenyl group), wherein Q and the optionally substituted phenyl group are each as defined above,
  a group —S—Q-(optionally substituted phenyl group), wherein Q and the optionally substituted phenyl group are each as defined above,
  a group —NH—Q-(optionally substituted phenyl group), wherein Q and the optionally substituted phenyl group are each as defined above,
  a group —O-(optionally substituted phenyl group), wherein the optionally substituted phenyl group is as defined above,
  a group —S-(optionally substituted phenyl group), wherein the optionally substituted phenyl group is as defined above, or
  a group —NH-(optionally substituted phenyl group), wherein the optionally substituted phenyl group is as defined above, or
  —O—R11, wherein R11 represents $(C_1-C_8)$alkyl, $(C_3-C_8)$cycloalkyl, $(C_3-C_8)$cycloalkyl$(C_1-C_4)$alkyl $(C_3-C_8)$alkenyl, $(C_3-C_8)$alkynyl, $C_3-C_8)$ haloalkenyl, $(C_1-C_4)$haloalkylcarbonyl, $(C_3-C_8)$ haloalkynyl, $(C_1-C_4)$haloalkyl, $(C_1-C_4)$alkoxy $(C_1-C_4)$alkyl, cyanomethyl or $(C_1-C_4)$acyl,
  —NH—R11, wherein R11 is as defined above,
  —S—R11, wherein R11 is as defined above,
  —$CO_2R12$, wherein R12 is a $(C_1-C_8)$alkyl, $(C_3-C_8)$ cycloalkyl, $(C_3-C_8)$alkenyl, $(C_3-C_8)$alkynyl, oxetane-3-yl, $(C_1-C_4)$alkoxycarbonylmethyl, [$(C_1-C_4)$alkyl]$_2$amino, phenyl or benzyl,
  —CONHR12, wherein R12 is as defined above,
  —Q—$CO_2R12$, wherein Q and R12 are each as defined above,
  —O—Q—$CO_2R12$, wherein Q and R12 are each as defined above,
  —NH—Q—$CO_2R12$, wherein Q and R12 are each as defined above,
  —S—Q—$CO_2R12$, wherein Q and R12 are each as defined above,
  —$NHSO_2R13$, wherein R13 is a $(C_1-C_8)$alkyl, $(C_1-C_4)$haloalkyl, $(C_3-C_6)$cycloalkyl, $(C_3-C_8)$ alkenyl, $(C_3-C_8)$alkynyl, benzyl or phenyl,
  —N($SO_2R13$)$_2$, wherein R13 is as defined above,
  —$CONHSO_2R14$, wherein R14 is a $(C_1-C_4)$alkyl or $(C_1-C_4)$haloalkyl group,
  —N(R15)$SO_2R13$, wherein R13 is as defined above and R15 is a $(C_1-C_6)$alkyl, $(C_3-C_8)$alkenyl, $(C_3-C_8)$ alkynyl, $(C_1-C_4)$haloalkyl, $(C_3-C_8)$haloalkenyl, $(C_3-C_8)$haloalkynyl, $(C_1-C_6)$acyl, formyl, cyano ($C_1$–$C_4$)alkyl, ($C_1$–$C_4$)alkoxy($C_1$–$C_4$)alkyl or ($C_1$–$C_4$)alkoxycarbonyl, or a group —C(=O) (optionally substituted phenyl group), wherein the optionally substituted phenyl group is as defined above, —NHCO$_2$R16, wherein R16 is a ($C_1$–$C_6$)alkyl, ($C_3$–$C_8$)alkenyl, ($C_3$–$C_8$)alkynyl, ($C_1$–$C_4$)haloalkyl or phenyl, or a group —Q-(optionally substituted phenyl group), wherein Q and the optionally substituted phenyl group are each as defined above, —O—CO$_2$R16, wherein R16 is as defined above, —N(R15)CO$_2$R16, wherein R15 and R16 are each as defined above, or —N(R15)R11, wherein R11 and R15 are each as defined above;

R4 represents hydrogen, halogen, 2,3-epoxy-2methylpropyl, 2-methyl-2-propenyl, 1,3-dioxolan-2-yl or 1,3dioxan-2-yl; or alternatively, R2 and R3 optionally form together a heterocyclic ring, whereby the compound of the formula (I) has the formula (a), (b) or (c):

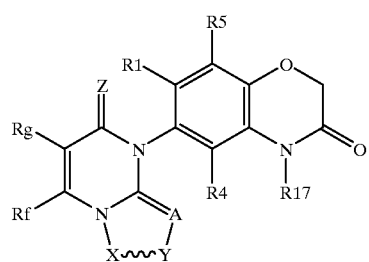
(a)

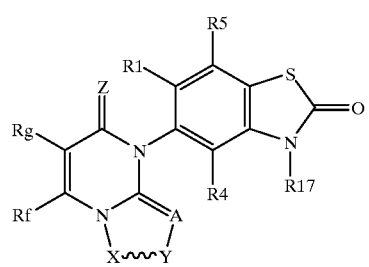
(b)

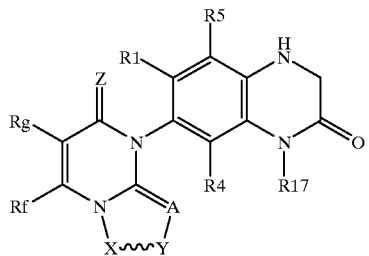
(c)

wherein Rf, Rg, A, X, Y, Z, R1, R4 and R5 of (a), (b) and (c) are each as defined above, and R17 is ($C_1$–$C_6$)alkyl, ($C_3$–$C_8$)alkenyl, ($C_3$–$C_8$)alkynyl, ($C_1$–$C_4$)haloalkyl, ($C_3$–$C_8$)haloalkenyl, ($C_3$–$C_8$)haloalkynyl, ($C_1$–$C_6$)acyl, formyl, benzoyl, ($C_1$–$C_6$)haloalkylcarbonyl, phenacyl, ($C_3$–$C_8$)cycloalkyl($C_1$–$C_4$)alkyl or ($C_1$–$C_4$)alkoxy($C_1$–$C_4$)alkyl, or a group —Q—CO$_2$($C_1$–$C_4$)alkyl, wherein Q is as defined above, —Q—CN, wherein Q is as defined above or —Q-(optionally substituted phenyl group), wherein Q and the optionally substituted phenyl group are each as defined above.

3. The compound of claim 1, wherein Rf is CF$_3$, Rg is hydrogen, Z is oxygen, R1 is hydrogen or halogen, R4 is hydrogen or halogen, R5 is hydrogen or halogen, and R2 is halogen, nitro, cyano, or thiocarbamoyl.

4. The compound of claim 1, wherein A is nitrogen and X~Y is CH=CH.

5. The compound of claim 1, wherein R3 is —OR11, —CO$_2$R12, —Q—CO$_2$R12, —O—Q—CO$_2$R12, —S—Q—CO$_2$R12, —NHSO$_2$R13, —N(R15)SO$_2$R13 or —NHCO$_2$R16.

6. A herbicidal composition, which comprises:
a) an effective amount of one or more compounds of claim 1, and
b) a carrier.

7. A method of inhibiting weed growth, which comprises applying an effective amount of one or more compounds of claim 1, to a crop growth area.

8. The method of claim 7, wherein said crop growth area is an upland field or paddy field.

9. The method of claim 7, wherein said crop growth area contains one or more growing crops selected from the group consisting of rice, wheat, corn, soybean, cotton and sugar beet.

* * * * *